US012558297B2

(12) United States Patent
Popplewell et al.

(10) Patent No.: US 12,558,297 B2
(45) **Date of Patent: *Feb. 24, 2026**

(54) CONSUMER PRODUCT WITH CONTROLLED RELEASE, BIODEGRADABLE CORE-SHELL MICROCAPSULE COMPOSITIONS

(71) Applicant: International Flavors & Fragrances Inc., New York, NY (US)

(72) Inventors: Lewis Michael Popplewell, Union Beach, NJ (US); Ronald Gabbard, Union Beach, NJ (US); Yabin Lei, Union Beach, NJ (US); Takashi Sasaki, Union Beach, NJ (US); Julie Ann Wieland, Union Beach, NJ (US); Li Xu, Union Beach, NJ (US); Yi Zhang, Union Beach, NJ (US); Niels Akeroyd, Hilversum (NL); Volkert De Villeneuve, Hilversum (NL); Rob Hunter, Hilversum (NL); Judith Kerschner, Union Beach, NJ (US); Valery Claude, Union Beach, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 572 days.

This patent is subject to a terminal disclaimer.

(21) Appl. No.: 17/602,073

(22) PCT Filed: Dec. 17, 2019

(86) PCT No.: PCT/US2019/066798

§ 371 (c)(1),
(2) Date: Oct. 7, 2021

(87) PCT Pub. No.: WO2020/209908

PCT Pub. Date: Oct. 15, 2020

(65) Prior Publication Data

US 2022/0175636 A1 Jun. 9, 2022

Related U.S. Application Data

(60) Provisional application No. 62/833,288, filed on Apr. 12, 2019.

(51) Int. Cl.

| | |
|---|---|
| ***A61K 8/11*** | (2006.01) |
| ***A61K 8/64*** | (2006.01) |
| ***A61K 8/73*** | (2006.01) |
| ***A61Q 5/02*** | (2006.01) |
| ***A61Q 5/12*** | (2006.01) |
| ***A61Q 15/00*** | (2006.01) |
| ***A61Q 19/00*** | (2006.01) |
| ***C11D 3/50*** | (2006.01) |

(52) U.S. Cl.

CPC ................ *A61K 8/11* (2013.01); *A61K 8/645* (2013.01); *A61K 8/73* (2013.01); *A61K 8/732* (2013.01); *A61Q 5/02* (2013.01); *A61Q 5/12* (2013.01); *A61Q 15/00* (2013.01); *A61Q 19/007* (2013.01); *C11D 3/505* (2013.01); *A61K 2800/412* (2013.01)

(58) Field of Classification Search

CPC .... A61K 2800/412; A61K 8/11; A61K 8/645; A61K 8/73; A61K 8/731; A61K 8/732; A61K 8/735; A61Q 15/00; A61Q 19/00; A61Q 19/007; A61Q 5/02; A61Q 5/12; C11D 17/0039; C11D 3/505

See application file for complete search history.

(56) References Cited

U.S. PATENT DOCUMENTS

| | | | | |
|---|---|---|---|---|
| 4,002,598 | A | 1/1977 | Waddill et al. | |
| 4,138,362 | A | 2/1979 | Vassiliades et al. | |
| 4,946,624 | A | 8/1990 | Michael | |
| 8,119,587 | B2 | 2/2012 | Cavin et al. | |
| 8,765,659 | B2 | 7/2014 | Gizaw et al. | |
| 9,011,887 | B2 | 4/2015 | Chieffi et al. | |
| 9,080,061 | B2 | 7/2015 | Palmer et al. | |
| 9,464,263 | B2 | 10/2016 | Aussant et al. | |
| 9,504,274 | B2 | 11/2016 | George et al. | |
| 9,725,684 | B2 | 8/2017 | Fernandes et al. | |
| 9,770,608 | B2 | 9/2017 | Reijmer et al. | |
| 10,034,819 | B2 | 7/2018 | Dardelle et al. | |
| 10,188,593 | B2 | 1/2019 | Dihora et al. | |
| 10,537,503 | B2 * | 1/2020 | Lei ........................ | C11D 3/505 |
| 11,540,985 | B2 * | 1/2023 | Lei ........................ | A61K 8/736 |
| 2004/0071742 | A1 | 4/2004 | Popplewell et al. | |
| 2007/0078071 | A1 * | 4/2007 | Lee ......................... | A61K 8/11 510/141 |
| 2010/0180386 | A1 | 7/2010 | Bianchetti et al. | |
| 2012/0237578 | A1 | 9/2012 | Lei et al. | |

(Continued)

FOREIGN PATENT DOCUMENTS

| | | |
|---|---|---|
| CN | 101984185 B | 9/2012 |
| EP | 2934464 B1 | 2/2018 |

(Continued)

OTHER PUBLICATIONS

Azhar et al.; Materials Today: Proceedings 47 (2021) 1371-1375. Published online May 19, 2021.*
International Preliminary Report on Patentability in PCT/US2019/066798, dated Sep. 28, 2021.
International Search Report and Written Opinion in PCT/US2019/066798, dated Mar. 2, 2020.

*Primary Examiner* — Jeffrey T. Palenik

(57) ABSTRACT

A consumer product with controlled release of an active material is provided, wherein said active material is encapsulated in a biodegradable core-shell microcapsule composition, wherein the shell of the microcapsule is composed of a biopolymer.

11 Claims, No Drawings

(56) References Cited

U.S. PATENT DOCUMENTS

| | | | | |
|---|---|---|---|---|
| 2013/0017239 | A1 | 1/2013 | Petit et al. | |
| 2013/0216596 | A1 | 8/2013 | Petit et al. | |
| 2014/0010859 | A1 | 1/2014 | Chen et al. | |
| 2015/0164117 | A1 | 6/2015 | Kaplan et al. | |
| 2015/0203787 | A1 | 7/2015 | Lei et al. | |
| 2017/0367373 | A1 | 12/2017 | Bleiel et al. | |
| 2018/0015009 | A1 | 1/2018 | Soubiran et al. | |
| 2018/0021241 | A1 | 1/2018 | Lei et al. | |
| 2018/0078468 | A1 | 3/2018 | Jerri et al. | |
| 2020/0297592 | A1* | 9/2020 | Bouquerand | A23L 27/72 |
| 2022/0125700 | A1* | 4/2022 | Lei | A61Q 5/06 |
| 2022/0177815 | A1* | 6/2022 | Popplewell | C11D 17/0039 |
| 2022/0226797 | A1* | 7/2022 | Popplewell | C08L 89/00 |

FOREIGN PATENT DOCUMENTS

| | | | | | |
|---|---|---|---|---|---|
| EP | 2588066 | B1 | | 3/2018 | |
| FR | 2275250 | A1 | | 10/1981 | |
| WO | 2014044840 | A1 | | 3/2014 | |
| WO | WO2016/144798 | A1 | * | 9/2016 | A61K 9/50 |
| WO | 2016185171 | A1 | | 11/2016 | |
| WO | 2017102812 | A1 | | 6/2017 | |
| WO | 2018002214 | A1 | | 1/2018 | |
| WO | 2018019894 | A1 | | 2/2018 | |
| WO | WO2018/053356 | A1 | * | 3/2018 | B01J 13/06 |
| WO | 2019243425 | A1 | | 12/2019 | |
| WO | 2019243426 | A1 | | 12/2019 | |
| WO | 2020131956 | A1 | | 6/2020 | |

* cited by examiner

CONSUMER PRODUCT WITH CONTROLLED RELEASE, BIODEGRADABLE CORE-SHELL MICROCAPSULE COMPOSITIONS

INTRODUCTION

This application is a U.S. National Stage Application of PCT/US2019/066798 filed Dec. 17, 2019 and claims benefit of priority to U.S. Provisional Patent Application Ser. No. 62/833,288, filed Apr. 12, 2019, the contents of each of which are incorporated herein by reference in their entirety.

BACKGROUND

Fragrance materials are used in numerous products to enhance the consumer's enjoyment of a product. Fragrance materials are added to consumer products such as laundry detergents, fabric softeners, soaps, detergents, personal care products, such as shampoos, body washes, deodorants and the like, as well as numerous other products.

In order to enhance the effectiveness of the fragrance materials for the user, various technologies have been used to deliver the fragrance materials at the desired time. One widely used technology is encapsulation of the fragrance material in a protective coating, which protects the fragrance material from evaporation, reaction, oxidation or otherwise dissipating prior to use. Frequently the protective coating is a synthetic polymeric material such as melamine formaldehyde, polyurea, or polyacrylate. However, consumers prefer environment friendly products over synthetic polymers.

Natural and naturally-derived materials such as hydroxyethylcellulose have been conventionally used as gelling and thickening agents and disclosed for use as emulsifiers (see, e.g., U.S. Pat. No. 8,765,659 B2, U.S. Pat. No. 9,725,684 B2, CN 101984185B, US 2013/0017239 A1, and US 2010/0180386A1) and coating materials (see, e.g., U.S. Pat. No. 9,011,887 B2, US 2018/0078468, EP 2934464 B1 and US 2013/0216596 A1). Further, microparticles prepared with polysaccharides (U.S. Pat. No. 10,188,593 B2) and microcapsules prepared with natural materials such as chitosan (WO 2016/185171, U.S. Pat. No. 4,138,362); Silk fibroin (US 2015/0164117 A1); polyelectrolytes (U.S. Pat. No. 10,034,819 B2, WO 2018/002214 A1); gelatin (U.S. Pat. No. 4,946,624, EP 2588066 B1, U.S. Pat. No. 8,119,587 B2); gums, proteins or pectin (US 2018/0078468 A1, WO 2018/019894 A1, CN 101984185 B), and in combination with synthetic polymers (WO 2017/102812 A1, FR 2,275,250) have been described.

However, there is a need to develop environment friendly microcapsules with tailored retention and fragrance release characteristics, which exhibit a high performance in laundry, washing, cleaning, surface care and personal and skin care applications.

SUMMARY OF THE INVENTION

This invention provides a consumer product with controlled release of an active material, wherein the consumer product includes (a) a consumer product base; and (b) a biodegradable core-shell microcapsule composition, (i) the core of the biodegradable core-shell microcapsule comprising at least one active material, and (ii) the shell of the biodegradable core-shell microcapsule comprising at least one biopolymer cross-linked with one or more cross-linking agents, wherein said microcapsule retains the at least one active material for at least four weeks at elevated temperature in the consumer product base and releases the at least one active material in response to at least one triggering condition.

In some embodiments, the consumer product base includes one or more bleach activators, surfactants, builders, chelating agents, dye transfer inhibiting agents, dispersants, enzymes, and enzyme stabilizers, catalytic metal complexes, polymeric dispersing agents, deposition agents, clay and soil removal or anti-redeposition agents, brighteners, suds suppressors, dyes, perfumes and perfume delivery systems, structure elasticizing agents, fabric softeners, carriers, hydrotropes, processing aids, structurants, anti-agglomeration agents, formaldehyde scavengers, pigments, or a combination thereof.

In other embodiments, the consumer product is a baby care product, a diaper rash cream or balm, a baby powder, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a diaper, a bib, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, or a wildlife scent.

In certain embodiments, the at least one biopolymer is a whey protein, plant storage protein, gelatin, starch, modified starch, dextran, dextrin, cellulose, modified cellulose, hemicellulose, pectin, chitin, chitosan, gum, modified gum, lignin, or a combination thereof, wherein the whey protein or plant storage protein is optionally denatured.

In other embodiments, the one or more cross-linking agents are selected from an aldehyde, epoxy compound, polyvalent metal cation, polyphenol, maleimide, sulfide, phenolic oxide, hydrazide, isocyanate, isothiocyanate, N-hydroxysulfosuccinimide derivative, carbodiimide derivative, polyol, amine, enzyme, or a combination thereof.

An active material of the microcapsules may include, but is not limited to, a fragrance, pro-fragrance, flavor, malodor counteractive agent, vitamin or derivative thereof, anti-inflammatory agent, fungicide, anesthetic, analgesic, anti-microbial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or a combination thereof.

DETAILED DESCRIPTION OF THE INVENTION

This invention focuses on consumer products containing microcapsules produced with natural and naturally-derived materials that provide both desirable, positive attributes and biodegradability. In particular, the invention provides consumer products with core-shell microcapsules, wherein the shell is composed primarily of natural wall polymers and the microcapsules are stable in the consumer product base for at least four weeks at elevated temperature and release the active material under appropriate triggering conditions, e.g., friction, swelling, a pH change, an enzyme, a change in temperature, a change in ionic strength, or a combination thereof. The desired performance and stability characteristics of the microcapsules in the consumer product are achieved by cross-linking water-soluble natural polymers with a combination of selected cross-linking agents. Accordingly, this invention is a consumer product with controlled release of an active material encapsulated in a biodegradable core-shell microcapsule, as well as methods of producing and using the same.

A. Biodegradable Core-Shell Microcapsule Composition

The biodegradable core-shell microcapsule composition of this invention has a core including at least one active material, and a shell composed of at least one biopolymer cross-linked with one or more cross-linking agents. "Biodegradable" as used herein with respect to a material, such as a microcapsule as a whole and/or a biopolymer of the microcapsule shell, has no real or perceived health and/or environmental issues, and is capable of undergoing and/or does undergo physical, chemical, thermal, microbial and/or biological degradation. Ideally, a microcapsule and/or biopolymer is deemed "biodegradable" when the microcapsule and/or biopolymer passes one or more of the Organization for Economic Co-operation and Development (OECD) tests including, but not limited to OECD 301/310 (Ready biodegradation), OECD 302 (inherent biodegradation), ISO 17556 (solid stimulation studies), ISO 14851 (fresh water stimulation studies), ISO 18830 (marine sediment stimulation studies), OECD 307 (soil stimulation studies), OECD 308 (sediment stimulation studies), and OECD 309 (water stimulation studies). In particular embodiments, the microcapsules are readily biodegradable as determined using the OECD 310 test. The pass level for ready biodegradability under OECD 310 is 60% of $ThCO_2$ production is reached in a 10-d window within the 28-d period of the test.

As used herein, a "core-shell microcapsule," or more generically a "microcapsule" or "capsule," is a substantially spherical structure having a well-defined core and a well-defined envelope or wall. The "core" is composed of any active material or material submitted to microencapsulation. The "wall" is the structure formed by the microencapsulating biopolymer around the active material core being microencapsulated. In general, the wall of the microcapsule is made of a continuous, polymeric phase with an inner surface and outer surface. The inner surface is in contact with the microcapsule core. The outer surface is in contact with the environment in which the microcapsule resides, e.g., a water phase, skin, or hair. Ideally, the wall protects the core against deterioration by oxygen, moisture, light, and effect of other compounds or other factors; limits the losses of volatile core materials; and releases the core material under desired conditions. In this respect, the core-shell microcapsules of this invention provide controlled release of the active material. As used herein, "controlled release" refers to retention of the active material in the core until a specified triggering condition occurs. Such triggers include, e.g., friction, swelling, a pH change, an enzyme, a change in temperature, a change in ionic strength, or a combination thereof.

As used in the context of this invention, a "biodegradable core-shell microcapsule composition" refers to a slurry or suspension of biodegradable core-shell microcapsules produced in accordance with the methods and examples described herein. The biodegradable core-shell microcapsule composition of this invention may be used directly in a consumer product, washed, coated, dried (e.g., spray-dried) and/or combined with one or more other microcapsule compositions, active materials, and/or carrier materials.

B. Biopolymer Wall Material

For the purposes of this invention, a "biopolymer" is a polymer obtained from a natural source (e.g., a plant, fungus, bacterium or animal) or modified biopolymer thereof. In some embodiments, the biopolymer used in the preparation of the microcapsules is water soluble (i.e., water soluble prior to being cross-linked). In other embodiments, the biopolymer is a polypeptide, polysaccharide or polyphenolic compound. In certain embodiments, the biopolymer of the microcapsule wall is a single type of polymer, e.g., a polypeptide, a polysaccharide or a polyphenolic compound. In other embodiments, the biopolymer of the microcapsule wall is a combination of polymers, e.g., (a) at least one polypeptide in combination with at least one polysaccharide, (b) at least one polypeptide in combination with at least one polyphenolic compound, (c) at least one polysaccharide in combination with at least one polyphenolic compound, or (d) at least one polypeptide in combination with at least one polysaccharide and at least one polyphenolic compound.

Polypeptide Biopolymers. As is conventional in the art, a "polypeptide" or "protein" is a linear organic polymer composed of amino acid residues bonded together in a chain, forming part of (or the whole of) a protein molecule. "Polypeptide" or "protein," as used herein, means natural polypeptides and polypeptide derivatives and/or modified polypeptides. The polypeptide may exhibit an average molecular weight of from about 1,000 Da to about 40,000,000 Da and/or greater than 10,000 Da and/or greater than 100,000 Da and/or greater than 1,000,000 Da and/or less than 3,000,000 Da and/or less than 1,000,000 Da and/or less than 500,000 Da, or a range delimited by any one of these molecular weights.

In some embodiments of this invention, the shell of the biodegradable core-shell microcapsule includes at least one polypeptide as the biopolymer. In other embodiments, the shell of the biodegradable core-shell microcapsule includes at least two, three, four, five or more polypeptides as the biopolymer. In this respect, a polypeptide of use in the preparation of a microcapsule of the invention can be a single, individual polypeptide or a combination of polypeptides. Exemplary polypeptides and polypeptide combinations include, but are not limited to, gelatin, whey protein (e.g., a concentrate or isolate), plant storage protein (e.g., a concentrate or isolate), or a combination thereof.

As used herein, "whey protein" refers to the proteins contained in whey, a dairy liquid obtained as a supernatant of curds when milk or a dairy liquid containing milk components, is processed into cheese curd to obtain a cheese-making curd as a semisolid. Whey protein is generally understood in principle to include the globular proteins β-lactoglobulin and α-lactalbumin. It may also include lower amounts of immunoglobulin and other globulins. The term "whey protein" is also intended to include partially or completely modified or denatured whey proteins. Purified β-lactoglobulin and/or α-lactalbumin polypeptides may also be used in preparation of microcapsules of this invention.

Plant storage proteins are proteins that accumulate in various plant tissues and function as biological reserves of metal ions and amino acids. Plant storage proteins can be classified into two classes: seed or grain storage proteins and vegetative storage proteins. Seed/grain storage proteins are a set of proteins that accumulate to high levels in seeds/grains during the late stages of seed/grain development, whereas vegetative storage proteins are proteins that accumulate in vegetative tissues such as leaves, stems and, depending on plant species, tubers. During germination, seed/grain storage proteins are degraded and the resulting amino acids are used by the developing seedlings as a nutritional source. In some embodiments, the plant storage protein used in the preparation of a microcapsule of the invention is a seed or grain storage protein, vegetable storage protein, or a combination thereof. In certain embodiments, the seed storage protein is a leguminous storage protein. In particular embodiments, the seed/grain storage protein is extracted from leguminous plants and particularly from soya, lupine, pea, chickpea, alfalfa, horse bean, lentil, and haricot bean; from oilseed plants such as colza, cottonseed and sunflower; from cereals like wheat, maize, barley, malt, oats, rye and rice (e.g., brown rice protein), or a combination thereof. In other embodiments, the plant storage protein is a vegetable protein extracted from potato or sweet potato tubers.

In particular embodiments, the plant storage protein is intended to include a plant protein isolate, plant protein concentrate, or a combination thereof. Plant storage protein isolates and concentrates are generally understood to be composed of several proteins. For example, pea protein isolates and concentrates may include legumin, vicilin and convicilin proteins. Similarly, brown rice protein isolates may include albumin, globulin and glutelin proteins. The term "plant storage protein" is also intended to include a partially or completely modified or denatured plant storage protein. Individual storage polypeptides (e.g., legumin, vicilin, convicilin, albumin, globulin or glutelin) may also be used in preparation of microcapsules of this invention. Individual proteins may be isolated and optionally purified to homogeneity or near homogeneity, e.g., 90%, 92%, 95%, 97%, 98%, or 99% pure.

"Gelatin" refers to a mixture of proteins produced by partial hydrolysis of collagen extracted from the skin, bones, and connective tissues of animals. Gelatin can be derived from any type of collagen, such as collagen type I, II, III, or IV. Such proteins are characterized by including Gly-Xaa-Yaa triplets wherein Gly is the amino acid glycine and Xaa and Yaa can be the same or different and can be any known amino acid. At least 40% of the amino acids are preferably present in the form of consecutive Gly-Xaa-Yaa triplets.

In some embodiments, the whey protein or plant storage protein of this invention may be denatured, preferably without causing gelation of the whey protein or plant storage protein. Exemplary conditions for protein denaturation include, but are not limited to, exposure to heat or cold, changes in pH, exposure to denaturing agents such as detergents, urea, or other chaotropic agents, or mechanical stress including shear. In some embodiments, the whey protein or plant storage protein is partially denatured, e.g., 50%, 60%, 70%, 80% or 85% (w/w) denatured. In other embodiments, the whey protein or plant storage protein is substantially or completely denatured, e.g., at least 90%, 91%, 92%, 93%, 94%, 95%, 96%, 97%, 98%, 99% or 100% (w/w) denatured. For example, whereas treatment of whey protein at 85° C. for 5 to 10 minutes results in 65% to 80% denaturation of whey protein, treatment of whey protein at 85° C. for 25 to 30 minutes results in 95% to 99% denaturation (Qian, et al. (2017) *Korean J. Food Sci. Anim. Resourc.* 37(1):44-51). Further, when an 8% pea storage protein solution (w/v) is used, the solution may be treated at a temperature of 80° C. to 90° C. for 20 to 30 minutes (or preferably 85° C. for 25 minutes) to yield a substantially denatured pea storage protein. Accordingly, depending on the degree of denaturation desired, it will be appreciated that higher temperatures and shorter times may also be employed.

Notably, it has been found that the degree and method to denature the protein can have a significant impact on performance. In particular, it has been found that chaotropic agents are particularly useful in providing a denatured protein of use in the preparation of the biodegradable microcapsules of this invention. As is conventional in the art, a chaotropic agent is a compound which disrupts hydrogen bonding in aqueous solution, leading to increased entropy. Generally, this reduces hydrophobic effects which are essential for three dimensional structures of proteins. Chaotropes may be defined by having a positive chaotropic value, i.e., kJ $kg^{-1}$ mole on the Hallsworth Scale. Examples of chaotropicity values are, for example, $CaCl_2$+92.2 kJ $kg^{-1}$, $MgCl_2$ kJ $kg^{-1}$+54.0, butanol +37.4 kJ $kg^{-1}$, guanidine hydrochloride +31.9 kJ $kg^{1}$, and urea +16.6 kJ $kg^{-1}$. In certain embodiments, the chaotropic agent is a guanidinium salt, e.g., guanidinium sulphate, guanidinium carbonate, guanidinium nitrate or guanidinium chloride. In particular embodiments, the whey protein or plant storage protein is partially or completely denatured with guanidine carbonate.

The protein used in the biodegradable microcapsule can also be derivatized or modified (e.g., derivatized or chemically modified). For example, the protein can be modified by covalently attaching sugars, lipids, cofactors, peptides, or other chemical groups including phosphate, acetate, methyl, and other natural or unnatural molecule.

Polysaccharide Biopolymers. A "polysaccharide" or "carbohydrate" refers to a molecule composed of sugar molecules bonded together. "Polysaccharide," as used herein, means natural polysaccharides and polysaccharide derivatives and/or modified polysaccharides, which are ideally water-soluble (prior to being cross-linked). The polysaccharide may exhibit an average molecular weight of from about 10,000 to about 40,000,000 g/mol and/or greater than 100, 000 g/mol and/or greater than 1,000,000 g/mol and/or greater than 3,000,000 g/mol and/or greater than 3,000,000 to about 40,000,000 g/mol.

In some embodiments of this invention, the shell of the biodegradable core-shell microcapsule includes at least one polysaccharide as the biopolymer. In other embodiments, the shell of the biodegradable core-shell microcapsule includes at least two, three, four, five or more polysaccharides as the biopolymer. In this respect, a polysaccharide of use in the preparation of a microcapsule of the invention can be a single, individual polysaccharide or a combination of polysaccharides. Exemplary polysaccharides include, but are not limited to, starch, modified starch, dextran, dextrin, cellulose, modified cellulose, hemicellulose, pectin, chitin, chitosan, gum, lignin, modified gum, or a combination thereof.

"Starch" generally refers to a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). As used herein, "starch" includes any naturally occurring unmodified starch, modified starch, synthetic starch or a combination thereof, as well as mixtures of the amylose or amylopectin fractions. Starch may be modified by physical, chemical, or biological processes, or combinations thereof. For example, the starch may be an octenyl succinic acid anhydride modified starch. The choice of unmodified or modified starch may depend on the end product desired. In one embodiment, the starch or starch mixture has an amylopectin content from about 20% to about 100%, more typically from about 40% to about 90%, even more typically from about 60% to about 85% by weight of the starch or mixtures thereof. Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

"Dextrin" is a water-soluble polysaccharide obtained from starch by the action of heat, acids, or enzymes. The term "dextrin," in its broadest sense, may refer to any product obtained by any method (e.g., heat, acid, enzyme) for degrading the starch. The tensile strength of dextrin film is lower than that for starch and decreases with the degree of conversion.

"Dextran" is a complex branched polysaccharide synthetized from sucrose by certain lactic-acid bacteria, e.g., *Leuconostoc bacteroides* and *Streptococcus mutans*. Dextran chains are of varying lengths (from 3 to 2000 KDa) and are composed of α-1,6 glycosidic linkages between glucose monomers, with branches from α-1,3 linkages. This characteristic branching distinguishes a dextran from a dextrin, which is a straight chain glucose polymer tethered by α-1,4 or α-1,6 linkages.

"Cellulose" is a complex carbohydrate or polysaccharide, composed of a linear chain of β-1,4 linked D-glucose units. Cellulose is the main substance found in plant cell walls, but is also produced by some bacteria. However, unlike plant-based cellulose, bacterial cellulose is highly pure and does not need to be separated from lignin in processing. Accordingly, in some embodiments, the cellulose used in the preparation of the microcapsules of this invention is a plant cellulose, whereas in other embodiments, the cellulose used in the preparation of the microcapsules of this invention is a bacterial cellulose.

As is known in the art, modification of cellulose by etherification chemistries increases the water solubility of cellulose by decreasing the crystallinity of the cellulose molecule. Accordingly, in certain embodiments of this invention, the cellulose is a modified cellulose, in particular a cellulose ether. Examples of modified celluloses include, but are not limited to, carboxymethylcellulose, hydroxyethylcellulose, carboxymethyl hydroxyethyl cellulose, hydroxypropyl cellulose, ethyl hydroxyethyl cellulose, methyl ethyl hydroxyethyl cellulose, or a combination thereof.

In certain embodiments, the wall of the biodegradable microcapsule of this invention is composed of hydroxyethyl cellulose (HEC). HEC is a nonionic, water-soluble polymer, and typically has a molar mass of 1000 Daltons to 10,000,000 Daltons. Commercial HEC products are sold as a white, free-flowing granular powder under the trademarks of NATROSOL® (Ashland, Covington, KY), CELLOSIZE® (Dow, Midland, MI), and TYLOSE® (ShinEtsu, Tokyo, Japan)

HEC may be prepared by reacting ethylene oxide with alkali-cellulose under controlled conditions, in which ethylene oxide reacts with a hydroxy group on cellulose to form a hydroxyethyl substitution on an anhydroglucose unit of the cellulose. An idealized HEC structure is shown below, with one hydroxyethyl group substitution on the anhydroglucose unit at right and two hydroxyethyl groups on the unit at left:

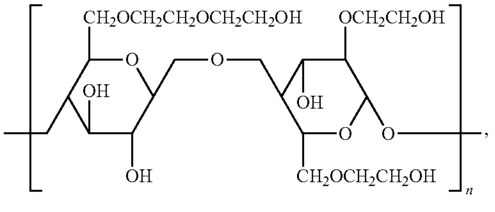

wherein n is typically 200 to 4000.

The manner in which the hydroxyethyl groups are added to the anhydroglucose units can be described by degree of substitution (DS) and/or molar substitution (MS). The degree of substitution refers to the average number of hydroxy groups on each anhydroglucose unit that have been reacted with ethylene oxide. A suitable HEC for use in this invention has a DS of 0.01 to 3 (e.g., 0.15 to 0.2, 0.5 to 3, 1 to 3, 0.5 to 1.5, 0.1, 0.5, 1, 1.5, 2, and 3). The molar substitution (MS) refers to the average number of ethylene oxide added to each anhydroglucose unit. An HEC of use in this invention can have an MS of 0.1 to 5 (e.g., 0.5 to 4, 1 to 3, 1.5, and 2).

Hemicelluloses are polysaccharides that are biosynthesized in the majority of plants, where they act as a matrix material present between the cellulose microfibrils and as a linkage between lignin and cellulose. Hemicelluloses are substituted/branched polymers of low to high molecular weight. They are composed of different sugar units arranged in different portions and with different substituents. Pentosan-rich polysaccharides have a prevalent pentose content and constitute the largest group of hemicelluloses. As used herein a "pentosan-rich polysaccharide" refers to a polysaccharide having a pentosan content of at least 20% by weight, and a xylose content of at least 20% by weight; for example, the polysaccharide has a pentosan content of 40% to 80% by weight, and a xylose content of 40% to 75% by weight.

Hemicelluloses of use in this invention include, but are not limited to, arabinoxylans, glucuronoxylans, glucuronoarabinoxylans, arabinoglucuronoxylans, glucomannans, galactoglucomannans, arabinogalactans, xyloglucans or a combination thereof. A hemicellulose can have a molecular weight of less than 50000 g/mol. Ideally, the hemicellulose has a molecular weight greater than 8000 g/mol. For example, the hemicellulose may have a molecular weight in the range of 8000 g/mol to 50000 g/mol, 8000 g/mol to 48000 g/mol or 8000 g/mol to 45000 g/mol. The use of low molecular weight hemicelluloses (i.e., in the range of 8000 g/mol to 15000 g/mol) is advantageous because such hemicelluloses can be obtained from many sources and the extraction procedure is relatively simple. The use of somewhat higher molecular weights (e.g., 15000 g/mol to 50000 g/mol, 20000 g/mol to 48000 g/mol, or 20000 g/mol to 40000 g/mol) facilitates film formation. If even higher molecular weights are used, high viscosity can complicate the use of the hemicellulose and the extraction methods are more restricted.

In certain embodiments, the invention encompasses the use of pentosan-rich polysaccharides, in particular xylans. Xylans are present in biomass such as wood, cereals, grass and herbs. To separate xylans from other components in various sources of biomass, extraction with water and aqueous alkali can be used. Xylans are also commercially available from sources as Sigma Chemical Company.

Xylans may be divided into the sub-groups of heteroxylans and homoxylans. The chemical structure of homoxylans and heteroxylans differs. Homoxylans have a backbone of xylose residues and have some glucuronic acid or 4-O-methyl-glucuronic acid substituents. Heteroxylans also have a backbone of xylose residues, but are in contrast to homoxylans extensively substituted not only with glucuronic acid or 4-O-methyl-glucuronic acid substituents but also with arabinose residues. An advantage of homoxylans compared to heteroxylans is that homoxylans crystallize to a higher extent. Crystallinity both decreases gas permeability and moisture sensitivity. An example of homoxylan which can be used according to the invention is glucuronoxylan. Examples of heteroxylans which can be used according to the invention are arabinoxylan, glucuronoarabinoxylan and arabinoglucuronoxylan.

"Pectin" refers to a high molar mass hetero-polysaccharide with at least 65 wt % of $\alpha$-(1→4)-linked D-galacturonic acid-based units. These units may be present as free acid, salt (sodium, potassium calcium, ammonium), naturally esterified with methanol, or as acid amid in amidated pectins. Furthermore, a range of neutral sugars such as L-rhamnose, D-galactose, L-arabinose, D-xylose, and small amounts of others may be part of the polymer chain. Pectins exhibit a very complex, non-random structure with linear blocks of homo-poly(galacturonic acid) and with highly branched blocks. Pectins can differ by the degree of esterification of the carboxy groups of the galacturonic acid, which is in general in the range of 20-80%. Pectins with more than 50% esterification are designated as high-esterified (HM, high methoxylated) and distinguished from low-esterified pectins (LM, low methoxylated) with less than 50% ester groups. The molar mass depends on the pectin source and processing, and is reported to be in the range of $10^4$ to $2\times10^5$ g/mol. A small portion of the hydroxyl groups may be acetylated in pectins from sugar beet, but not in those from citrus fruits.

"Chitin" is a water-insoluble polysaccharide made from chains of modified glucose, i.e., N-acetyl-D-glucosamine and D-glucosamine. Chitin is found in the exoskeletons of insects, the cell walls of fungi, and certain hard structures in invertebrates and fish. Chitin has the general structure:

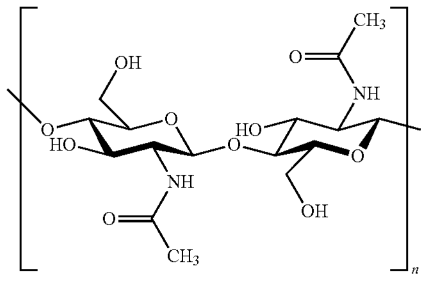

wherein n is typically 100 to 8000.

"Chitosan" is a copolymer of the same two monomer units as chitin, but the preponderance of monomer units are D-glucosamine residues. Since the D-glucosamine residues bear a basic amino function, they readily form salts with acids. Many of these salts are water soluble. Treatment of chitin with a relatively concentrated acidic solution at elevated temperature converts N-acetyl-D-glucosamine residues into D-glucosamine residues and thereby converts chitin into chitosan. There is a continuum of compositions possible between pure poly-N-acetyl-D-glucosamine and pure poly-D-glucosamine. These compositions are all within the skill of the art to prepare and are all suitable for use in the preparation of a biodegradable microcapsule described herein.

As used herein, a "gum" is a long chain polysaccharide that is capable of causing a significant increase in a solution's viscosity, even at small concentrations. Natural gums have been used in the food industry as thickening agents, gelling agents, emulsifying agents and stabilizers. Gums may be obtained from seaweed (e.g., alginate, furcellaran or carrageenan), plant/fungal sources (e.g., gum Arabic, gum tragacanth, guar gum, locust bean gum, psyllium or pullulan) or by bacterial fermentation (e.g., xanthan gum or gellan gum). Gums of use in this invention may be charged or uncharged (i.e., neutral).

Polygalactomannan gums are polysaccharides composed principally of galactose and mannose units and are usually found in the endosperm of leguminous seeds, such as guar, locust bean, honey locust, flame tree, and the like. Cationic polygalactomannans are especially suitable for use in the invention and include guars, and derivatives thereof such as hydroxyalkyl guars (for example hydroxyethyl guars or hydroxypropyl guars), that have been cationically modified by chemical reaction with one or more derivatizing agents. Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted. Preferred cationic polygalactomannans for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl)trimethylammonium chloride.

Cationic polygalactomannans for use in the invention (preferably guar hydroxypropyltrimethylammonium chlorides) generally have an average molecular weight (as determined by size exclusion chromatography) in the range 500,000 g/mol to 3 million g/mol, more preferably 800,000 g/mol to 2.5 million g/mol.

Cationic polygalactomannans for use in the invention (preferably guar hydroxypropyltrimethylammonium chlorides) generally have a charge density ranging from 0.5 to 1.8 meq/g. The cationic charge density of the polymer is suitably determined via the Kjeldahl method as described in the US Pharmacopoeia under chemical tests for nitrogen determination. Specific examples of preferred cationic polygalactomannans are guar hydroxypropyltrimonium chlorides having a cationic charge density from 0.5 meq/g to 1.1 meq/g. Also suitable are mixtures of cationic polygalactomannans in which one has a cationic charge density from 0.5 meq/g to 1.1 meq/g, and one has a cationic charge density from 1.1 to 1.8 meq/g. Specific examples of preferred mixtures of cationic polygalactomannans are mixtures of guar hydroxypropyltrimonium chlorides in which one has a cationic charge density from 0.5 to 1.1 meq/g, and one has a cationic charge density from 1.1 to 1.8 meq per gram.

A particularly suitable polygalactomannan is guar gum. Natural guar gum, also called guaran, is a galactomannan polysaccharide extracted from guar beans that has thickening and stabilizing properties useful in the food, feed and industrial applications. The guar seeds are mechanically dehusked, hydrated, milled and screened according to application. It is typically produced as a free-flowing, off-white powder.

The guar gum thus obtained is composed mostly of a galactomannan which is essentially a straight chain mannan (a polymer of mannose) with single membered galactose branches. The mannose units are linked in a 1-4-3-glycosidic linkage and the galactose branching takes place by means of a 1-6 linkage on alternate mannose units. The ratio of galactose to mannose in the guar polymer is therefore one to two.

The guar gum may be a neutral (non-ionic) guar gum or cationic guar gum, e.g., containing a hydroxypropyltrimonium group. The structure of this type of cationic guar gum is:

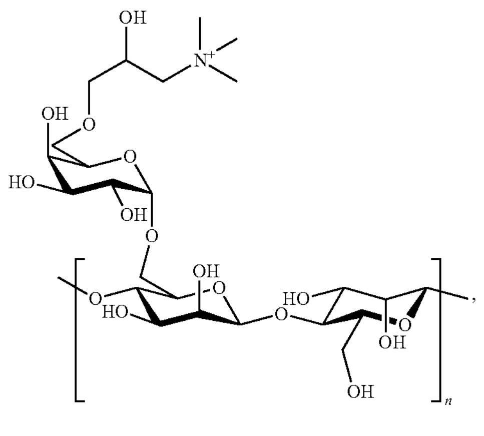

wherein n is an integer from 1 to 1,000,000 with an upper limit of 1,000,000, 500,000, 250,000, 100,000, 50,000, 25,000, 10,000, 5,000, 2,500, 1,000, 500, 250, 100, 50, 25, and 10, and a lower limit of 1, 2, 5, 10, 25, 50, 100, 250, 500, and 1000. In some embodiments, the guar is hydrolyzed to form low molecular weight guar.

Cationic guar gums are commercially available and include, but are not limited to, Activsoft C-13, Activisoft C-14, and Activisoft C-17, from Innospec; Guar 13S, Guar 14S, Guar 15S, Guarquat C130KC, Guarquat C140KC, Guarquat L80KC, SPI-6520, SPI-7006, SPI-7010, SPI-7010LV, Vida-Care GHTC 03, Vida-Care GHTC 04, iQUAT guar 14S, HV-101, iQUAT guar clear NT500, as well as those sold under the trademarks N-HANCE® 3000, N-HANCE® 3196, N-HANCE® 4572, N-HANCE® C261N, N-HANCE® BF13, N-HANCE® CG13, N-HANCEO 3215, N-HANCE® HPCG 1000, N-HANCE® CGC 45, Aquacat™ PF618, Aquacat™ CG518, (all of which are manufactured by Ashland); GuarSafe® JK-14; 1DEHYQUART® N, DEHYQUART® TC, and DEHYQUARTO HP, from BASF; ECOPOLO-13, ECOPOL®-14, ECOPOL®-17, ECOPOL®-261, by Economy Polymer & Chemicals; JAGUAR® C-14-S, JAGUAR® C-13-S, JAGUAR® C-17, JAGUAR® C-500, JAGUAR® C-300, JAGUAR® Excel, JAGUAR® Optima, TIC Pretested® TICOLV and the like. Similarly, neutral or non-ionic guar gums are commercially available and sold, e.g., under the trademarks JAGUAR® HP-8 COS from Solvay.

Gum Arabic is a complex mixture of arabinogalactan oligosaccharides, polysaccharides, and glyco-proteins. It is a branched neutral or slightly acidic substance. The chemical composition and the composition of the mixture can vary with the source, climate, season, age of trees, rainfall, time of exudation, and other factors. The backbone has been identified to be composed of β-(1→3)-linked D-galactopyranosyl units. The side chains are composed of two to five β-(1→3)-linked D-galactopyranosyl units, joined to the main chain by 1,6-linkages. Both the main and the side chain contain units of α-L-arabinofuranosyl, α-L-rhamnopyranosyl, β-D-glucuronopyranosyl, and 4-O-methyl-α-D-glucuronopyranosyl, the latter two of which usually occur preferably as end-units. Depending on the source, the glycan components of gum Arabic contain a greater proportion of L-arabinose relative to D-galactose (Acacia seyal) or D-galactose relative to L-arabinose (Acacia senegal). The gum from Acacia seyal also contains significantly more 4-O-methyl-D-glucuronic acid but less L-rhamnose and unsubstituted D-glucuronic acid than that from Acacia senegal.

Polyphenolic Biopolymers. A polyphenolic biopolymer refers to an aromatic or polyaromatic compound having at least two hydroxy groups. Examples of polyphenolic biopolymers include, but are not limited to, lignin, tannins, tannic acid, humic acid, or combinations thereof. In particular embodiments, the polyphenolic biopolymer used as a wall polymer in the preparation of a microcapsule of this invention is lignin. Lignin is a complex chemical compound commonly derived from wood and is an integral part of the cell walls of plants. Lignin is a large, cross-linked, racemic macromolecule with a molecular mass in excess of 10,000 g/mol and is relatively hydrophobic and aromatic in nature. Lignin has several unique properties as a biopolymer, including its heterogeneity in lacking a defined primary structure. The degree of polymerization of lignin in nature is difficult to measure, since it is fragmented during extraction and is composed of various types of substructures which appear to repeat in a haphazard manner. Suitable lignin material of use in this invention can include, but is not limited to, lignin in its native or natural state, i.e., non-modified or unaltered lignin, lignosulfonates, or any combination or mixture thereof. Suitable lignosulfonates can include, but are not limited to, ammonium lignosulfonate, sodium lignosulfonate, calcium lignosulfonate, magnesium lignosulfonate, or any combination or mixture thereof.

Typically, a biopolymer (i.e., one or more polypeptides, polysaccharides, polyphenolic compounds, or a combination thereof) constitutes 0.5% to 99% (e.g., 1% to 95%, 15% to 90%, 10% to 50%, 15% to 40%, 20% to 85%, 25% to 80%, 30% to 75%, 45%, 55%, 65%, and 75%) by dry weight of the microcapsule. When the microcapsule is incorporated in a microcapsule composition, the amount of the biopolymer varies from 5% to 50%, preferably from 10% to 45%, more preferably from 20% to 35%, all based on the total dry weight of the capsule composition. Further, when more than one biopolymer is used as the microcapsule wall material, the same or different amounts of each biopolymer may be used. For example, when HEC is used in combination with other polysaccharides or sugar alcohols, the content of HEC can be at the low end of the range, e.g., 10% to 50% and 15% to 40%. When used in combination with hydroxypropyl cellulose (HPC), the ratio between HEC and HPC can be 1:9 to 9:1 (e.g., 2:8 to 8:2, 3:7 to 7:3, 4:6 to 6:4, 1:2, 1:3, 4:1, and 5:1).

C. Cross-Linking Agents

To achieve the desired performance characteristics (i.e., active material retention and controlled release), the biopolymer is cross-linked with one or more cross-linking agents. As used herein, a "cross-link" is a bond, atom, or group linking the chains of atoms in a biopolymer. In some embodiments, one or more of the following cross-links are used in the formation of a biodegradable microcapsule: imine, amine, aminoalkylamine, oxime, hydroxylamine, hydrazine, hydrazone, azine, hydrazide-hydrazone, amide, hydrazide, semicarbazide, semicarbazone, thiosemicarbazide, thiocarbazone, disulfide, acetal, hemiacetal, thiohemiacetal, α-keto-alkylthioalkyl, urethane, urea, Michael adduct or α-keto-alkylaminoalkyl cross-linkage.

A "cross-linking agent" or "cross-linker" refers to a substance that induces or forms a cross-link. A cross-linking agent of use in this invention may be monofunctional (containing only one reactive group) or multifunctional (containing more than one reactive group). Moreover, in some embodiments, the cross-linking agent may provide one type of linkage, whereas in other embodiments, the cross-linking agent may provide for more than one type of linkage. Accordingly, in some embodiments, the cross-linking agent is heterofunctional, e.g., heterobifunctional. Examples of cross-linking agents of use in this invention include, but are not limited to, aldehydes, epoxy compounds, polyvalent metal cations, polyphenols, maleimides, sulfides, phenolic oxides, hydrazides, isocyanates, isothiocyanates, N-hydroxysulfosuccinimide derivatives, carbodiimide derivatives, sugars, polyols such as sugar alcohols, amines, enzymes, or a combination thereof.

Aldehyde cross-linkers have one or more, preferably two or more, formyl groups (—CHO). In certain embodiments, the aldehyde cross-linker is a multifunctional aldehyde. Suitable multifunctional aldehydes include glutaraldehyde, glyoxal, di-aldehyde starch, malondialdehyde, succinic dialdehyde, 1,3-propane dialdehyde, 1,4-butane dialdehyde, 1,5-pentane dialdehyde, and 1,6-hexane; as well as compounds such as glyoxyl trimer and paraformaldehyde, bis (dimethyl) acetal, bis(diethyl) acetal, polymeric dialdehydes, such as oxidized starch.

As a cross-linker, an "epoxy compound" contains a hydroxyl group or ether bond, either in its original form or having such a group or bond formed upon undergoing the cross-linking reaction. Examples of suitable epoxy, also referred to as polyglycidyl ether, cross-linkers include, e.g., 1,4-butanediol diglycidyl ether (BDDE), ethylene glycol diglycidyl ether (EGDGE), 1,6-hexanediol diglycigyl ether, polyethylene glycol diglycidyl ether, propyleneglycol diglycidyl ether, polypropylene glycol diglycidyl ether, polytetramethylene glycol digylcidyl ether, neopentyl glycol digylcidyl ether, polyglycerol polyglycidyl ether, diglycerol polyglycidyl ether, glycerol polyglycidyl ether, hexanediolglycidyl ether, trimethylolpropane polyglycidyl ether, pentaerythritol polyglycidyl ether, sorbitol polyglycidyl ether, phthalic acid diglycidyl ester, adipinic acid diglycidyl ether, glycidol, or a combination thereof.

A polyvalent metal cation of use as a cross-linker of this invention 4s derived preferably from singly or multiply charged cations, the singly charged in particular from alkali metals such as potassium, sodium, lithium. Preferred doubly charged cations are derived from zinc, beryllium, alkaline earth metals such as magnesium, calcium, strontium. Further cations applicable in the invention with higher charge are cations from aluminium, iron, chromium, manganese, titanium, zirconium and other transition metals as well as double salts of such cations or mixtures of the named salts. The use of aluminium salts and alums and various hydrates thereof include, e.g., $AlCl_3 \times 6\ H_2O$, $NaAl(SO_4)_2 \times 12\ H_2O$, $KAl(SO_4)_2 \times 12\ H_2O$ or $Al_2\ (SO_4)_3 \times 14\text{-}18H_2O$.

Polyphenol cross-linkers of use in this invention have at least two or more hydroxyphenyl groups. Examples of suitable polyphenol cross-linkers include, but are not limited to, a flavonoid, isoflavonoid, neoflavonoid, gallotannin, ellagotannin, catechol, DL-3,4-dihydroxyphenylalaline, catecholamine, phloroglucinol, a phenolic acid such as gallic acid or tannic acid, phenolic ester, phenolic heteroside, curcumin, polyhydroxylated coumarin, polyhydroxylated lignan, neolignan, a poly-resorcinol or a combination thereof. In certain embodiments, the polyphenol cross-linker is a phenolic acid having a 3,4,5-trihydroxyphenyl group or 3,4-dihydroxyphenyl group. A preferred polyphenol is tannic acid.

As used herein, the term "maleimide" refers to a compound having a maleimide group:

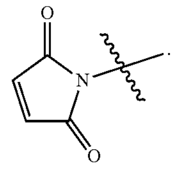 [SMILES: *N1C(=O)C=CC1=O]

A bismaleimide refers to a compound having two maleimide groups, where the two maleimide groups are bonded by the nitrogen atoms via a linker. Examples of such crosslinkers carrying maleimide groups are succinimidyl m-maleimidobenzoate (SMB), sulfosuccinimidyl m-maleimidobenzoate (sulfo-SMB), succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), sulfosuccinimidyl 4-(p-maleimidophenyl)butyrate (sulfo-SMPB), bis-maleimidohexane (BMH), N-(4-diazophenyl)maleimide and N-(β-diazophenylethyl) maleimide.

The terms "isocyanate," "polyfunctional isocyanate," "multifunctional isocyanate," and "polyisocyanate" are used interchangeably herein and refer to a compound having two or more isocyanate (—NCO) groups. Polyisocyanates can be aromatic, aliphatic, linear, branched, or cyclic. In some embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanate has the generic structure shown below, and includes structural isomers thereof

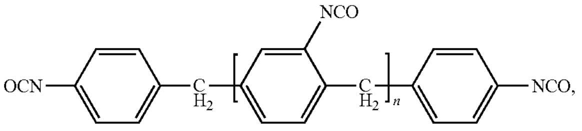

wherein n can vary from zero to a desired number (e.g., 0-50, 0-20, 0-10, and 0-6). Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include those sold under the trademarks LUPRANATE® M20 (chemical name: polymeric methylene diphenyl diisocyanate, i.e., "PMDI", containing isocyanate group "NCO" at 31.5 wt %; BASF), where the average n is 0.7; PAPI® 27 (Dow Chemical; PMDI having an average molecular weight of 340 and containing NCO at 31.4 wt %) where the average n is 0.7; MONDUR MR® (Covestro, Pittsburgh, PA; PMDI containing NCO at 31 wt % or greater) where the average n is 0.8; MONDUR MR® Light (Covestro; PMDI containing NCO at 31.8 wt %) where the average n is 0.8; MONDUR® 489 (Covestro; PMDI containing NCO at 30-31.4 wt %) where the average n is 1; poly[(phenylisocyanate)-co-formaldehyde] (Aldrich Chemical, Milwaukee, WI), and other isocyanate monomers sold under the trademarks DESMODUR® N3200 (Covestro; poly(hexamethylene diisocyanate), and TAKENATE® D110-N (Mitsui Chemicals Corporation; trimethylol propane-adduct of xylylene diisocyanate containing NCO at 11.5 wt %), DESMODUR® L75 (Covestro; a polyisocyanate based on toluene diisocyanate), and DESMODURO IL (Covestro; another polyisocyanate based on toluene diisocyanate).

The general structure of commercially available polyisocyanates of the invention is shown below:

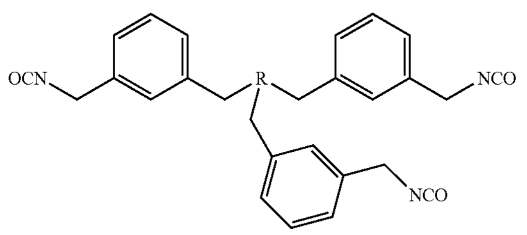

or its structural isomer, wherein R can be a $C_1$-$C_{10}$ alkyl, $C_1$-$C_{10}$ ester, or an isocyanurate. Representative polyisocyanates having this structure are sold under the trademarks TAKENATE® D-110N (Mitsui), DESMODURM L75 (Covestro), and DESMODUR® IL (Covestro).

Polyisocyanate sold under the trademark TAKENATE® D-110N and other polyisocyanates are commercially available, typically in an ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

By way of illustration, a trimethylol propane-adduct of xylylene diisocyanate solution in ethyl acetate, which is sold under the trademark TAKENATE® D-110N, is combined with benzyl benzoate and vacuum distilled to remove ethyl acetate to obtain a polyisocyanate solution containing about 59% of the trimethylol propane-adduct of xylylene diisocyanate solution and 41% of benzyl benzoate. This polyisocyanate solution has a flash point of at least 60° C. This polyisocyanate solution in benzyl benzoate, together with polyvinylpyrrolidone/polyquaternium 11 or sulfonated polystyrene/carboxymethyl cellulose can be used to prepare the microcapsule composition of this invention.

Other examples of the aromatic polyisocyanate include 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenylperfluoroethane, phthalic acid bisisocyanatoethyl ester, also polyisocyanates with reactive halogen atoms, such as 1-chloromethylphenyl 2,4-diisocyanate, 1-bromomethyl-phenyl 2,6-diisocyanate, and 3,3-bischloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include those sold under the trademarks BAYHYDUR® N304 and BAYHYDUR® N305, which are aliphatic water-dispersible polyisocyanates based on hexamethylene diisocyanate; DESMODUR® N3600, DESMODUR® N3700, and DESMODUR® N3900, which are low viscosity, polyfunctional aliphatic polyisocyanates based on hexamethylene diisocyanate; and DESMODUR® 3600 and DESMODUR® N100 which are aliphatic polyisocyanates based on hexamethylene diisocyanate, each of which is available from Covestro (Pittsburgh, PA). More examples include 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The weight average molecular weight of certain polyisocyanates useful in this invention varies from 250 Da to 1000 Da and preferable from 275 Da to 500 Da.

In some embodiments, the polyfunctional isocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is as a cross-linker in the preparation of the capsule wall material. More examples of suitable polyisocyanates can be found in WO 2004/054362 and WO 2017/192648.

During the process of preparing the microcapsule composition of this invention, polyisocyanate can be added to the aqueous phase or to the oil phase.

Amines include naturally occurring amino acids such as lysine, histidine, arginine, nontoxic derivatives or family members of lysine, histidine or arginine and mixtures thereof as well was guanidine amines and guanidine salts. Exemplary guanidine amines and guanidine salts include, but are not limited to, 1,3-diaminoguanidine monohydrochloride, 1,1-dimethylbiguanide hydrochloride, guanidine carbonate and guanidine hydrochloride. In some embodiments, the amine is lysine. In other embodiments, the amine is guanidine carbonate.

Diacids of use as cross-linking agents include, e.g., ethanedioic acid, malonic acid, succinnic acid, glutaric acid, adipic acid, pimelic acid, suberic acid, azelaic acid, sebacic acid, nonanedioic acid, malic acid, maleic acid, dimethyl glutaric acid, fumaric acid, tartaric acid, citric acid, lactic acid and salicylic acid.

Polyols such as sugar alcohols can also be used as cross-linking agents. See polyols described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof.

Other polyols of use as cross-linkers include, for example, ethyleneglycol; polyethyleneglycols such as diethyleneglycol, triethyleneglycol and tetraethyleneglycol; propyleneglycol; polypropyleneglycols such as dipropyleneglycol, tripropyleneglycol or tetrapropyleneglycol; 1,3-butanediol; 1,4-butanediol; 1,5-pentanediol; 2,4-pentanediol; 1,6-hexanediol; 2,5-hexanediol; glycerin; polyglycerin; trimethylolpropane; polyoxypropylene; oxyethylene-oxypropylene-block copolymer; sorbitan-fatty acid esters; polyoxyethylenesorbitan-fatty acid esters; polyvinylalcohol and sorbitol; aminoalcohols for example ethanolamine, diethanolamine, triethanolamine or propanolamine; polyamine compounds, for example ethylenediamine, diethylenetriamine, triethylenetetraamine, tetraethylenepentaamine or pentaethylenehexaamine; polyaziridine compounds such as 2,2-bishydroxymethylbutanol-tris[3-(1-aziridinyl)propionate], 1,6-hexamethylenediethyleneurea and diphenylmethane-bis-4,4'-N,N'-diethyleneurea; halogen epoxides for example epichloro- and epibromohydrin and α-methylepichlorohydrin; alkylenecarbonates such as 1,3-dioxolane-2-one (ethylene carbonate), 4-methyl-1,3-dioxolane-2-one (propylene carbonate), 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxolane-2-one, poly-1,3-dioxolane-2-one; and polyquaternary amines such as condensation products from dimethylamines and epichlorohydrin.

Enzymes of use as cross-linking agents may catalyze protein-protein, polysaccharide-polysaccharide, protein-polysaccharide, polyphenol-polyphenol, protein-polyphenol or polyphenol-polysaccharide linkages. In certain embodiments, the cross-linking enzyme can be, for example, a transglutaminase, a tyrosinase, a lipoxygenase, a protein disulfide reductase, a protein disulfide isomerase, a sulfhydryl oxidase, a peroxidase, a hexose oxidase, a lysyl oxidase, or an amine oxidase. As an alternative to enzymes, chemicals that promote formation of inter-molecular disulfide cross-links between the proteins can be used. In some embodiments, the chemicals are proteins (e.g., thioredoxin, glutaredoxin).

In some embodiments, a transglutaminase is used as a cross-linking agent. Transglutaminases catalyze the linkage of γ-carboxamide group of a glutaminyl residue to the ε-amino of a lysyl residue to form a γ-carboxyl-ε-amino-linkage. Transglutaminases have a broad occurrence in living systems and can be obtained from microorganisms belonging to the genus Streptoverticillium, or from *Bacillus subtilis*, from various Actinomycetes and Myxomycetes, from plants, fish and from mammalian sources, including the blood clotting protein activated Factor XIII.

As a further alternative, biopolymers including aryl azides (e.g., phenyl azides, hydroxyphenyl azides, and nitrophenyl azides) or diazirines (azipentanoates) can be photo cross-linked. Photo crossing generally includes UV crossing linking at a wavelength in the range of 250 nm to 460 nm (e.g., 250 nm to 350 nm, 265 nm to 275 nm, 300 nm to 460 nm, or 330 nm to 370 nm). Photo cross-linking may be conducted alone or in combination with one or more of the above-referenced chemical cross-linking agents.

The total amount of cross-linking agent used in the preparation of a biodegradable microcapsule of this invention can vary and be dependent upon the cross-linker or combination of cross-linkers used. In general, the amount of cross-linker present is in the range of 0.1% to 50% (e.g., 0.3% to 40%, 0.4% to 35%, 0.5% to 30%, 1% to 25%, 2% to 25%, and 5% to 20%) by dry weight of the microcapsule. When the microcapsule is incorporated in a microcapsule composition, the amount of the cross-linker varies from 0.1% to 20%, preferably from 0.1% to 15%, more preferably from 0.2% to 10%, and even more preferably from 1.5% to 3.5%, all based on the total dry weight of the capsule composition. As would be appreciated by the skilled artisan, enzymes and photo cross-linking may be removed from the microcapsule composition and therefore may or may not contribute to the dry weight of the microcapsule.

While a single cross-linking agent may be used in the preparation of a microcapsule of this invention, it has been found that a combination of cross-linking agents can increase the cross-link density as compared to when a single cross-linking agent is used. Accordingly, in certain embodiments, two or more, three or more, or four or more cross-linking agents are used to improve cross-linking density and diversity. In particular embodiments, at least two cross-linking agents are used. Further, it has been observed that significantly lower levels of isocyanate can be used, without a significant impact on microcapsule performance, when the isocyanate is augmented with at least one other cross-linker.

Accordingly, in some embodiments, a polyisocyanate is used in combination with a second cross-linking agent. In particular embodiments, a polyisocyanate is used in combination with a polyphenol such as tannic acid and optionally an aldehyde such as glutaraldehyde.

In instances where two more cross-linkers are used, the amount of each cross-linker may be the same or different. For example, when a polyisocyanate is used, the content of the polyisocyanate can vary from 0.1% to 40% (e.g., 0.4% to 35%, 0.5% to 30%, 1% to 25%, 2% to 25%, and 5% to 20%) by dry weight of the microcapsule. Further, when a polyphenol (e.g., tannic acid) is used, the polyphenol may be used at a level of 0.1% to 35% (e.g., 0.05% to 10% and 0.1% to 5%) by dry weight of the microcapsule. Similarly, when an aldehyde (e.g., glutaraldehyde) is used as a cross-linker, the aldehyde may be used at a level of 0.01% to 10% (e.g., 0.05% to 8% and 0.1% to 5%) by dry weight of the microcapsule.

As used in this invention, the weight ratio between the biopolymer and cross-linking agent is in the range of 600:1 to 3:100 (preferably 60:1 to 3:10, and more preferably 12:1 to 3:10).

D. Active Material

The core of the biodegradable core-shell microcapsule of this invention includes at least one active material. In certain embodiments, the microcapsule includes at least two, three, four or more active materials in the core. The active material can be a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or a combination thereof. Individual active materials that can be encapsulated include those listed in WO 2016/049456, pages 38-50.

When the active material is a fragrance, it is preferred that fragrance ingredients of the fragrance having a ClogP of 0.5 to 15 are employed. For instance, the ingredients having a ClogP value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance. It is preferred that a fragrance having a weight-averaged ClogP of 2.5 and greater (e.g., 3 or greater, 2.5 to 7, and 2.5 to 5) is employed. The weight-averaged ClogP is calculated as follows:

$$C \log P=\{\mathrm{Sum}[(Wi)(C \log P)i]\}/\{\mathrm{Sum}\, Wi\},$$

in which Wi is the weight fraction of each fragrance ingredient and (ClogP)i is the ClogP of that fragrance ingredient.

As an illustration, it is preferred that greater than 60 wt % (preferably greater than 80 wt % and more preferably greater than 90 wt %) of the fragrance ingredients have ClogP values of greater than 2 (preferably greater than 3.3, more preferably greater than 4, and even more preferably greater than 4.5).

It should be noted that while ClogP and aqueous solubility are roughly correlated, there are materials with similar ClogP yet very different aqueous solubility. ClogP is the traditionally used measure of hydrophilicity in perfumery. However, the nature of the fragrance materials may be further refined in that greater than 60 weight percent of the fragrance materials have a ClogP of greater than 3.3 and a water solubility of less than 350 ppm. In another preferred embodiment, more than 80 weight percent of the fragrance materials have a ClogP of greater than 4.0 and a water solubility of less than 100 ppm. In a more preferred embodiment, more than 90% of the fragrance materials have a ClogP value of greater than about 4.5 and a water solubility of less than 20 ppm. In any case, selection of materials having a lower water solubility is preferred.

Ideally, the microencapsulated active material has a low interfacial tension. For example, a suitable active material can have an interfacial tension of less than about 20, less than about 15, less than about 11, less than about 9, less than about 7, less than about 5, less than about 3, less than about 2, less than about 1, or less than about 0.5 dynes/cm. In other examples, the active material can have an interfacial tension of from about 0.1 to about 20, from about 1 to about 15, from about 2 to about 9, from about 3 to about 9, from about 4 to about 9, from about 5 to about 9, from about 2 to about 7, from about 0.1 to 5, from about 0.3 to 2, or from about 0.5 to 1 dynes/cm.

Those with skill in the art will appreciate that many fragrances can be created employing various solvents and fragrance ingredients. The use of a relatively low to intermediate ClogP fragrance ingredients will result in fragrances that are suitable for encapsulation. These fragrances are generally water-insoluble, to be delivered through the microcapsule compositions of this invention onto consumer products in different stages such as damp and dry fabric. Without encapsulation, the free fragrances would normally have evaporated or dissolved in water during use, e.g., wash. Though high ClogP materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

High performing, high impact fragrances are envisaged. One class of high performing fragrances is described in WO 2018/071897. These fragrances have a high intensity accord containing (i) at least 7 wt % (e.g., 7 wt % to 95 wt %) of Class 1 fragrance ingredients, (ii) 5 wt % to 95 wt % (e.g., 5 wt % to 80 wt %, 10 wt % to 80 wt %, and 10 wt % to 70 wt %) of Class 2 fragrance ingredients, and (iii) 0 wt % to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less. In some embodiments, the sum of the Class 1 fragrance ingredients, the Class 2 fragrance ingredients, and the Class 3 fragrance ingredients is 100%. In other embodiments, the sum of Class 1 and Class 2 ingredients is 20 wt % to 100 wt %. Other high impact fragrances suitable for use in this invention are those described in WO 1999/065458, U.S. Pat. No. 9,222,055, US 2005/0003975, and WO 1997/034987.

In some embodiments, the amount of encapsulated active material is from 5% to 95% (e.g., 10% to 90%, 15% to 80%, and 20% to 60%) by dry weight of the microcapsule composition. In particular embodiments, the amount of encapsulated material is at least 10% by dry weight of the microcapsule composition. The amount of the microcapsule wall is from 0.5% to 30% (e.g., 1% to 25%, 2 to 20% and 5 to 15%) also by dry weight of the microcapsule composition. In other embodiments, the amount of the encapsulated active material is from 15% to 99.5% (e.g., 20% to 98% and 30% to 90%) by weight of the microcapsule composition, and the amount of the capsule wall is from 0.5% to 85% (e.g., 2 to 50% and 5 to 40%) by weight of the microcapsule composition. In certain embodiments, at least 40%, 50%, 60%, or 70% of the active material, in particular a flavor or fragrance, included in the core of the microcapsule is also biodegradable.

E. Additional Components of the Microcapsule Composition

In addition to the active materials, the present invention also contemplates the incorporation of additional components including solvents and core modifier materials in the core encapsulated by the microcapsule wall. Other components include solubility modifiers, density modifiers, stabilizers, viscosity modifiers, pH modifiers, deposition aids, capsule formation aids, catalysts, processing aids or any combination thereof. These components can be present in the wall or core of the capsules, or outside the capsules in the microcapsule composition to improve solubility, stability, deposition, capsule formation, and the like. Further, the additional components may be added after and/or during the preparation of the microcapsule composition of this invention.

The one or more additional components may be added in the amount of 0.01% to 40% (e.g., 0.5% to 30%) by dry weight of the microcapsule composition depending on the component included.

Solvents. A suitable solvent of use in the microcapsule composition include, e.g., isopropanol, ethyl acetate, acetic acid, ethanolamine, about caprylic/capric triglyceride, and the like, or any combination thereof.

Capsule Formation Aids. The microcapsule composition may be prepared in the presence of a capsule formation aid, which can be a surfactant or dispersant. Capsule formation aids also improve the performance of the microcapsule composition. Performance is measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener or detergent. The post-rub phase is after the capsules have been deposited and are broken by friction or other mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and combinations thereof. The concentration of the capsule formation aid (e.g., the surfactant and dispersant) varies from 0.1% to 10% (e.g., 0.2% to 10%, 0.5% to 8%, 0.5% to 5%, and 1% to 2%) by dry weight of the microcapsule composition.

Commercially available surfactants include, but are not limited to, sulfonated naphthalene-formaldehyde condensates sold under the trademark MORWET® D425 (naphthalene sulfonate, Akzo Nobel, Fort Worth, TX); partially hydrolyzed polyvinyl alcohols sold under the trademark MOWIOL®, e.g., MOWIOL® 3-83 (Air Products); ethylene oxide-propylene oxide block copolymers or poloxamers sold under the trademarks PLURONIC®, SYNPERONIC® or PLURACARE® (BASF); sulfonated polystyrenes sold under the trademark FLEXAN® II (Akzo Nobel); ethylene-maleic anhydride polymers sold under the trademark ZEMAC® (Vertellus Specialties Inc.); and Polyquaternium series such as Polyquaternium 11 ("PQ11;" a copolymer of vinyl pyrrolidone and quaternized dimethylaminoethyl methacrylate; sold under the trademark LUVIQUAT® PQ11 AT 1 by BASF).

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of these surfactants include cetyl trimethyl ammonium chloride (CTAC); poloxamers sold under the trademarks PLURONIC® (e.g., PLURONIC® F127), PLURAFAC® (e.g., PLURAFAC® F127); a saponin sold under the trademark Q-NATURALE® (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. In other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. A commercially available alkylnaphthalenesulfonate formaldehyde condensates is sold under the trademark MORWET® D-425, which is a sodium salt of naphthalene sulfonate condensate by Akzo Nobel (Fort Worth, TX).

Processing Aids. Processing aids include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polysaccharides, such as starch, modified starch, dextrin, maltodextrin, and cellulose derivatives, and their quaternized forms; natural gums such as alginate esters, carrageenan, xanthans, agar-agar, and natural gums such as gum Arabic, gum tragacanth and gum karaya, guar gums and quaternized guar gums; pectins; pectic acid; gelatin; protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid) copolymer, poly(alkyleneoxide), poly(vinyl-methylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

Catalysts. Sometimes, a catalyst is added to facilitate the formation of a capsule wall. Examples include metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N, N-dimethylaminoethanol, N, N-dimethylcyclohexylamine, bis-(2-dimethylaminoethyl) ether, N,N-dimethylacetylamine, stannous octoate, and dibutyltin dilaurate.

Deposition Aids. Deposition aids facilitate the adherence or deposition of a microcapsule of this invention onto a surface (e.g., hair, skin, fiber, furniture, or floor). An exemplary deposition aid useful in the microcapsule composition of this invention is a copolymer of acrylamide and acrylamidopropyltrimonium chloride. The copolymer generally has an average molecular weight (e.g., weight average molecular mass determined by size exclusion chromatography) of 2,000 Da to 10,000,000 Da with a lower limit of 2,000 Da, 5,000 Da, 10,000 Da, 20,000 Da, 50,000 Da, 100,000 Da, 250,000 Da, 500,000 Da, or 800,000 Da and an upper limit of 10,000,000 Da, 5,000,000 Da, 2,000,000 Da, 1,000,000 Da, or 500,000 Daltons Da (e.g., 500,000 Da to 2,000,000 Da and 800,000 Da to 1,500,000 Da). The charge density of the copolymer ranges from 1 meq/g to 2.5 meq/g, preferably from 1.5 to 2.2 meq/g. The copolymer of acrylamidopropyltrimonium chloride and acrylamide is commercially available from several vendors, e.g., sold under the trademark N-HANCE® SP-100 (Ashland) or SALCARE® SC60 (Ciba).

Other suitable deposition aids include anionically, cationically, nonionically, or amphoteric water-soluble polymers. Suitable deposition aids include polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, a methacrylamidopropyltrimonium chloride/acrylamide copolymer, copolymer of acrylamide and acrylamidopropyltrimonium chloride, 3-acrylamidopropyl trimethylammonium polymer or its copolymer, diallyldimethylammoniumchloride polymer and its copolymer, a polysaccharide with saccharide unit functionalized with hydroxypropyl trimmonium, and combinations thereof. More examples of suitable deposition aids are described in WO 2016/049456, pages 13-27; US 2013/0330292; US 2013/0337023; and US 2014/0017278.

Additional deposition aids include, e.g., the cationic polymers described in WO 2016/032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g). The cationic polymers are composed of structural units that are nonionic, cationic, anionic, or mixtures thereof. In some aspects, the cationic polymer includes from 5 mol % to 60 mol %, or from 15 mol % to 30 mol %, of a nonionic structural unit derived from a monomer selected from the group consisting of (meth) acrylamide, vinyl formamide, N,N-dialkyl acrylamide, N,N-dialkylmethacrylamide, $C_1$-$C_{12}$ alkyl acrylate, $C_1$-$C_{12}$ hydroxyalkyl acrylate, polyalkylene glycol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer includes a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkylltrialkylamminium salts, vinylamine, vinylimine, vinyl imidazole, quaternized vinyl imidazole, diallyl dialkyl ammonium salts, and mixtures thereof. Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methylammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer includes an anionic structural unit at a level of 0.01 mol % to 15 mol %, 0.05 mol % to 10 mol %, 0.1 mol % to 5 mol %, or 1% to 4% of by mass of the cationic polymer. In some aspects, the anionic structural unit is derived from an anionic monomer selected from the group of acrylic acid (AA), methacrylic acid, maleic acid, vinyl sulfonic acid, styrene sulfonic acid, acrylamidopropylmethane sulfonic acid (AMPS) and their salts, and mixtures thereof.

Exemplary cationic polymers include polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by dry weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% by dry weight can be added to the microcapsule composition. The second capsule formation deposition aid can be selected from the above-described deposition aid.

A branched polyethyleneimine and its derivatives can also be coated onto the microcapsule wall to prepare a microcapsule having a positive zeta potential.

Unencapsulated Active Material. One or more non-confined or unencapsulated active materials can also be included post-curing. Such active materials may be the same or different than the encapsulated active material and may be included at a level of from 0.01% to 20%, or more preferably from 2% to 10% by weight of the microcapsule composition (i.e., microcapsule slurry).

The microcapsule composition of this invention can also be combined with one or more other delivery systems such as polymer-assisted delivery compositions (see U.S. Pat. No. 8,187,580), fiber-assisted delivery compositions (US 2010/0305021), cyclodextrin host-guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Furthermore, microcapsules having one or more different characteristics can be combined to provide desirable or tailored release profiles and/or stability. In particular, the microcapsule composition can include a combination of two or more types of microcapsules that differ in their encapsulating wall materials, microcapsule size, amounts of wall materials, the thickness of the wall, the degree of polymerization, the degree of crosslinking, ratios between the wall materials and the active material, core modifiers, scavengers, active materials, cure temperatures, heating rates during the curing, curing times, the rupture force or fracture strength, or a combination thereof. In some embodiments, the microcapsule composition is composed of two, three, four, five, six, seven or more different types of capsules that differ by one or more of the above-referenced characteristics. In particular embodiments, the microcapsule composition is composed of two types of microcapsules, described herein as a first capsule containing a first capsule wall encapsulating a first active material and a second capsule containing a second capsule wall encapsulating a second active material.

The microcapsule composition of this invention optionally has a second, third, fourth, fifth, or sixth microcapsule each formed of an encapsulating polymer selected from the group of a sol-gel polymer (e.g., silica), polyacrylate, polyacrylamide, poly(acrylate-co-acrylamide), polyurea, polyurethane, polypeptide, polysaccharide, polyphenolic polymers, poly(melamine-formaldehyde), poly(urea-formaldehyde), or combinations thereof.

Sol-gel Microcapsules. These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and β-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof. One example of a sol-gel precursor suitable for the purposes of the invention is an alkoxysilane corresponding to the following general formula:

$$(R_1O)(R_2O)M(X)(X'),$$

wherein X can be hydrogen or —$OR_3$; X' can be hydrogen or —$OR_4$; and $R_1$, $R_2$, $R_3$ and $R_4$ independently represent an organic group, more particularly a linear or branched alkyl group, preferably a $C_1$-$C_{12}$ alkyl. M can be Si, Ti, or Zr. A preferred sol/gel precursor is an alkoxysilane corresponding to the following general formula: $(R_1O)(R_2O)Si(X)(X')$, wherein each of X, X', $R_1$, and $R_2$ are defined above.

Particularly preferred compounds are the silicic acid esters such as tetramethyl orthosilicate (TMOS) and tetraethyl orthosilicate (TEOS). A preferred compound is an organofunctional silane sold under the trademark DYNASYLAN® commercially available from Degussa Corporation (Parsippany NJ). Other sol-gel precursors suitable for the purposes of the invention are described, for example, in DE 10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as TMOS, TEOS, etc. are very good solvents for numerous molecules and active ingredients is highly advantageous since it facilitates dissolving the active materials at a high concentration and thus a high loading in the final capsules.

Polyacrylate, Polyacrylamide, and Poly(acrylate-co-acrylamide) Microcapsules. These microcapsules are prepared from corresponding precursors, which form the microcapsule wall. Preferred precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethyloipropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/ acrylamide, 3-acryloyloxy glycol monoacrylate/acrylamide, triacryl formal, triallyl isocyanate, and triallyl isocyanurate.

The monomer is typically polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1,1'-azobis-(cyclohexane-1-carbonitrile), dimethyl 2,2'-azobis(2-methylpropionate), 2,2'-azobis[2-methyl-N-(2-hydroxyethyl) propionamide, sodium persulfate, benzoyl peroxide, and combinations thereof.

Emulsifiers used in the formation of polyacrylate/polyacrylamide/poly(acrylate-co-acrylamide) capsule walls are typically anionic emulsifiers including by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum Arabic, sodium alginate, carboxymethylcellulose, cellulose sulfate and pectin, poly(styrene sulfonate), isobutylene-maleic anhydride copolymer, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy-modified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1% to 40% by weight of all constituents, more preferably from 0.5% to 10%, more preferably 0.5% to 5% by weight.

Aminoplasts. A representative process used for aminoplast encapsulation is disclosed in U.S. Pat. No. 3,516,941 and US 2007/0078071, though it is recognized that many variations with regard to materials and process steps are possible. Polymer systems are well-known in the art and non-limiting examples of these include aminoplast capsules and encapsulated particles as disclosed in GB 2006709 A; the production of micro-capsules having walls composed of styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and Melamine-Formaldehyde Capsules. Urea-formaldehyde and melamine-formaldehyde precondensate capsule shell wall precursors are prepared by means of reacting urea or melamine with formaldehyde where the mole ratio of melamine or urea to formaldehyde is in the range of from 10:1 to 1:6, preferably from 1:2 to 1:5. For the purpose of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or copolymers. Methods for formation of such melamine-formaldehyde and urea-formaldehyde pre-condensates are set forth in U.S. Pat. No. 6,261,483, and Lee, et al. (2002) *J. Microencapsulation* 19:559-569.

Examples of urea-formaldehyde pre-condensates useful in the practice of this invention are sold under the trademarks URAC® 180 and URAC® 186. Examples of melamine-formaldehyde pre-condensates useful in the practice if this invention, include, but are not limited to, are melamine-formaldehyde pre-condensates sold under the trademarks CYMEL® U-60, CYMEL® U-64 and CYMEL® U-65 (Cytec Technology Corp.; Wilmington, DE). It is preferable to use, as the precondensate for cross-linking, the substituted or un-substituted acrylic acid polymer or co-polymer. In practicing this invention, the range of mole ratios of urea-formaldehyde precondensate/melamine-formaldehyde precondensate to substituted/un-substituted acrylic acid polymer/co-polymer is in the range of from 9:1 to 1:9, preferably from 5:1 to 1:5 and most preferably from 2:1 to 1:2.

In one embodiment of the invention, microcapsules with polymer (s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable polyvinylamines are sold under the trademark LUPAMIN® (BASF). The molecular weights of these materials can range from 10,000 Da to 1,000,000 Da.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

Polyurea Capsules. Polyurea capsules can be prepared using multi-functional isocyanates and multi-functional amines. See WO 2004/054362; EP 0148149; EP 0017409 B1; U.S. Pat. Nos. 4,417,916, 4,124,526, 4,285,720, 4,681,806, 5,583,090, 6,340,653, 6,566,306, 6,730,635, 8,299,011, WO 90/08468, and WO 92/13450.

These isocyanates contain two or more isocyanate (—NCO) groups. Suitable isocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

The multi-functional amines contain two or more amine groups including $—NH_2$ and —RNH, R being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl.

Water soluble diamines are one class of useful amines to form a polyurea capsule wall. One class of exemplary amines is of the type:

$H_2N(CH_2)_nNH_2$, where n is ≥1. When n is 1, the amine is methylenediamine. When n is 2, the amine is ethylenediamine and so on. Suitable amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are also useful. Exemplary amines of this class are polyalykylene polyamines of the type:

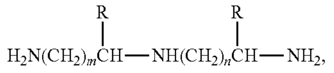

where R equals hydrogen or $—CH_3$, m is 1-5 and n is 1-5, e.g., diethylene triamine, triethylene tetraamine and the like. Exemplary amines of this type include, but are not limited to diethylenetriamine, bis(3-aminopropyl)amine, bis(hexamethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

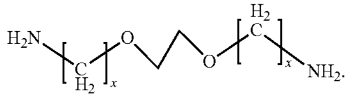

Exemplary polyetheramines include 2,2'-ethylenedioxy) bis(ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, L-arginine, L-lysine monohydrochloride, arginine monohydrochloride and ornithine monohydrochloride.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Other suitable amines include those sold under the trademarks JEFFAMINE® EDR-148 (where x=2), JEFFAMINE® EDR-176 (where x=3) (from Huntsman). Other polyether amines are sold under the trademarks JEFFAMINE® ED Series, and JEFFAMINE® triamines.

The preparation of polyurethane capsules can be carried out by reacting one or more of the above-referenced isocyanates with alcohols including diols or polyols in the presence of a catalyst. Diols or polyols of use in the present invention have a molecular weight in the range of 200-2000 Da. Exemplary diols include, but are not limited to, ethylene glycol, diethylene glycol, propylene glycol, 1,4-butane diol, 1,4-hexane diol, dipropylene glycol, cyclohexyl 1,4-dimethanol, and 1,8-octane diol. Exemplary polyols include, but are not limited to, poly(ethylene glycols), poly(propylene glycols), and poly(tetramethylene glycols). Alcohols having at least two nucleophilic centers are also useful, e.g., hexylene glycol, pentaerythritol, glucose, sorbitol, and 2-aminoethanol.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a microcapsule composition of this invention, is capable of converting to the compound, polymer, or agent and being used in preparing the microcapsule composition. A hydrate refers to the compound, polymer, or agent that contains water. A solvate refers to a complex formed between the compound, polymer, or agent and a suitable solvent.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

F. Microcapsule Properties and Characteristics

The microcapsules of this invention each have a size (in diameter) in the range of 0.1 micron to 1000 microns (e.g., 0.5 micron to 500 microns, 1 micron to 200 microns, 1 micron to 100 microns, and 1 micron to 50 micron) with a lower limit of 0.1 micron, 0.5 micron, 1 micron, 2 microns, 5 microns and 20 microns, and an upper limit of 1000 microns, 500 microns, 200 microns, 100 microns, 75 microns, 50 microns, and 30 microns. In some embodiments, the microcapsules of this invention have a mean diameter in the range of 1 micron to 50 microns. In other embodiments, the microcapsules of this invention have a mean diameter in the range of 20 micron to 50 microns.

The microcapsules can be positively or negatively charged with a zeta potential in the range of −200 mV to +200 mV, e.g., at least 10 mV, 25 mV or greater, 40 mV or greater, 25 mV to 200 mV, and 40 mV to 100 mV, with a lower limit of −200 mV, −150 mV, −100 mV, −50 mV, −25 mV, −10 my, 0 mV, 10 mV, 2 mV 0, and 40 mV and an upper limit of 200 mV, 150 mV, 100 mV, 50 mV, 40 mV, 20 mV, 10 mV, and 0 mV. In some embodiments, the microcapsules each are positively charged. Not to be bound by theory, the positively charged microcapsules have a strong affinity to specific animate and inanimate surfaces (e.g., hair and fabric), and also are unexpectedly stable in certain consumer product bases such as hair conditioners, shampoos, shower gels, and fabric conditioners.

In some embodiments, the microcapsules of this invention are positively charged as indicated by a zeta potential of at least 10 mV, preferably at least 25 mV (e.g., 25 mV to 200 my), and more preferably at least 40 mV (e.g., 40 mV to 100 my). Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule. The zeta potential is an important indicator of the stability of the microcapsule in compositions or consumer products. Typically, a microcapsule having a zeta potential of 10 mV to 25 mV shows a moderate stability. Similarly, a microcapsule having a zeta potential of 25 mV to 40 mV shows a good stability and a microcapsule having a zeta potential of 40 mV to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin & Goetz, "Ultrasound for characterizing colloids" Elsevier, 2002.

The microcapsule of this invention has a fracture strength of 0.2 MPa to 80 MPa (e.g., 0.5 MPa to 60 MPa, 1 MPa to 50 MPa, and 5 MPa to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang, et al. (2001) *J. Microencapsulation* 18(5):593-602.

The microcapsule of this invention has a rupture force of less than 10 millinewtons ("mN") such as 0.05 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang, et al. (1999) *J. Microencapsulation* 16(1):117-124.

The combination of biopolymer and cross-linking agent (s), and amounts of the same, used in the preparation of the microcapsule shell can be selected to retain the at least one active material, e.g., in a consumer product base for an extended amount of time, and release the at least one active material under one or more specified triggering conditions.

The microcapsule composition of this invention can be a slurry or suspension, wherein the microcapsule is in a solvent (e.g., water) at a level 0.1% to 80% (preferably 1% to 65% and more preferably 5% to 45%) by weight of the microcapsule composition.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ instrument (Commercially available from ThermoScientific), using rotating disks at a shear rate of 21 $s^{-1}$ and a temperature of 25° C. In certain embodiments, the viscosity of a microcapsule composition of this invention is less than 3000 cP at a shear rate of 21 $s^{-1}$ and a temperature of 25° C.

Stability of a biodegradable core-shell microcapsule can be assessed using a number of different approaches including physical stability and/or storage stability. When assessing physical stability, an exemplary microcapsule composition may be dispersed in an aqueous phase and shown to be stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

When assessing storage stability, fragrance retention within the microcapsule may be measured directly after storage, at a desired temperature and time periods such as four weeks, six weeks, two months, three months or more in a consumer product base. The preferred manner is to measure total headspace of the consumer product at the specified time and to compare the results to the headspace of a control consumer product made to represent 0% retention via direct addition of the total amount of fragrance present. Alternatively, the consumer product may be performance tested after the storage period and the performance compared to the fresh product, either analytically or by sensory evaluation. This measurement often involves either measuring the fragrance headspace over a substrate used with the product, or odor evaluation of the same substrate. In certain embodiments, retention of the active material in the core of the instant microcapsules is assessed in a consumer product base, e.g., under storage conditions such as at a temperature in the range of 25° C. to 40° C., or more preferably in the range of 30° C. to 37° C., or most preferably 37° C., for an extended period of time of at least 2 weeks, 4 weeks, 6 weeks, 8 weeks, 16 weeks, or 32 weeks. In certain embodiments, the microcapsules of this invention retain at least 40%, 45%, 50%, 55%, 60%, 65%, 70%, 75%, 80%, 85%, 90%, 95%, or 99% of the active material when added to a consumer product base. In particular embodiments, the microcapsules of this invention, when added to a consumer product base, retain between 40% and 90% of the active material after being stored at 37° C. for at least 4 weeks, 8 weeks or 12 weeks. Alternatively stated, the microcapsules of this invention lose less than 50% of the active material due to leakage when added to a consumer product base and stored for 8 weeks at 37° C.

A “triggering condition,” as used herein, refers to an act or event that serves as a stimulus and initiates or precipitates a change in the microcapsule, such as a loss or altering of the microcapsule’s physical structure and/or a release of the active material in the core of the microcapsule. Such triggers include, e.g., subjecting the microcapsule to friction, swelling, a pH change, an enzyme, a change in temperature, a change in ionic strength, or a combination thereof. In some embodiments, the microcapsules release the active material in response to a dual release triggering mechanism, e.g., friction and a change in pH.

The cross-link density of the instant microcapsules can vary depending on the biopolymer and/or number and type of cross-linking agents used. Cross-link density can be defined in various ways. One way is as the number of chain segments (between cross-links) per unit volume, designated ν. Another way of expressing this is in terms of the average molecular weight between cross-links, designated as $M_c$. These two conventions can be related numerically, since the average segment weight (in grams) is $M_c/N$ (where N is the Avogadro number) and the average segment volume is therefore $M_c/N\rho$ (where ρ is the material density). Thus, the average number of chains per unit volume is given by, $$\nu = N\rho/M_c.$$

Hence cross-link density is inversely proportional to $M_c$. Increasing crosslink density increases material stiffness, and various expressions have been derived linking modulus to ν or $M_c$. The basis of any direct correlation relies on the cross-link providing the only restriction on segmental mobility (i.e., the hypothetical freely-jointed chain) and the closest approximation is for cross-linked materials in their rubbery state, especially when swollen. In this respect, cross-link density can be experimentally determined using a solvent swelling method. See, e.g., Zhang, et al. (1989) *Polymer* 30(11):2060-62.

The microcapsules of this invention are prepared using cross-linked biopolymers thereby providing a composition that is biodegradable. In particular, at least 30%, 40%, 50%, or 60% of the carbon present in the wall of the biodegradable microcapsules of this invention is derived from a natural source, in particular a plant source, rather than a petroleum-based source. Biodegradation can be assessed by a number of well-known tests.

G. Capsule Preparation

In general, the microcapsule compositions of this invention are prepared by emulsifying the at least one biopolymer with at least one active material, and cross-linking the at least one biopolymer with one or more cross-linking agents, thereby producing a biodegradable core-shell microcapsule. More specifically, an aqueous phase containing the biopolymer is mixed with an oil phase containing the active, the mixture is emulsified, one or more cross-linkers are added, and the resulting mixture is incubated under conditions sufficient to induce interfacial polymerization and cross-linking of the microcapsule wall material. To facilitate capsule formation, the emulsion can also include one or more dispersants and optionally a catalyst. The microcapsule wall is formed of a polymeric network containing the biopolymer. Not to be bonded by any theory, two or more biopolymers can be crosslinked or interweaved to form the polymeric network. Exemplary biodegradable core-shell microcapsule compositions are described herein as are their methods of production.

In some embodiments, a microcapsule composition of this invention is prepared by emulsifying at least one biopolymer, at least one active material, and a polyisocyanate cross-linker, adding a second cross-linking agent to said emulsion, and cross-linking and curing the microcapsule wall material. In certain embodiments, the second cross-linking agent is tannic acid. In other embodiments, a second cross-linking agent (e.g., a polyphenolic acid such as tannic acid) and third cross-linking agent (e.g., an aldehyde such as glutaraldehyde) are added to an emulsion including polyisocyanate as a first cross-linking agent.

In certain embodiments, one or more surfactants or dispersants are used in the method of this invention. In particular embodiments, a polystyrene sulfonate, CMC and/or modified starch is used as a dispersant.

The term "curing" as used in polymer chemistry and process engineering refers to a toughening or hardening process of a polymer by cross-linking of polymer chains, brought about by heat, chemical additives, or light radiation.

An illustrative method for preparing a biodegradable core-shell microcapsule including a gum as the biopolymer includes the steps of providing an aqueous phase containing a gum (e.g., a cationic guar gum) and an anionic emulsifier, providing an oil phase containing a polyisocyanate and an active material, emulsifying the aqueous phase into the oil phase form an oil-in-water emulsion, optionally adding a polyisocyanate or aldehyde, adjusting the pH to below 7 (e.g., 1-6), causing the formation of a microcapsule having a microcapsule core that contains the active material and a microcapsule wall that encapsulates the microcapsule core, and curing the microcapsule to obtain a gum microcapsule dispersed in the aqueous phase.

As another illustrative method, a biodegradable core-shell microcapsule is prepared, which includes a modified cellulose as the biopolymer. Such a microcapsule may be produced by the steps of providing an oil-in-water emulsion having a plurality of oil droplets dispersed in an aqueous phase, in which the oil-in-water emulsion contains a polyisocyanate, the oil phase contains an active material, and the aqueous phase contains a modified cellulose (e.g., HEC), obtaining a reaction mixture containing the oil-in-water emulsion, a multi-functional aldehyde (e.g., glutaraldehyde) and a polyphenol (e.g., tannic acid), providing a condition sufficient to induce interfacial polymerization in the reaction mixture to form a microcapsule having a microcapsule wall encapsulating a microcapsule core, and optionally, curing the microcapsule at a temperature of 15° C. to 135° C. for 5 minutes to 48 hours. In some embodiments, a catalyst (e.g., 1,4-diazabicyclo[2.2.2]octane is added to the reaction mixture to facilitate the polymerization. In according with this method, a polyurethane polymer that is the reaction product between HEC and polyisocyanate, in which the hydroxy group (—OH) on HEC reacts with the isocyanate group (—NCO) on the polyisocyanate to form the polyurethane bond. The polyphenol (e.g., tannic acid) also reacts with polyisocyanate to form a polyurethane polymer. Another example of the encapsulating polymer is an acetal or hemi-acetal product between HEC and the multi-functional aldehyde, in which the hydroxy group (—OH) on HEC reacts with the formyl group (—CHO) on the multi-functional aldehyde to form an acetal or hemi-acetal polymer. Polyphenol can also react with the multi-functional aldehyde to form an acetal or hemi-acetal polymer. It is preferred to have both the polyurethane polymer and the acetal/hemi-acetal polymer to form a microcapsule wall with sufficient stability, good degradability, and satisfactory fragrance release profile.

Oil-in-water emulsions can be prepared using conventional emulsion techniques by emulsifying an oil phase into an aqueous phase, e.g., in the presence of a capsule formation aid and mechanical shear. In one embodiment, the oil phase contains the active material (such as a fragrance), polyisocyanate and a core solvent (such as caprylic/capric triglyceride). In another embodiment, the aqueous phase contains water and a biopolymer (e.g., a polysaccharide, polypeptide or polyphenolic) with or without a surfactant. In a further embodiment, the oil phase contains the active material and a core solvent. In yet another embodiment, the aqueous phase contains water, polyisocyanate, and a capsule formation aid. In still another embodiment, the polyisocyanate is not added in either the oil or aqueous phase before emulsion and may optionally be added to a pre-formed oil-in-water emulsion.

In microcapsules including a polypeptide or combination of polypeptides, in particular a whey protein or plant storage protein, as the biopolymer, ideally the polypeptides are denatured prior to being cross-linked. Accordingly, a method for preparing a biodegradable core-shell microcapsule including a polypeptide as the biopolymer includes the steps of denaturing at least one whey protein or plant storage protein; emulsifying the at least one denatured whey protein or denatured plant storage protein with at least one active material; and cross-linking the at least one denatured whey protein or denatured plant storage protein with one or more cross-linking agents, thereby producing a biodegradable core-shell microcapsule.

Using a method of this invention, a relative high encapsulation efficiency is achieved. "Encapsulation efficiency" or "microencapsulation efficiency" or "MEE" represents the proportion of the active material core that is not available to an extracting solvent under specified test conditions. In accordance with the method of this invention, microencapsulation efficiencies in the range of 50% to 99.9% are attainable, or more preferably 60% to 99.7%. In particular, encapsulation efficiencies of at least 90%, 92%, 94%, 96%, 98%, or 99% are achieved.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is at least 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., excess cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also be dried, e.g., spray-dried, heat dried, and belt dried, to a solid form. In a spray drying process, a spray-dry carrier is added to a microcapsule composition to assist the removal of water from the slurry. See US 20120151790, US 20140377446, US 20150267964, US 20150284189, and US 20160097591.

According to one embodiment, the spray dry carriers can be selected from the group of carbohydrates such as chemically modified starches and/or hydrolyzed starches, gums such as gum Arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%, by weight of the microcapsule composition in slurry.

In certain embodiments, a microcapsule composition that is dried in the presence of a carrier, which further includes an unencapsulated or non-confined active material. Such compositions can be prepared by combining an aqueous carrier solution, in particular a starch solution; preparing an oil phase containing an active material (e.g., a flavor or fragrance); emulsifying the oil phase with the aqueous carrier solution to obtain an emulsion; mixing the emulsion with a biodegradable core-shell microcapsule composition; and spray drying the resulting mixture.

Optionally, a free flow agent (anticaking agent) may be included in the microcapsule composition. Free flow agents of particular use include silicas, which may be hydrophobic silicas (i.e., silanol surface treated with halogen silanes, alkoxysilanes, silazanes, and siloxanes sold under the trademarks SIPERNAT® D17, AEROSIL® R972 and R974 by Degussa) and/or hydrophilic silicas (i.e., silicas sold under the trademarks AEROSIL® 200, SIPERNAT® 22S, SIPERNAT® 50S, by Degussa, or SYLOID® 244 by Grace Davison). Free flow agents may be present from 0.01 to 10%, more preferable from 0.5 to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature for spray drying the microcapsule composition may be in the range of 150° C. to 240° C., preferably between 170° C. and 230° C., more preferably between 190° C. and 220° C.

Alternatively, granulates for use in a consumer product may be prepared in a mechanical granulator in the presence of a granulation auxiliary such as non-acid water-soluble organic crystalline solids. See WO 2005/097962.

The microcapsule of this invention can also be prepared by printing a microcapsule shell and a microcapsule core using a printing system such as a 3D printer. See WO 2016/172699 A1. The printing steps generally include depositing the active materials and the microcapsule shell material in a layer-by-layer fashion, preferably through separate printer heads. The microcapsule shell material can be polymers or oil-in-water emulsions as described above.

I. Consumer Products

The biodegradable core-shell microcapsule composition of this invention is well-suited for inclusion in any of a variety of consumer products where controlled release of active materials (e.g., fragrances or flavors) is desired. The microcapsule composition of this invention can be added to a consumer product base directly or be printed onto a product base or a movable product conveyor (e.g., a non-stick belt) for drying. See WO 2019/212896 A1. In a typical printing system, the microcapsule composition is printed onto a movable product conveyor that directly receives the printed microcapsule, which is then dried on the movable product conveyor to produce a dried product. Additional carriers and solvent can be added to the microcapsule composition before printing. In some embodiments, the viscosity of the microcapsule composition is adjusted to more than 500 cP or more than 1000 cP with a viscosity modifier. With reference to the print assembly, the print assembly can include a print head or array of nozzles and optionally be adapted to print the microcapsule in a dot pattern (e.g., arranged to facilitate drying, post-processing, and product quality). Optional features of the system include, a dehumidifier configured to supply desiccated air to the drying component; a supplemental energy source (e.g., a radiant heat source), for facilitating drying of the printed microcapsule; and/or a product discharge component for removing dried product from the movable product conveyor.

The biodegradable core-shell microcapsule composition can be added to the consumer product based at a level in the range of 0.001% to 50%, or more preferably 0.01% to 50% by weight of the consumer product base. Such consumer products can include, but are not limited to, a baby care product, a diaper rash cream or balm, a baby powder, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, or a wildlife scent.

Advantageously, the microcapsules of the invention do not tend to form visible aggregates (e.g., greater than 100 μm) and can readily be added to the base of a fabric softener, detergent, AP/deodorant, fine, personal care leave on, personal care rinse off, or home care product. Such consumer product bases can include surfactants, alkali materials, acidic materials, dyes, unencapsulated (neat) fragrances, and the like. As such, it is contemplated that certain biopolymer wall materials will be more compatible with certain consumer product bases.

As described herein, a spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g., shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

J. Consumer Product Base

As used herein, a "consumer product base" refers to a composition for use as a consumer product to fulfill specific actions, such as cleaning, softening, and caring or the like. Components of the consumer product base may include any suitable additive that produces an intended effect under intended use conditions of the consumer product. For example, consumer product base ingredients may be selected from the group of personal cleansing and/or conditioning agents such as hair care agents including shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof. Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of compounds may be useful for one or more of the agents listed above. For example, surfactants may be used for any number of the agents described above. Likewise, bleaching agents may be used for fabric care, hard surface cleaning, dishwashing and even teeth whitening. Therefore, one of ordinary skill in the art will appreciate that the agents will be selected based upon the desired intended use of the consumer product. For example, if a consumer product is for hair care and/or conditioning then one or more suitable surfactants, such as a lathering surfactant could be selected to provide the desired benefit to a consumer. Similarly, if a consumer product is for laundering clothes in a laundry operation, then one or more suitable surfactants and/or enzymes and/or builders and/or perfumes and/or suds suppressors and/or bleaching agents could be selected to provide the desired benefit to a consumer.

In one example, the agent is a non-perfume ingredient. In another example, the agent is a non-surfactant ingredient. In still another example, the agent is a non-ingestible ingredient, in other words an agent other than an ingestible ingredient.

In certain embodiments, the consumer product base includes one or more bleach activators, surfactants, builders, chelating agents, dye transfer inhibiting agents, dispersants, enzymes, and enzyme stabilizers, catalytic metal complexes, polymeric dispersing agents, deposition agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments, and combinations thereof. The precise nature of these ingredients, and levels of incorporation thereof, will depend on the physical form of the composition and the nature of the operation for which it is to be used. However, when one or more ingredients are present, such one or more ingredients may be present as detailed below.

Surfactants. Surfactants utilized may be of the anionic, nonionic, zwitterionic, ampholytic or cationic type or may comprise compatible mixtures of these types. Anionic and nonionic surfactants are typically employed if the product is a laundry detergent. In contrast, cationic surfactants are typically employed if the product is a fabric softener. In addition to the anionic surfactant, the product may further contain a nonionic surfactant. The product may contain up to from 0.01% to about 30%, alternatively from about 0.01% to about 20%, more alternatively from about 0.1% to about 10%, by weight of the product, of a nonionic surfactant. In some examples, the nonionic surfactant may include an ethoxylated nonionic surfactant. Suitable for use herein are the ethoxylated alcohols and ethoxylated alkyl phenols of the formula $R(OC_2H_4)_n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R^1(OC_2H_4)_nOH$, wherein $R^1$ is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The fabric and home care compositions may contain up to about 30%, alternatively from about 0.01% to about 20%, more alternatively from about 0.1% to about 20%, by weight of the product, of a cationic surfactant. Cationic surfactants include those which can deliver fabric care benefits, non-limiting examples which include: fatty amines; quaternary ammonium surfactants; and imidazoline quat materials.

Builders. The product may also contain from about 0.1% to 80% by weight of the product of a builder. Compositions in liquid form generally contain from about 1% to 10% by weight of the product of the builder component. Compositions in granular form generally contain from about 1% to 50% by weight of the product of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions composed of a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of $SiO_2$ to alkali metal oxide of from about 0.5 to about 4.0, or from about 1.0 to about 2.4. Also useful are aluminosilicates including zeolites.

Dispersants. The product may contain from about 0.1%, to about 10%, by weight of the product of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes. The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the product are from about 0.0001% to about 5% by weight of the product. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the products may be either or both enzyme-containing and enzyme-free.

Dye Transfer Inhibiting Agents. The product may also include from about 0.0001%, from about 0.01%, from about 0.05% by weight of the product to about 10%, about 2%, or even about 1% by weight of the product of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant. The product may contain less than about 5%, or from about 0.01% to about 3%, by weight of the product, of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners. The product may also include a brightener (also referred to as "optical brightener") and may include any compound that exhibits fluorescence, including compounds that absorb UV light and reemit as "blue" visible light. Non-limiting examples of useful brighteners include derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those sold under the trademark Tinopal-UNPA-GX® by Ciba Specialty Chemicals Corporation (High Point, NC).

Bleach System. Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer. The product may contain one or more stabilizers and thickeners. Any suitable level of stabilizer may be of use; exemplary levels include from about 0.01% to about 20%, from about 0.1% to about 10%, or from about 0.1% to about 3% by weight of the product. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g., xanthan gum), polyvinyl alcohol and derivatives thereof, cellulose and derivatives thereof including cellulose ethers and cellulose esters and tamarind gum (for example, including xyloglucan polymers), guar gum, locust bean gum (in some aspects comprising galactomannan polymers), and other industrial gums and polymers.

Deposition Aid. In some examples, the fabric and home care product may include from about 0.01% to about 10%, from about 0.05% to about 5%, or from about 0.15% to about 3%, by weight of the product, of a deposition aid. In some examples, the deposition aid may be a cationic or amphoteric polymer. In some examples, the cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

In some examples, the deposition aid may include a cationic acrylic based polymer. In a further aspect, the deposition aid may include a cationic polyacrylamide. In another aspect, the deposition aid may include a polymer composed of polyacrylamide and polymethacrylamidopropyl trimethylammonium cation. In another aspect, the deposition aid may be composed of poly(acrylamide-N-dimethyl aminoethyl acrylate) and its quaternized derivatives.

In some examples, the deposition aid may be selected from the group of cationic or amphoteric polysaccharides. In some examples, the deposition aid may be selected from the group of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In some examples, the MW of the cationic polymer may be from about 500 Daltons to about 37,500 Daltons.

Silicones. Suitable silicones include Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may include a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked. In some examples, the organosilicone may be a cyclic silicone. The cyclic silicone may be a cyclomethicone of the formula $[(CH_3)_2SiO]_n$ where n is an integer that may range from about 3 to about 7, or from about 5 to about 6.

In some examples, the organosilicone may include a functionalized siloxane polymer. Functionalized siloxane polymers may include one or more functional moieties selected from the group of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In some examples, the functionalized siloxane polymer may include a silicone polyether, also referred to as "dimethicone copolyol.".In general, silicone polyethers include a polydimethylsiloxane backbone with one or more polyoxyalkylene chains. The polyoxyalkylene moieties may be incorporated in the polymer as pendent chains or as terminal blocks. In some examples, the functionalized siloxane polymer may include an aminosilicone.

In some examples, the organosilicone may include amine ABn silicones and quat ABn silicones. Such organosilicones are generally produced by reacting a diamine with an epoxide.

Fabric Softening Actives. Non-limiting examples of fabric softening actives are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; dialkylenedimethylammonium salts such as dicanoladimethylammonium chloride, di(hard) tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N, N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above. It will be understood that combinations of softener actives disclosed above are suitable for use herein.

Fabric Hueing Agents. The product may further include a fabric hueing agent (sometimes referred to as shading, bluing or whitening agents). Typically, the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Color Index (CI) classifications of Acid, Direct, Basic, Reactive or hydrolyzed Reactive, Solvent or Disperse dyes for example that are classified as Blue, Violet, Red, Green or Black, and provide the desired shade either alone or in combination.

Suitable polymeric dyes include polymeric dyes selected from the group of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

Suitable dye clay conjugates include dye clay conjugates selected from the group comprising at least one cationic/basic dye and a smectite clay, and mixtures thereof.

The hueing agent may be incorporated into the product as part of a reaction mixture which is the result of the organic synthesis for a dye molecule, with optional purification step(s). Such reaction mixtures generally include the dye molecule itself and in addition may include un-reacted starting materials and/or by-products of the organic synthesis route.

Pigments. Suitable pigments include pigments selected from the group of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

Structurants. Useful structurant materials that may be added to adequately suspend a benefit agent or microcapsule include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, CA; Degussa AG or Dusseldorf, Germany; BASF AG of Ludwigshafen, Germany; Rhodia Corp. of Cranbury, NJ; Baker Hughes Corp. of Houston, TX; Hercules Corp. of Wilmington, DE; Agrium Inc. of Calgary, Alberta, Canada; ISP of NJ.

Anti-Agglomeration Agents. Useful anti-agglomeration agents include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Formaldehyde Scavenger. In some examples, the product may include a formaldehyde scavenger. Suitable formaldehyde scavengers include materials selected from the group of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly (vinyl alcohol)-co-poly(vinyl amine), poly(4-aminostyrene), poly(1-lysine), chitosan, hexane diol, ethylenediamine-N, N'-bisacetoacetamide, N-(2-ethylhexyl)acetoacetamide, 2-benzoylacetoacetamide, N-(3-phenylpropyl) acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, MO or PolySciences, Inc. of Warrington, PA.

In some examples, a formaldehyde scavenger may be combined with a microcapsule slurry, at a level, based on total slurry weight, of from about 2 wt. % to about 18 wt. %, from about 3.5 wt. % to about 14 wt. % or even from about 5 wt. % to about 13 wt. %.

In some examples, a formaldehyde scavenger may be combined with a product containing microcapsules, said scavengers being combined with said product at a level, based on total product weight, of from about 0.005% to about 0.8%, alternatively from about 0.03% to about 0.5%, alternatively from about 0.065% to about 0.25% of the product formulation.

In some examples, one or more of the aforementioned formaldehyde scavengers may be combined with a liquid fabric enhancing product containing a benefit agent containing a microcapsule composition at a level, based on total liquid fabric enhancing product weight, of from 0.005% to about 0.8%, alternatively from about 0.03% to about 0.4%, alternatively from about 0.06% to about 0.25% of the product formulation In some examples, such formaldehyde scavengers may be combined with a consumer product, for example, a liquid laundry detergent product containing microcapsules, said scavengers being selected from the group of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly (vinyl alcohol)-co-poly(vinyl amine), poly(4-aminostyrene), poly(l-lysine), chitosan, hexane diol, ethylenediamine-N,N'-bisacetoacetamide, N-(2-ethylhexyl) acetoacetamide, 2-benzoylacetoacetamide, N-(3-phenylpropyl) acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In some examples, such formaldehyde scavengers may be combined with a hair conditioning product containing microcapsules, at a level, based on total hair conditioning product weight, of from about 0.003 wt. % to about 0.30 wt. %, from about 0.03 wt. % to about 0.20 wt. % or even from about 0.06 wt. % to about 0.14 wt. %, said selection of scavengers being identical to the list of scavengers in the previous paragraph relating to a liquid laundry detergent product.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "include," "includes," and "including" are meant to be non-limiting.

The following non-limiting examples are provided to further illustrate the present invention.

Example 1: Consumer Products with Guar Gum Microcapsules

Guar Composition 1. An aqueous solution was prepared that contained 0.5% sodium polystyrene sulfonate (sold under the trademark FLEXAN® II by AkzoNobel Surface Chemistry, Bridgewater, NJ), 1% octenyl succinic anhydride (OSA)-modified starch (sold under the trademark PURITY GUM Ultra by Ingredion, Bridgewater, NJ), and 3% cationic guar (commercially available as Aquacat™ CG518 from Ashland, Covington, KY) in water. An oil solution was prepared that contained 1% of a trimethylolpropane adduct of xylylenediisocyanate (sold under the trademark TAKENATE® D110N by Mitsui Chemical, Japan), 32% of a model fragrance (IFF, Union Beach, New Jersey) and 8% caprylic/capric triglyceride (sold under the trademark NEOBEE® by Stepan Company, Northfield, IL). The two solutions were mixed and homogenized at 7400 rpm for 3 minutes. Subsequently, 0.67% of glutaraldehyde (Sigma Aldrich, St. Louis, MO) was added, followed by the addition of 0.66% diluted sulfuric acid to adjust the pH of the mixture to 2. The resultant mixture was cured at 55° C. for 2 hours and then at 75° C. for additional 2 hours. Guar Composition 1 thus prepared contained 3% cationic guar gum, 1% polyisocyanate, and 0.67% of glutaraldehyde, each by weight of the composition.

Guar Composition 2. Guar Composition 2 was prepared following the procedure for Guar Composition 1 except that (i) a 0.5% cationic guar (sold under the trademark N-HANCE® C261N by Ashland) was used instead of 3% Aquacat™ CG518, (ii) 0.01%, instead of 0.66%, sulfuric acid was added, and (iii) the microcapsule was cured at 55° C. for 4 hours. Guar Composition 2 thus prepared contained 0.5% cationic guar gum, 1% polyisocyanate, and 0.67% of glutaraldehyde, each by weight of the composition.

Guar Composition 3-7. Guar Compositions 3-7 were prepared following the procedure as described for Guar Composition 1 varying the amounts of polyisocyanate, glutaraldehyde, and tannic acid or varying the pH. See Table 3.

Guar Composition 8. Guar composition 8 was prepared following the same procedure as described for Guar Composition 2 except that an underivatized guar (commercially available as Guar Gum TICOLV™ from TIC Gums Inc., White March, MD) was added instead of cationic guar.

Guar Composition 9. Guar Composition 9 was prepared following the same procedure as described for Guar Composition 2 except that a non-ionic guar (sold under the trademark JAGUAR® HP-8 COS from Solvay, Cranbury, NJ) was added instead of cationic guar.

Guar Composition 10. Guar Composition 10 was prepared following the same procedure as described for Guar Composition 2 except that a underivatized guar gum (commercially available as HV-101 from AEP Colloids, Hadley, NY) was added instead of cationic guar.

Guar Composition 11. Guar Composition 11 was prepared following the same procedure as described for Guar Composition 3 except that (i) a sodium salt of naphthalene sulfonate condensate (sold under the trademark MORWET (D-425 by AkzoNobel) was used instead of FLEXAN II® and (ii) 3% Aquacat™ CG518 was added after the homogenization process instead of in the aqueous solution prior to emulsification.

Guar Composition 12. Guar Composition 12 was prepared following the same procedure as described for Guar Composition 2 except that glutaraldehyde was not added to the reaction mixture.

Sensory Performance Evaluations. The microcapsules prepared above were used in a fabric conditioner application and evaluated for their fragrance intensity in a labeled magnitude scale (LMS) of 0 to 30, in which a score of 1 indicates a weak smell, a score of 5 indicates an intermediate smell and a score of 15 indicates a strong smell. Each microcapsule composition was incorporated into an unfragranced model fabric conditioner base at 0.6% neat oil equivalence. More specifically, the fabric conditioner samples (35 grams per sample) each were separately introduced into a Miele Professional PW6055 Plus front loader washing machine during the rinse cycle thereof to condition 3 hand towels. After rinsing, the damp towels were evaluated blind by a panel of 3 people for intensity. A set 3 towels from a second wash, using the same wash conditions immediately above, were lined dried for 24 hours. The 3 dry towels each were stored in a polyethylene bag and evaluated by a panel of 3 people. Scores were recorded before and after each of the towels were rubbed by hand. Each rubbing test employed 5 time intervals, 2 seconds per time interval for a total rubbing time of 10 seconds.

Encapsulation Efficiency. Encapsulation efficiency (EE) was calculated as: EE=[1−(Free oil/Total Oil)]×100%. The free oil and total oil analysis were performed following the methods described on page 21 of WO 2017/161364.

Post-RUb Headspace Analysis. Headspace analysis of the microcapsules prepared above was also conducted using a TENAX® tube, in which the fragrance intensities were measured in ppb. The washed and dried towel was put in a plastic bag, sealed and rubbed. The headspace was collected through a nozzle.

Effect of Cross-Linkers on Fragrance Encapsulation and Performance. A batch of fabric conditioners were prepared using Guar Composition 2 (including isocyanate and glutaraldehyde as cross-linkers) and Guar Composition 12 (including only isocyanate as cross-linker). The fabric conditioners were then evaluated for their EE and fragrance intensity post-rub after washing and drying towels using the conditioners. The results are shown in Table 1.

TABLE 1

| | Guar Composition 2 | Guar Composition 12 |
|---|---|---|
| Polyisocyanate | 1% | 1% |
| Glutaraldehyde | 0.67% | 0% |
| Post-Rub Intensity | 6.2 | 0.7 |
| EE | 99.4% | 91.5% |

This analysis indicated that the combination of combination of cross-linking agents, in this case polyisocyanate and glutaraldehyde, had a significant impact on fragrance encapsulation and post-rub intensity.

Effect of Guar Gum Content on Fragrance Encapsulation and Performance. A batch of fabric conditioners was prepared that included either free fragrance oil (i.e., without encapsulation) or Gaur Composition 1 or Gaur Composition 2, which respectively included 3% and 0.5% cationic guar gum. The three fabric conditioners were evaluated right after washing and drying (T=0) and also after being stored for 4 weeks post-washing and -drying (T=4 weeks). The results of this analysis are presented in Table 2.

TABLE 2

| | Post-Rub Intensity | | |
|---|---|---|---|
| Sample | T = 0 | T = 4 weeks | EE |
| Gaur Composition 1 | 11.2 | 9.3 | 99.7% |
| Gaur Composition 2 | 10.9 | 7.9 | 99.4% |
| Free Fragrance Oil | 4.5 | 5.5 | — |

This analysis demonstrated that the inclusion of 3% guar gum improved the performance of the microcapsules.

Effect of Modifying Cross-Linkers and pH on Fragrance Encapsulation and Performance. A batch of fabric conditioners was prepared that included either free fragrance oil (i.e., without encapsulation) or Gaur Compositions 1 or 3-11. The fabric conditioners were evaluated for post-rub headspace and encapsulation efficiency. The results of this analysis are presented in Table 3.

TABLE 3

| | Amount of Cross-Linker | | | | Post-Rub | |
|---|---|---|---|---|---|---|
| Guar Composition | Isocyanate | Glutar-aldehyde | Tannic Acid | pH | Headspace (ppb) | EE |
| 1 | 1% | 0.67% | 0% | 2 | 2371.3 | 99.7% |
| 3 | 1% | 0.67% | 0% | 6 | 2260.7 | 99.7% |
| 4 | 0.8% | 0.67% | 0% | 2 | 1315.3 | 99.7% |
| 5 | 0.6% | 0.67% | 0% | 2 | 1046.3 | 99.4% |
| 6 | 1% | 0.67% | 2.5% | 2 | 2301.7 | 99.7% |
| 7 | 1% | 0% | 2.5% | 2 | 1874.3 | 99.7% |
| 8 | 1% | 0.67% | 0% | 2 | 1195.7 | 99.4% |
| 8 | 1% | 0.67% | 0% | 2 | 1509.7 | 99.7% |
| 10 | 1% | 0.67% | 0% | 2 | 1463 | 97.5% |
| 11 | 1% | 0.67% | 0% | 2 | 288.7 | 99.3% |
| Free Fragrance | — | — | — | — | 43.3 | — |

Reaction Confirmation. To confirm the reaction between a guar and glutaraldehyde, a mixture was prepared by adding 10 parts of a 1-10% guar aqueous solution and 1 part of a 50% glutaraldehyde aqueous solution, followed by adjusting the pH of the mixture to pH 2 with a concentrated sulfuric acid aqueous solution. The mixture was cured at 55° C. for 16 hours.

The above mixture turned into a transparent to semi-transparent solid gel. The gel was analyzed with nuclear magnetic resonance spectroscopy (NMR). The formation of acetal and hemi-acetal linkages was confirmed by NMR. Not to be bound by theory, it is believed that the hydroxyl groups (—OH) in the guar react with the formyl groups (—CHO) in the glutaraldehyde under the acidic condition (e.g., pH 1 to 6). This crosslinking reaction contributes to the formation of the shell of the microcapsule.

In addition, when isocyanate or tannic acid was combined with glutaraldehyde, additional cross-links were created as confirmed by X-ray Photoelectron Spectroscopy (XPS) and solid-state NMR. Indeed, this analysis confirmed the formation of polyurethane, polyimine, acetal, and hemiacetal cross-linkages in the microcapsule wall. These additional cross-linking reactions further reinforced the microcapsule wall and improved the encapsulation efficiency.

Effect of Modifying Guar Gum Content and Cross-Linker/Cross-Linker Content on Fragrance Encapsulation and Performance. Capsules composed of different components were prepared and sensory evaluations were conducted. In particular, guar capsules composed of different types and amounts of guar were prepared and compared (Tables 4 and 5). In addition, different amounts of glutaraldehyde (Table 6), tannic acid (Table 7) and isocyanate (Table 8) were evaluated. Further, process parameters such as pH (Table 9), addition of guar and cross-linker after emulsification (Tables 4 and 5, comparatives 10C and 11C) and cure temperature (Table 10) were evaluated.

Test Capsules 1-24 and Comparatives 4C-9C were prepared as follows. Changes in concentrations or process are indicated in the table. An aqueous solution was prepared that contained 0.5% sodium polystyrene sulfonate (commercially available under the tradename of FLEXAN® II from AkzoNobel Surface Chemistry, Bridgewater, NJ), 1% octenyl succinic anhydride (OSA)-modified starch (commercially available under the tradename of PURITY GUMS Ultra from Ingredion, Bridgewater, NJ), and guar in water. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% of a core solvent sold under the trademark NEOBEE® oil (a caprylic/capric triglyceride; Stepan Company, Northfield, IL). The two solutions were mixed and homogenized at 7400 rpm for 3 minutes. Subsequently, glutaraldehyde (Sigma Aldrich, St. Louis, MO) and/or tannic acid (commercially available under the tradename of TANAL® 2 from Ajinomoto, Itasca, IL) was added, followed by the addition of 0.66% diluted sulfuric acid to adjust the pH of the mixture. The resultant mixture was cured at 55° C. for 2 hours and then at 75° C. for an additional 2 hours.

Example 25 was prepared by combining 0.5% sodium polystyrene sulfonate (commercially available under the tradename of FLEXAN® II from AkzoNobel Surface Chemistry, Bridgewater, NJ), 1% octenyl succinic anhydride (OSA)-modified starch (commercially available under the tradename of PURITY GUM® Ultra from Ingredion, Bridgewater, NJ) and guar in water. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (sold under the trademark NEOBEE® oil by Stepan Company, Northfield, IL). The two solutions were mixed and homogenized at 7400 rpm for 3 minutes. Subsequently, glutaraldehyde (Sigma Aldrich, St. Louis, MO) and/or tannic acid (commercially available under the tradename of TANAL® 2 from Ajinomoto, Itasca, IL) were added, followed by the addition of 0.66% diluted sulfuric acid to adjust the pH of the mixture. The resultant mixture was cured at 55° C. for 2 hours.

Comparative 1C was prepared by combining 0.5% sodium polystyrene sulfonate (commercially available under the tradename MORWET® D-425 from AkzoNobel Surface Chemistry, Bridgewater, NJ), 1% polyvinylpyrrolidone (commercially available under the tradename of LUVIKSOL® K90 from BASF, Florham Park, NJ), and guar in water. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% of caprylic/capric triglyceride (sold under the tradename NEOBEE® oil; Stepan Company, Northfield, IL). The two solutions were mixed and homogenized at 7400 rpm for 3 minutes. Then glutaraldehyde (Sigma Aldrich, St. Louis, MO) was added, followed by the addition of 0.66% diluted sulfuric acid to adjust the pH of the mixture. The resultant mixture was cured at 55° C. for 2 hours and then at 75° C. for an additional 2 hours.

Comparatives 2C and 3C were prepared by combining 0.5% sodium polystyrere sulfonate (commercially available under the tradename of FLEXAN® II from AkzoNobel Surface Chemistry, Bridgewater, NJ), 1% octenyl succinic anhydride (OSA)-modified starch (commercially available under the tradename of PURITY GUMS Ultra from Ingredion, Bridgewater, NJ) in water. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (sold under the tradename NEOBEE® oil; Stepan Company, Northfield, IL). Then glutaraldehyde (Sigma Aldrich, St. Louis, MO) and tannic acid (commercially available under the tradename of TANAL® 2 from Ajinomoto, Itasca, IL) were added, followed by the addition of 0.66% diluted sulfuric acid to adjust the pH of the mixture. The resultant mixture was cured at 55° C. for 2 hours.

Comparatives 10C and 11C were prepared according to the following procedure. An aqueous solution was prepared that contained 0.5% sodium polystyrene sulfonate (commercially available under the tradename MORWET® D-425 from AkzoNobel Surface Chemistry, Bridgewater, NJ), 1% polyvinylpyrrolidone (commercially available under the tradename of LUVIKSOL® K90 from BASF, Florham Park, NJ, and guar in water. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (sold under the tradename NEOBEE® oil; Stepan Company, Northfield, IL). The two solutions were mixed and homogenized at 7400 rpm for 3 minutes. Subsequently, a cationic guar solution was added. Then glutaraldehyde (Sigma Aldrich, St. Louis, MO) was added, followed by the addition of 0.66% diluted sulfuric acid to adjust the pH of the mixture. The resultant mixture was cured at 55° C. for 2 hours and then at 75° C. for an additional 2 hours.

The exemplary fragrance capsules were added to a fabric conditioner at 0.6% NOE and evaluated for post-rub headspace (Tables 4 and 6-10) or post-rub sensory performance (Table 5). For post-rub headspace, towels were washed with fabric conditioner, dried and headspace in ppb was determined post-rub. For post-rub sensory performance, dried towels were evaluated based on 0-10 intensity after fabric conditioner wash.

TABLE 4

| Ex. | Guar | % Isocyanate | Primary X-Linker | % Free Oil | Post-Rub |
|---|---|---|---|---|---|
| 1C | None | 1.0 | 0.7% GlutAld | 1.2 | 114 |
| 2C | None | 1.0 | 0.7% GlutAld & 2.5% TA | <0.1 | 292 |
| 3C | None | 1.0 | 0.3% GlutAld & 2.5% TA | <0.1 | 443 |
| 10C | 4.0% Cationic Guar[1] | 1.0 | 0.1% GlutAld | 0.2 | 288 |
| 13 | 0.5% Non-Ionic Guar[2] | 1.0 | 0.7% GlutAld | 0.2 | 1463 |
| 14 | 0.5% Food Guar[3] | 1.0 | 0.7% GlutAld | 0.1 | 1196 |
| 15 | 0.5% Food Guar[4] | 1.0 | 0.7% GlutAld | 1.2 | 1510 |

GlutAld, glutaraldehyde; TA, tannic acid.
Guar used was sold under the tradenames
[1]Aquacat ™ (Ashland),
[2]JAGUAR ® HP (Solvay),
[3]HV-101 (AEP Colloids),
[4]TICOLV (Tic Gum).

TABLE 5

| Ex. | Guar | % Isocyanate | Primary X-Linker | % Free Oil | Post-Rub |
|---|---|---|---|---|---|
| 1 | 3% Cationic Guar[1] | 1.0 | 0.7% GlutAld & 1.0% TA | <0.1 | 5.3 |
| 2 | 3% Cationic Guar[1] | 1.0 | 0.7% GlutAld & 2.5% TA | <0.1 | 6.1 |
| 3 | 3% Cationic Guar[1] | 1.0 | 0.7% GlutAld | 0.1 | 4.8 |
| 4 | 1% Cationic Guar[1] | 1.0 | 0.7% GlutAld | <0.1 | 3.4 |
| 5 | 3% Cationic Guar[2] | 1.0 | 0.7% GlutAld | 0.2 | 5.6 |
| 6 | 0.5% Cationic Guar[2] | 1.0 | 0.7% GlutAld | 0.2 | 6.2 |
| 7 | 0.5% Cationic Guar[3] | 1.0 | 0.7% GlutAld | 0.4 | 3.1 |
| 8 | 0.5% Cationic Guar[4] | 1.0 | 0.7% GlutAld | 0.4 | 3.2 |
| 9 | 2.0% Cationic Guar[2] | 1.0 | 1.0% TA | <0.1 | 5.2 |
| 10 | 1.0% Cationic Guar[2] | 1.0 | 1.0% TA | <0.1 | 3.7 |
| 11 | 0.5% Cationic Guar[5] | 1.0 | 1.0% TA | 0.1 | 2.0 |
| 12 | 2.0% Cationic Guar[6] | 1.0 | 1.0% TA | <0.1 | 3.0 |

TABLE 5-continued

| Ex. | Guar | % Isocyanate | Primary X-Linker | % Free Oil | Post-Rub |
|---|---|---|---|---|---|
| 4C | 4% Cationic Guar[1] | 0.0 | 0.7% GlutAld | 9.6 | 2.0 |
| 5C | 2% Cationic Guar[1] | 0.0 | 0.7% GlutAld | 9.2 | 2.2 |
| 6C | 0.5% Cationic Guar[1] | 0.0 | 0.7% GlutAld | 13.3 | 1.8 |
| 7C | 0.5% Cationic Guar[2] | 1.0 | 0.0 | 1.7 | 0.7 |
| 11C | 5% Cationic Guar[2] | 1.0 | 0.7% GlutAld | 14.9 | 0.8 |

GlutAld glutaraldehyde; TA, tannic acid.
Guar used was sold under the tradenames
[1]Aquacat™ (Ashland),
[2]N-HANCE ® (Ashland),
[3]JAGUAR ® C14S (Solvay),
[4]DEHYQUART ® (BASF),
[5]JAGUAR ® C-14-S (Ashland),
[6]GUARSAFE ® JK-141 (Jingkun).

To further evaluated the cross-linkers, different amounts of glutaraldehyde (Table 6), tannic acid (Table 7) and isocyanate (Table 8) were evaluated.

TABLE 6

| Ex. | Guar | % Isocyanate | Primary X-Linker | % Free Oil | Post-Rub |
|---|---|---|---|---|---|
| 3 | 3% Cationic Guar[1] | 1.0 | 0.7% GlutAld | 0.1 | 1812 |
| 16 | 3% Cationic Guar[1] | 1.0 | 0.3% GlutAld | 0.1 | 1307 |
| 17 | 3% Cationic Guar[1] | 1.0 | 0.1% GlutAld | 0.2 | 686 |

GlutAld, glutaraldehyde.
[1]Guar used was sold under the tradename Aquacat™ (Ashland).

TABLE 7

| Ex. | Guar | % Isocyanate | Primary X-Linker | % Free Oil | Post-Rub |
|---|---|---|---|---|---|
| 18 | 1% Cationic Guar[1] | 1.0 | 1.0% TA | <0.1 | 2031 |
| 19 | 1% Cationic Guar[1] | 1.0 | 1.8% TA | <0.1 | 2016 |

TA, tannic acid.
[1]Guar used was sold under the tradename N-HANCE ® (Ashland).

TABLE 8

| Ex. | Guar | % Isocyanate | Primary X-Linker | % Free Oil | Post -Rub |
|---|---|---|---|---|---|
| 3 | 3% Cationic Guar[1] | 1.0 | 0.7% GlutAld | <0.1 | 2046 |
| 20 | 3% Cationic Guar[1] | 0.8 | 0.7% GlutAld | 0.1 | 1315 |
| 21 | 3% Cationic Guar[1] | 0.6 | 0.7% GlutAld | 0.2 | 1046 |
| 17 | 3% Cationic Guar[1] | 1.0 | 0.1% GlutAld | <0.1 | 1737 |
| 80 | 3% Cationic Guar[1] | 0.8 | 0.1% GlutAld | 0.4 | 48 |
| 90 | 3% Cationic Guar[1] | 0.6 | 0.1% GlutAld | 1.0 | 41 |

GlutAld, glutaraldehyde.
[1]Guar used was sold under the tradename AquacatTM (Ashland).

Further, process parameters including pH (Table 9) and cure temperature (Table 10) were evaluated.

TABLE 9

| Ex. | Guar | pH | % Isocyanate | Primary X-Linker | % Free Oil | Post-Rub |
|---|---|---|---|---|---|---|
| 3 | 3% Guar[1] | 3 | 1.0 | 0.7% GlutAld | <0.1 | 2210 |
| 22 | 3% Guar[1] | 7 | 1.0 | 0.7% GlutAld | <0.1 | 2251 |
| 10C | 3% Guar[1] | 9 | 1.0 | 0.7% GlutAld | <0.1 | 140 |

TABLE 9-continued

| Ex. | Guar | pH | % Isocyanate | Primary X-Linker | % Free Oil | Post-Rub |
|---|---|---|---|---|---|---|
| 3 | 3% Guar[1] | 3 | 1.0 | 0.7% GlutAld & 2.5% TA | <0.1 | 1777 |
| 23 | 3% Guar[1] | 7 | 1.0 | 0.7% GlutAld & 2.5% TA | 0.1 | 2081 |

GlutAld, glutaraldehyde; TA, tannic acid.
[1]Guar used was sold under the tradename Aquacat ™ (Ashland).

TABLE 10

| Ex. | Guar | Temperature (hours) | % Isocyanate | Primary X-Linker | % Free Oil | Post-Rub |
|---|---|---|---|---|---|---|
| 25 | 3% Guar[1] | 55° C. (2 hours) | 1.0 | 0.7% GlutAld | <0.1 | 2371 |
| 3 | 3% Guar[1] | 55° C. (2 hrs) + 75° C. (2 hrs) | 1.0 | 0.7% GlutAld | <0.1 | 2046 |

GlutAld, glutaraldehyde.
[1]Guar used was sold under the tradename Aquacat ™ (Ashland).

Selected guar capsule compositions were subsequently evaluated for performance in hair conditioner and shampoo applications. The generic hair conditioner base was composed of 4% fatty alcohol, 0.7% Behentrimonium Chloride, 1.0% TAS, 2.5% silicone and 0.5% preservative. The guar capsules were added to the hair conditioner base at a fragrance equivalence of 0.25% in the final product. Performance was evaluated at the post-brush stage, wherein hair swatches were conditioned with the hair conditioner, washed, dried, brushed and rated for fragrance intensity on a scale of 0-10 (Ex. 3 and 10) or via headspace determinations (Ex. 13-15) (Table 11).

TABLE 11

| Ex. | Guar | % Isocyanate | Primary X-Linker | % Free Oil | Post-Rub |
|---|---|---|---|---|---|
| 3 | 3% Cationic Guar[1] | 1.0 | 0.7% GlutAld | <0.1 | 4.8 |
| 10 | 1% Cationic Guar[2] | 1.0 | 1.0% TA | 0.1 | 3.7 |
| 13 | 0.5% Non-Ionic Guar[3] | 1.0 | 0.7% GlutAld | 0.2 | 1463 |
| 14 | 0.5% Food Guar[4] | 1.0 | 0.7% GlutAld | <0.1 | 1196 |
| 15 | 0.5% Food Guar[5] | 1.0 | 0.7% GlutAld | 0.4 | 1510 |

GlutAld, glutaraldehyde; TA, tannic acid.

Guar used was sold under the tradename [1]Aquacat™ (Ashland), [2]N-HANCE® (Ashland), [3]JAGUAR® HP (Solvay), [4]HV-101 (AEP Colloids), [5]TICOLV (Tic Gum).

The generic hair shampoo base was composed of 12% SLES, 1.6% CAPB, 0.2% Guar, 2-3% silicone and 0.5% preservative. The guar capsules, along with 0.25% of a deposition aid polymer, were added to the hair shampoo base at a fragrance equivalence of 0.25% in the final product. Performance was evaluated at the post-brush stage, wherein hair swatches were washed with the shampoo, dried, brushed and rated for fragrance intensity on a scale of 0-10 (Table 12).

TABLE 12

| Ex. | Guar | % Isocyanate | Primary X-Linker | % Free Oil | Post-Rub |
|---|---|---|---|---|---|
| 3 | 3% Cationic Guar[1] | 1.0 | 0.7% GlutAld | <0.1 | 5.8 |
| 10 | 1% Cationic Guar[2] | 1.0 | 1.0% TA | <0.1 | 7.3 |

TABLE 12-continued

| Ex. | Guar | % Isocyanate | Primary X-Linker | % Free Oil | Post-Rub |
|---|---|---|---|---|---|
| 13 | 0.50 Non-Ionic Guar[3] | 1.0 | 0.7% GlutAld | 0.2 | 5 |
| 14 | 0.5% Food Guar[4] | 1.0 | 0.7% GlutAld | 0.1 | 2 |
| 15 | 0.5% Food Guar[5] | 1.0 | 0.7% GlutAld | 1.2 | 2.5 |

GlutAld, glutaraldehyde; TA, tannic acid.
Guar used was sold under the tradename
[1]Aquacat™ (Ashland),
[2]N-HANCE ® (Ashland),
[3]JAGUAR ® HP (Solvay),
[4]HV-101 (AEP Colloids),
[5]TICOLV (Tic Gum).

In light of the data presented herein, a guar capsule of use in the invention is composed of gaur with a combination of isocyanate, tannic acid and/or glutaraldehyde as cross-linking agents. Such capsules are of particular use in the delivery of fragrances in a hair care product.

Example 2: Fabric Conditioner with Hydroxyethylcellulose Microcapsules

HEC Composition 1. HEC Composition 1 was prepared by mixing 20 grams (g) of a model fragrance and 2 g of caprylic/capric triglyceride (a core solvent sold under the trademark NEOBEE® oil M-5, Stepan, Chicago, IL) to prepare an oil phase. In a separate beaker, an aqueous solution was obtained by mixing an aqueous solution (60 g) containing 10% HEC (commercially available as Natrosol™ 250LR, Ashland Specialty Ingredients, Wilmington, DE), an aqueous solution (5 g) of a 10% sodium salt of polystyrene sulfonate (a capsule formation aid, sold under the trademark FLEXAN® II, AkzoNobel Surface Chemistry, Ossining, NY), an aqueous solution (10 g) of 1% carboxymethyl cellulose (a capsule formation aid, sold under the trademark WALOCEL® CRT50000, Dow Chemical Company, Midland, MI), an aqueous solution (0.2 g) of 20% DABCO crystalline (a catalyst, 1,4-Diazabicyclo[2.2.2]octane, Evonik, Essen, Germany), and a water dispersible aliphatic polyisocyanate (1 g) (a polyisocyanate based on hexamethylene diisocyanate (HDI) sold under the trademark BAYHYDUR® 305, Covestro, Leverkusen, Germany). The oil phase was then emulsified into the aqueous phase to form an oil-in-water emulsion under shearing (ULTRA TURRAX™, T25 Basic, IKA WERKE) at 9500 rpm for two minutes.

After the oil-in-water emulsion was stirred at 25° C. for 0.5 hour, 2 g of 25% aqueous glutaraldehyde solution (Sigma-Aldrich, St. Louis, MO) and 30 g of 10% tannic acid aqueous solution (Sigma-Aldrich, St. Louis, MO) were added under constant mixing. After the temperature was raised to 55° C., the resultant capsule slurry was stirred for one hour, and then two hours at 75° C. The encapsulation efficiency was 99.9%.

HEC Composition 2. HEC Composition 2 was prepared following the procedure described for HEC Composition 1 except that a different water dispersible aliphatic polyisocyanate (sold under the trademark DESMODUR® N100A, Covestro, Leverkusen, Germany) was added in the oil phase instead of BAYHYDUR® 305 in the aqueous phase. The encapsulation efficiency was 99.9%.

HEC Composition 3. HEC Composition 3 was prepared following the procedure described for HEC Composition 2 except that trimethylol propane-adduct of xylylene diisocyanate (sold under the trademark TAKENATE® D100EA;

Mitsui Chemicals Inc., Japan) was used instead of DESMODUR® N100A. The encapsulation efficiency was 99.9%.

HEC Composition 4. HEC Composition 4 was prepared following the procedure described for HEC Composition 1 except that the aqueous phase contained a 10% HEC aqueous solution (45 g) and a 10% hydroxypropyl cellulose aqueous solution (15 g) (Dow Chemical Company, Midland, MI), instead of a HEC solution only. The encapsulation efficiency was 99.9%.

HEC Composition 5. HEC Composition 5 was prepared by mixing 20 grams (g) of a model fragrance and 2 g of caprylic/capric triglyceride (sold under the trademark NEOBEE® oil M-5, Stepan, Chicago, IL) to produce an oil phase. In a separate beaker, an aqueous solution was obtained by mixing an aqueous solution (60 g) containing 10% HEC (Natrosol™ 250 LR, Ashland Specialty Ingredients, Wilmington, DE), an aqueous solution (5 g) of 10% a sodium salt of polystyrene sulfonate (sold under the trademark FLEXAN® II; AkzoNobel Surface Chemistry, Ossining, NY), an aqueous solution (10 g) of 1% carboxymethyl cellulose (sold under the trademark WALOCEL® CRT50000; Dow Chemical Company, Midland, MI), an aqueous solution (0.2 g) 20% DABCO crystalline (1,4-Diazabicyclo[2.2.2]octane, Evonik, Essen, Germany), and a water dispersible aliphatic polyisocyanate (1 g) (sold under the trademark BAYHYDUR® 305; Covestro, Leverkusen, Germany). The oil phase was then emulsified into the aqueous phase to form an oil-in-water emulsion under shearing at 9600 rpm for two minutes.

After the oil-in-water emulsion was stirred at 25° C. for 0.5 hour, 2 g of 25% aqueous glutaraldehyde solution (Sigma-Aldrich, St. Louis, MO) and 30 g of 10% tannic acid aqueous solution (Sigma-Aldrich, St. Louis, MO) were added under constant mixing. After the temperature was raised to 55° C., the resultant capsule slurry was stirred for one hour, and then two hours at 75° C. Subsequently, the pH was adjusted to 7.5 using 25% NaOH solution. A 20% lysine solution (7.5 g) (Sigma-Aldrich, St. Louis, MO) was added. The mixture was stirred for an additional two hours at 75° C. The encapsulation efficiency was 99.9%.

HEC Composition 6. HEC Composition 6 was prepared following the procedure described for HEC Composition 5 except that 0.67 g 30% branched polyethyleneimine (BASF, Ludwigshafen, Germany) was added instead of lysine.

HEC Composition 7. HEC Composition 7 was prepared following the procedure described for HEC Composition 5 except that 0.5 g 40% hexamethylenediamine (Invista, Wichita, KS) was added instead of adding lysine.

HEC Composition 8. HEC Composition 8 was prepared following the procedure described for HEC Composition 5 except that 10 g of a 2% pectin aqueous solution (CP Kelco, Atlanta, GA) was added instead of lysine.

HEC Composition 9. HEC Composition 9 was prepared by mixing 14.6 g of a model fragrance and 1.4 g of caprylic/capric triglyceride (sold under the trademark NEOBEE® oil M-5; Stepan, Chicago, IL) to produce an oil phase. In a separate beaker, an aqueous solution was obtained by mixing an aqueous solution (43.8 g) containing 10% HEC (Natrosol™ 250 LR; Ashland Specialty Ingredients, Wilmington, DE), an aqueous solution (3.6 g) of a 10% sodium salt of polystyrene sulfonate (sold under the trademark FLEXAN® II, AkzoNobel Surface Chemistry, Ossining, NY), an aqueous solution (7.3 g) of 1% carboxymethyl cellulose (sold under the trademark WALOCEL® CRT50000, Dow Chemical Company, Midland, MI), an aqueous solution (0.12 g) 20% DABCO crystalline (Evonik, Essen, Germany), and a water dispersible aliphatic polyisocyanate (0.58 g) (sold under the trademark BAYHYDUR® 305, Covestro, Leverkusen, Germany). The oil phase was then emulsified into the aqueous phase to form an oil-in-water emulsion under shearing at 9600 rpm for two minutes.

After the oil-in-water emulsion was stirred at 25° C. for 0.5 hour, 1.5 g of 25% aqueous glutaraldehyde solution (Sigma-Aldrich, St. Louis, MO) and 21.9 g of a 10% tannic acid aqueous solution (Sigma-Aldrich, St. Louis, MO) were added under constant mixing. After the temperature was raised to 55° C., the resultant capsule slurry was stirred for one hour, and then two hours at 75° C. Subsequently, the pH was adjusted to 7.0 using 25% NaOH solution. The mixture was stirred for two hours at 80° C. The encapsulation efficiency was 99.9%.

HEC Composition 10. HEC Composition 10 was prepared following the procedure described for HEC Composition 9 except that the water dispersible aliphatic polyisocyanate (0.58 g) was added after the emulsion formed, instead of in the aqueous phase before making the emulsion.

HEC Composition 11. HEC Composition 11 was prepared following the procedure described for HEC Composition 9 except that the mixture was stirred for two hours at 85° C. after the pH was adjust to 7.0, instead of two hours at 80° C.

HEC Composition 12. HEC Composition 12 was prepared following the procedure described for HEC Composition 9 except that the mixture was stirred for one hour at 90° C. after the pH was adjusted to 7.0, instead of two hours at 80° C.

HEC Composition 13. HEC Composition 13 was prepared following the procedure described for HEC Composition 1 except that after the oil-in-water emulsion was stirred at 25° C. for 0.5 hour, glutaraldehyde was added and the slurry was incubated at 25° C. for an addition 0.5 hour. Subsequently, tannic acid was added and the slurry was incubated at 25° C. for 1 hour followed by a 2-hour incubation at 80° C. The pH was then adjusted to 7.0 using 25% NaOH solution and the mixture was stirred for two hours at 80° C.

Comparative Composition. A comparative composition was prepared following the procedure described for HEC Composition 1 except that hydroxypropyl cellulose (HPC) was used instead of HEC.

Performance of HEC Compositions in EU Fabric Conditioner Base. To establish the microcapsule performance, HEC Compositions 1-12 were individually blended into a model fabric conditioner solution. The fragrance load was 0.6% neat oil equivalent (NOE). The perfumery benefit of the microcapsules was evaluated by conducting a laundry experiment using accepted experimental protocols using an European wash machine. Terry towels were used for the washing experiments and were washed with European fabric conditioners containing fragrance-loaded capsules before being evaluated by a panel of 12 judges. The fragrance intensity was evaluated after gentle tossing of the towels and rated from a scale ranging from 0 to 35. The pre-gentle tossing refers to the evaluations of the towels by panelists before the folding of the towels. The gentle tossing refers to the folding of the towels twice, followed by the evaluation of the towels by panelists. A numerical value of 4 would suggest the fabric only produced weak intensity while a value of 30 indicated the conditioner generated a very strong smell.

For HEC Composition 1, this analysis indicated that the towel had a pre-toss fragrance intensity of 6.8, a gentle-toss fragrance intensity of 9, and a post-rub intensity of 11.2. For HEC compositions 2-12, each showed unexpectedly high fragrance intensity.

In light of the data presented herein, an HEC capsule of use in the invention is composed of 0.5 to 10 wt. % HEC (preferably an HEC of S100K) with a combination of isocyanate (e.g., at a HEC:isocyanate ratio in the range of 11:1 to 3:1), tannic acid (e.g., 0.01 to 5 wt. %) and glutaraldehyde (e.g., 0 to 5 wt. %) as cross-linking agents. In alternative embodiments, an HEC capsule is composed of HEC with tannic acid and isocyanate as cross-linkers. Such capsules may optionally be used in combination with a deposition aid (e.g., chitosan) and are of particular use in the delivery of fragrances in fabric care products (e.g., conditioners, and liquid detergents), hair care products (e.g., conditioners and shampoos), antiperspirants, deodorants and fine fragrance products.

Example 3: Lignin Microcapsule Compositions

An aqueous solution was prepared that included 0.8% sodium polystyrene sulfonate (sold under the trademark FLEXAN® II by AkzoNobel Surface Chemistry, Bridgewater, NJ), 0.1% carboxymethyl cellulose, and 1.2% lignin in water. An oil solution was prepared that contained 0.75% water dispersible aliphatic polyisocyanate (sold under the trademark DESMODURM N100A, Covestro, Leverkusen, Germany), 22% of a model fragrance (IFF, Union Beach, NJ) and 0.4% caprylic/capric triglyceride (sold under the trademark NEOBEE® by Stepan Company, Northfield, IL). The two solutions were mixed under shearing at 9500 rpm. An aqueous solution of DABCO crystalline (Evonik, Essen, Germany) (0.03%) was added and the emulsion was incubated at 25° C. for one hour under constant mixing. Subsequently, 1.7% tannic acid (Sigma-Aldrich, St. Louis, MO) was added and the mixture was stirred for one hour at 25° C., and then two hours at 75° C. Lysine (0.6%) (Sigma-Aldrich, St. Louis, MO) was added and the mixture was stirred for an additional hour at 75° C.

Example 4: Pectin Microcapsule Compositions

An aqueous solution was prepared that included 0.3% sodium polystyrene sulfonate (sold under the trademark FLEXAN® II by AkzoNobel Surface Chemistry, Bridgewater, NJ), 0.1% carboxymethyl cellulose, and 0.8% pectin in water. An oil solution was prepared that contained 0.7% water dispersible aliphatic polyisocyanate (sold under the trademark DESMODUR® N100A, Covestro, Leverkusen, Germany), 22% of a model fragrance (IFF, Union Beach, NJ) and 0.4% caprylic/capric triglyceride (sold under the trademark NEOBEE® by Stepan Company, Northfield, IL). The two solutions were mixed under shearing at 9500 rpm to provide an emulsion with a ratio of polyisocyanate to pectin of about 1:1. An aqueous solution of DABCO crystalline (Evonik, Essen, Germany) (0.03%) was added and the emulsion was incubated at 25° C. for one hour under constant mixing. Subsequently, 1.6% tannic acid (Sigma-Aldrich, St. Louis, MO) was added and the mixture was stirred for one hour at 25° C., and then two hours at 85° C. Lysine (0.5%) (Sigma-Aldrich, St. Louis, MO) was added and the mixture was stirred for an additional hour at 85° C.

Stability. The resulting pectin microcapsule composition was modified by the addition of Xanthan gum (sold under the tradename PRE-HYDRATED® TICAXAN® Rapid-3 powder, TIC Gums; 0.15% or 0.3% w/w) and Aculyn™ 22 (an anionic hydrophobically modified alkali-soluble acrylic polymer, Dow Chemical; 1% w/w) as rheology modifiers/additives. Stability of the modified pectin microcapsule compositions was assessed after 4 weeks at room temperature (Table 13) or at 37° C. (Table 14) and after 8 weeks at room temperature (Table 15) or at 37° C. (Table 16).

TABLE 13

| Additive | MCS/Mode (μm) | | pH | Viscosity (cPs) | Separation (%) |
|---|---|---|---|---|---|
| Aculyn ™ 22 | 10.6 | 10.2 | 6.02 | 481.9 | 10.8 |
| 0.15% XG | 5.9 | 7.09 | 6.28 | 266.6 | 0 |
| 0.3% XG | 5.85 | 7.08 | 6.25 | 623.02 | 0 |
| None | 5.9 | 7.07 | 6.3 | 22.4 | 40.8 |

XG, Xanthan gum

TABLE 14

| Additive | MCS/Mode (μm) | | pH | Viscosity (cPs) | Separation (%) |
|---|---|---|---|---|---|
| Aculyn 22 | 19.2 | 10.7 | 5.91 | 1124.6 | 14.1 |
| 0.15% XG | 5.96 | 7.14 | 5.77 | 262.2 | 0 |
| 0.3% XG | 6.01 | 7.22 | 5.72 | 600.3 | 0 |
| None | 5.97 | 7.1 | 5.87 | 23.5 | 38.8 |

XG, Xanthan gum

TABLE 15

| Additive | MCS/Mode (μm) | | pH | Viscosity (cPs) | Separation (%) |
|---|---|---|---|---|---|
| 0.15% XG | 5.99 | 7.22 | 5.82 | 748.22 | 0 |
| 0.3% XG | 5.83 | 7.04 | 5.69 | 116.8 | 0 |
| None | 5.86 | 7 | 5.73 | 335.57 | 41 |

XG, Xanthan gum

TABLE 16

| Additive | MCS/Mode (μm) | | pH | Viscosity (cPs) | Separation (%) |
|---|---|---|---|---|---|
| 0.15% XG | 5.85 | 7.11 | 5.71 | 717.4 | 0 |
| 0.3% XG | 5.99 | 7.11 | 6.16 | 28.7 | 0 |
| None | 5.93 | 7.13 | 5.72 | 326.56 | 42.4 |

XG, Xanthan gum

Post addition of Xanthan gum and Aculyn™ 22 provided significantly reduced capsule separation over the 8-week evaluation at both room temperature and at 37° C. Notably, Xanthan gum was also evaluated at 0.08% and provided similar benefits.

Sensory Performance. To establish the microcapsule performance, samples were individually blended into a model rinse conditioner solution. The perfumery benefit of the microcapsules was evaluated by conducting a laundry experiment using accepted experimental protocols using an European wash machine. Terry towels were used for the washing experiments and were washed with rinse conditioner containing fragrance-loaded capsules and cabinet (line) dried before being evaluated by a panel of 12 judges after at 4 weeks at room temperature (Table 17) or at 37° C. (Table 18) and after 8 weeks at room temperature (Table 19) or at 37° C. (Table 20). The fragrance intensity was evaluated pre-rub, after gentle tossing (5×) and after vigorous rub touch points on a scale ranging from 0 to 35. A numerical value of 4 would suggest the fabric only produced weak intensity while a value of 30 indicated the conditioner generated a very strong smell.

TABLE 17

| Capsule | Additive | Pre-Rub | 5X Toss | Post-Rub |
|---|---|---|---|---|
| Pectin | None | 7.46 | 9.77 | 11.39 |
| Pectin | None | 7.85 | 11.43 | 13.57 |
| Pectin | Aculyn ™ 22 | 8.42 | 10.40 | 12.93 |
| Pectin | 0.15% XG | 7.57 | 10.08 | 12.94 |
| Pectin | 0.3% XG | 7.80 | 10.99 | 11.91 |

XG, Xanthan gum

TABLE 18

| Capsule | Additive | Pre-Rub | 5X Toss | Post-Rub |
|---|---|---|---|---|
| Pectin | None | 8.40 | 10.43 | 10.73 |
| Pectin | None | 7.35 | 7.86 | 11.43 |
| Pectin | Aculyn ™ 22 | 7.54 | 9.51 | 11.43 |
| Pectin | 0.15% XG | 7.31 | 7.58 | 10.40 |
| Pectin | 0.3% XG | 7.20 | 7.78 | 10.00 |

XG, Xanthan gum

TABLE 19

| Capsule | Additive | Pre-Rub | 5X Toss | Post-Rub |
|---|---|---|---|---|
| Pectin | None | 9.09 | 11.28 | 12.70 |
| Pectin | None | 8.32 | 9.38 | 13.26 |
| Pectin | Aculyn ™ 22 | 9.24 | 11.41 | 13.20 |
| Pectin | 0.15% XG | 8.25 | 10.66 | 13.21 |
| Pectin | 0.3% XG | 8.11 | 10.03 | 12.82 |

XG, Xanthan gum

TABLE 20

| Capsule | Additive | Pre-Rub | 5X Toss | Post-Rub |
|---|---|---|---|---|
| Pectin | None | 8.79 | 10.71 | 12.08 |
| Pectin | None | 7.19 | 8.47 | 12.36 |
| Pectin | Aculyn ™ 22 | 7.45 | 10.08 | 13.20 |
| Pectin | 0.15% XG | 6.52 | 8.40 | 13.18 |
| Pectin | 0.3% XG | 6.62 | 9.08 | 13.08 |

XG, Xanthan gum

Post addition of Aculyn™ 22 to the pectin microcapsules provided increased 5× Toss benefits compared to the control or other rheology modifiers when stored for 4 or 8 weeks at 37° C.

In light of the data presented herein, a pectin capsule of use in the invention is composed of pectin with a combination of isocyanate, tannic acid and lysine as cross-linking agents. Such capsules preferably have a mean diameter of at least 20 microns and are used in combination with a rheology modifier such as Xanthan gum or Aculyn™ 22. Pectin capsules are of particular use in the delivery of fragrances in fabric care products (e.g., conditioners, and liquid detergents).

Example 5: Polypeptide Microcapsule Compositions

Capsules composed of different proteins were prepared and sensory evaluations were conducted. In particular, polypeptide capsules composed of different types of proteins (non-denatured or denatured with different chaotropes) were prepared and compared (Table 21). In addition, different concentrations of chaotrope (Table 22) and different cross-linkers (Tables 23 and 24) were evaluated. Further, process parameters such as pH (Table 25) and cure temperature (Table 26) were evaluated.

Protein sources for the polypeptide capsules included the following: Whey protein concentrate (sold under the tradename HYDROVON® 282 from Glanbia Nutritionals or WPC from Wheyco), Whey Isolate (Hydrovon™ 195 from Glanbia Nutritionals), Pea protein (sold under the tradename NUTRALYS® S85XF or NUTRALYS® S85F from Roquette, or Organic Pea Protein from Z Natural Foods), Potato protein (sold under the tradename TUBERMINE® GP or TUBERMINE® FP from Roquette), Brown Rice protein (Brown Rice Protein from Ingredients Inc., or protein sold under the tradename ORYZATEIN® Silk 90 BR from Z Natural Foods), White Rice protein (Unirice from Roquette), Rice protein (Rice Protein from Kerry), Wheat protein (Wheat Protein from Scoular), Egg protein (Egg Protein from Henningsen Food), Barley Rice protein (Barley Rice Protein from Beretein), or Pumpkin Seed protein (Pumplin Seed Protein from Acetar).

Exemplary polypeptide capsules 1-13, 16-46 and 4C were prepared according to the following procedure with percentages of ingredients indicated in the tables. An aqueous solution of protein and chaotrope was prepared. To the mixture, was added 0.5% sodium polystyrene sulfonate (commercially available under the tradename of FLEXAN® II from AkzoNobel Surface Chemistry, Bridgewater, NJ), and 1% octenyl succinic anhydride (OSA)-modified starch (commercially available under the tradename of PURITY GUM® Ultra from Ingredion, Bridgewater, NJ). For examples with pH lower than or equal to 7, citric acid was added. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (commercially available under the tradename NEOBEE® from Stepan Company, Northfield, IL). The two solutions were mixed and homogenized at 7400-9600 rpm for 3 minutes. Subsequently, cross-linker was added. The resultant mixture was cured at 55° C. for 4 hours or as otherwise indicated.

Exemplary polypeptide capsules 14, 15 and 1C-3C were prepared according to the following procedure with percentages of ingredients indicated in the tables. An aqueous solution of protein was prepared. To the solution was added 0.5% sodium naphthalene sulfonate condensate (commercially available under the tradename MORWET® D-425 from AkzoNobel Surface Chemistry, Bridgewater, NJ), 1% polyvinylpyrrolidone (commercially available under the tradename of LUVIKSOL K90 from BASF, Florham Park, NJ). An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (commercially available under the tradename NEOBEE® from Stepan Company, Northfield, IL). The two solutions were mixed and homogenized at 7400 rpm for 3 minutes. Subsequently, cross-linker was added. The resultant mixture was cured at 55° C. for 4 hours, or as otherwise indicated.

Exemplary polypeptide capsule 47 was prepared by combining the protein and chaotrope in water. To the mixture was added 0.5% sodium polystyrene sulfonate (commercially available under the tradename of FLEXAN®® II from AkzoNobel Surface Chemistry, Bridgewater, NJ), 1% octenyl succinic anhydride (OSA)-modified starch (commercially available under the tradename of PURITY GUMS Ultra from Ingredion, Bridgewater, NJ). An oil solution was prepared that contained trimethylolpropane adduct of xylylenediisocyanate (commercially available under the tradename of TAKENATE® D110N from Mitsui Chemical, Japan), 32% of a model fragrance (IFF, Union Beach, NJ) and 8% caprylic/capric triglyceride (commercially available under the tradename NEOBEE® from Stepan Company, Northfield, IL). The two solutions were mixed and homogenized at 7400 rpm for 3 minutes. Subsequently, cross-linker, was added. The resultant mixture was cured at room temperature for 4 hours.

Exemplary polypeptide capsule 48 was prepared by combining the protein and chaotrope in water. To the mixture was added 0.5% sodium polystyrene sulfonate (commercially available under the tradename of FLEXAN® II from AkzoNobel Surface Chemistry, Bridgewater, NJ), 1% octenyl succinic anhydride (OSA)-modified starch (commercially available under the tradename of PURITY GUM® Ultra from Ingredion, Bridgewater, NJ) and 0.5% tannic acid (commercially available under the tradename of TANAL® 2 from Ajinomoto, Itasca, IL). The solution was pH adjusted to 5 with citric acid. An oil solution was prepared that contained trimethylolpropane adduct of xylylenediisocyanate (commercially available under the tradename of TAKENATE® D110N from Mitsui Chemical, Japan), 32% of a model fragrance (IFF, Union Beach, NJ) and 15%~2% caprylic/capric triglyceride (commercially available under the tradename NEOBEE® from Stepan Company, Northfield, IL). The two solutions were mixed and homogenized at 7400 rpm for 3 minutes. Subsequently, the resultant mixture was cured at 55° C. for 4 hours.

The exemplary fragrance capsules were added to a fabric conditioner at 0.6% NOE and evaluated for post-rub headspace (HS) (Tables 21, 24 and 26) or post-rub sensory performance (Tables 22, 23 and 25). For post-rub headspace, towels were washed with fabric conditioner, dried and headspace in ppb was determined post-rub. For post-rub sensory performance, dried towels were evaluated based on 0-10 intensity after fabric conditioner wash.

TABLE 21

| Ex. | Polypeptide | % Chaotrope | % Isocyanate | Cross-Linker | Free Oil | Post-Rub HS |
|---|---|---|---|---|---|---|
| 1 | 3.0% Denat. Whey Conc. | 1.3% GuHCl | 1.0 | 0.5% TA | 0.2 | 4439 |
| 2 | 3.0% Denat. Whey Conc. | 1.3% GuCarb | 1.0 | 0.5% TA | 0.2 | 4495 |
| 3 | 3.0% Denat. Whey Conc. | 1.3% EtOAc | 1.0 | 0.5% TA | 0.2 | 1872 |
| 4 | 3.0% Denat. Whey Isolate | 1.3% GuCarb | 1.0 | 0.5% TA | 0.1 | 4020 |
| 5 | 3.0% Denat. Naked Rice Protein | 1.3% GuCarb | 1.0 | 0.5% TA | <0.1 | 3430 |
| 6 | 3.0% Denat. Barley Rice Protein | 1.3% GuCarb | 1.0 | 0.5% TA | <0.1 | 2738 |
| 7 | 3.0% Denat. Brown Rice Protein | 1.3% GuCarb | 1.0 | 0.5% TA | 0.5 | 4426 |
| 8 | 3.0% Denat. Pumpkin Seed Protein | 1.3% GuCarb | 1.0 | 0.5% TA | 0.2 | 2680 |
| 9 | 3.0% Denat. Oat Protein | 1.3% GuCarb | 1.0 | 0.5% TA | <0.1 | 1660 |
| 10 | 3.0% Denat. Potato Protein | 1.3% GuCarb | 1.0 | 0.5% TA | 0.3 | 2769 |

TABLE 21-continued

| Ex. | Polypeptide | % Chaotrope | % Isocyanate | Cross-Linker | Free Oil | Post-Rub HS |
|---|---|---|---|---|---|---|
| 11 | 3.0% Denat. Wheat Protein | 1.3% GuCarb | 1.0 | 0.5% TA | <0.1 | 2332 |
| 12 | 3.0% Denat. Egg White Protein | 1.3% GuCarb | 1.0 | 0.5% TA | 0.8 | 2743 |
| 13 | 3.0% Denat. Pea Protein | 1.3% GuCarb | 1.0 | 0.5% TA | 0.3 | 3971 |
| 1C | 3.0% ND Whey Conc. | None | 1.0 | 0.4% GuHCl | 3.4 | 40 |
| 2C | 3.0% ND Pea Protein | None | 1.0 | 0.4% GlutAld | 3.3 | 131 |
| 3C | 3.0% ND Rice Protein | None | 1.0 | 0.4% GlutAld | >5.0 | 35 |
| 4C | None | None | 1.0 | 0.4% GlutAld | 1.2 | 114 |

Denat., denatured;
ND, non-denatured;
Conc., concentrate;
GuHCl, guanidinium hydrochloride;
TA, tannic acid;
GuCarb, guanidinium carbonate;
GlutAld, glutaraldehyde.

Having demonstrated that denatured protein substantially improves capsule performance, different concentrations of guanidinium carbonate as the chaotropic agent were analyzed (Table 22).

TABLE 22

| Ex. | Polypeptide | % Chaotrope | % Isocyanate | Cross-Linker | % Free Oil | Post-Rub |
|---|---|---|---|---|---|---|
| 41 | 3.0% Denat. Whey Conc. | 1.3% GuCarb | 0.5 | 0.5% TA | 0.2 | 4.4 |
| 2 | 3.0% Denat. Whey Conc. | 1.3% GuCarb | 1.0 | 0.5% TA | 0.2 | 4.7 |
| 42 | 3.0% Denat. Whey Conc. | 0.7% GuCarb | 1.0 | 0.5% TA | 0.2 | 3.9 |
| 43 | 3.0% Denat. Whey Conc. | 0.3% GuCarb | 1.0 | 0.5% TA | 0.2 | 3.1 |
| 44 | 3.0% Denat. Whey Conc. | none | 1.0 | 0.5% TA | 0.2 | 2.6 |

Denat., denatured;
Conc., concentrate;
GuCarb, guanidinium carbonate;
TA, tannic acid.

The use of different cross-linkers and cross-linker combinations were also evaluated based upon post-rub sensory performance (Table 23) and post-rub headspace (Table 24). Cross-linkers analyzed included: Tannic Acid (sold under the tradename TANAL® 02, Ajinomoto), Triethyl Citrate (sold under the tradename CITROFLEX®, IFF), BPEI (sold under the tradename LUPASOL®, BASF), Itaconic Acid (Sigma Aldrich, St. Louis, MO), Citric Acid (Sigma Aldrich, St. Louis, MO), Malic Acid (Sigma Aldrich, St. Louis, MO), Maleic Acid (Sigma Aldrich, St. Louis, MO), Dibutyl Itaconate (Sigma Aldrich, St. Louis, MO), Cysteamine (Sigma Aldrich, St. Louis, MO), Lysine (Sigma Aldrich, St. Louis, MO), Maltodextrin (Sigma Aldrich, St. Louis, MO), and Glutaraldehyde (Sigma Aldrich, St. Louis, MO).

TABLE 23

| Ex. | Polypeptide | % Chaotrope | % Isocyanate | Cross-Linker | % Free Oil | Post-Rub |
|---|---|---|---|---|---|---|
| 17 | 3.0% Denat. Whey Conc. | 1.3% GuCarb | 1.0 | 1.0% BPEI | 1.0 | 3.1 |
| 18 | 3.0% Denat. Whey Conc. | 1.3% GuCarb | 1.0 | 1.0% Malto-dextrin | 0.6 | 4.9 |
| 19 | 3.0% Denat. Whey Conc. | 1.3% GuCarb | 1.0 | 0.5% GlutAld | 0.5 | 3.36 |
| 20 | 3.0% Denat. Whey Conc. | 1.3% GuCarb | 1.0 | 1.3% Citric Acid | 0.8 | 4.9 |
| 21 | 3.0% Denat. Whey Conc. | 1.3% GuCarb | 1 .0 | 1.3% Malic Acid | 0.8 | 3.7 |
| 22 | 3.0% Denat. Whey Conc. | 1.3% GuCarb | 0 .4 | 1.3% Malic Acid | 2.1 | 3.7 |
| 23 | 3.0% Denat. Whey Conc. | 1.3% GuCarb | 1.0 | 0.5% TA & 1.0% TEC | NA | NA |
| 24 | 3.0% Denat. Whey Conc. | 1.3% GuCarb | 0.4 | 2.1% TEC & 0.5% BPEI | 0.5 | 5.6 |
| 25 | 3.0% Denat. Whey Conc. | 1.3% GuCarb | 0.3 | 2.1% TEC & 0.5% BPEI | 0.5 | 3.5 |
| 26 | 3.0% Denat. Whey Conc. | 1.3% GuCarb | 0.2 | 2.1% TEC & 0.5% BPEI | 0.6 | 2.2 |
| 27 | 3.0% Denat. Potato Protein | 1.3% GuCarb | 0.4 | 2.1% TEC & 0.5% BPEI | <5% | 3.7 |
| 28 | 1.8% Denat. Pea Protein | 1.3% GuCarb | 0.4 | 2.1% TEC & 0.5% BPEI | 0.4% | 5.4 |
| 29 | 1.8% Denat. Pea Protein | 1.3% GuCarb | 0.3 | 2.1% TEC & 0.5% BPEI | 0.6% | 4.0 |
| 30 | 1.8% Denat. Pea Protein | 1.3% GuCarb | 0.4 | 2.1% TEC & 0.5% Lysine | 0.5% | 4.8 |
| 31 | 1.8% Denat. Pea Protein | 1.3% GuCarb | 0.4 | 2.1% TEC & 0.5% CystAm | 1.0 | 2.6 |
| 32 | 1.8% Denat. Pea Protein | 1.3% GuCarb | 0.4 | 1.9% DBI & 0.5% BPEI | 0.3 | 4.1 |
| 33 | 1.8% Denat. Pea Protein | 1.3% GuCarb | 0.4 | 1.9% DBI & 0.5% Lysine | 0.5 | 3.7 |
| 34 | 1.8% Denat. Pea Protein | 1.3% GuCarb | 0.4 | 1.9% DBI & 0.5% CystAm | 0.9 | 4.6 |
| 3 | 3.0% Denat. Whey Conc. | 1.3% GuCarb | 1.0 | 0.5% TA | 0.5 | 4.8 |
| 16 | None | 0.7% GuCarb | 1.0 | 0.5% TA | 0.1 | 3.8 |

Denat., denatured;
Conc., concentrate;
GuCarb, guanidinium carbonate;
BPEI, branched polyethyleneimine;
GlutAld, glutaraldehyde;
TEC, Triethyl Citrate;
CystAm, Cysteamine;
DBI, Dibutyl Itaconate;
NA, not available.

TABLE 24

| Ex. | Polypeptide | % Chaotrope | % Isocyanate | Cross-Linker | % Free Oil | Post-Rub |
|---|---|---|---|---|---|---|
| 35 | 1.8% Denat. Pea Protein | 1.3% GuCarb | 0.4 | 1.0% Itaconic Acid | 0.7 | 1855 |
| 36 | 1.8% Denat. Pea Protein | 1.3% GuCarb | 0.4 | 1.0% Malic Acid | 0.5 | 2528 |
| 37 | 1.8% Denat. Pea Protein | 1.3% GuCarb | 0.4 | 1.0% Maleic Acid | 0.5 | 1135 |
| 38 | 1.8% Denat. Pea Protein | 1.3% GuCarb | 0.4 | 1.0% Fumaric Acid | 0.6 | 1921 |
| 39 | 1.8% Denat. Pea Protein | 1.3% GuCarb | 0.4 | 2.1% TEC | 0.5 | 1787 |
| 40 | 1.8% Denat. Pea Protein | 1.3% GuCarb | 0.4 | 1.9% DBI | 0.8 | 1538 |

Denat., denatured;
GuCarb, guanidinium carbonate;
TEC, Triethyl Citrate;
DBI, Dibutyl Itaconate.

Process parameters including pH (Table 25) and cure temperature (Table 26) were also evaluated.

TABLE 25

| Ex. | Polypeptide* | % Isocyanate | pH | Cross-Linker | % Free Oil | Post-Rub |
|---|---|---|---|---|---|---|
| 45 | 3.0% Denat. Whey Conc. | 1.0 | 7 | 0.5% TA | 0.2 | 4.5 |
| 2 | 3.0% Denat. Whey Conc. | 1.0 | <7 | 0.5% TA | 0.2 | 4.7 |
| 46 | 3.0% Denat. Whey Conc. | 1.0 | >7 | 0.5% TA | 0.2 | 4.9 |

*Denatured with 1.3% guanidinium carbonate.
Denat., denatured;
Conc., concentrate.

TABLE 26

| Ex. | Polypeptide* | % Isocyanate | Cure Temp | Cross-Linker | % Free Oil | Post-Rub |
|---|---|---|---|---|---|---|
| 1 | 3.0% Denat. Whey Conc. | 1.0 | 55° C. | 0.5% TA | 0.2 | 4731 |
| 47 | 3.0% Denat. Whey Conc. | 1.0 | RT | 0.5% TA | 0.3 | 4615 |

*Denatured with 1.3% guanidinium carbonate.
Denat., denatured;
Conc., concentrate;
TA, tannic acid;
RT, room temperature.

Selected polypeptide capsule compositions were subsequently evaluated for performance in hair conditioner and shampoo applications. The generic hair conditioner base was composed of 4% fatty alcohol, 0.7% Behentrimonium Chloride, 1.0% TAS, 2.5% silicone and 0.5% preservative. The polypeptide capsules were added to the hair conditioner base at a fragrance equivalence of 0.25% in the final product. Performance was evaluated at the post-brush stage, wherein hair swatches were conditioned with the hair conditioner, washed, dried, brushed and rated for fragrance intensity on a scale of 0-10 (Table 27).

TABLE 27

| Ex. | Polypeptide* | % Isocyanate | X-Linker | Post-Rub |
|---|---|---|---|---|
| 17 | 3.0% Denat. Whey Conc. | 1.0 | 1% BPEI | 5.6 |
| 2# | 3.0% Denat. Whey Conc. | 1.0 | 0.5% TA | 4.3 |
| 10# | 3.0% Denat. Potato Protein | 1.0 | 0.5% TA | 3.8 |

*Denatured with 1.3% guanidinium carbonate.
#2% Chitosan (commercially available as GU7522 from Glentham) was added to the capsule composition (as deposition aid) prior to addition to the hair conditioner base.
Denat., denatured; Conc., concentrate; BPEI, branched polyethyleneimine; TA, tannic acid.

The generic hair shampoo base was composed of 12% SLES, 1.6% CAPB, 0.2% Guar, 2-3% silicone and 0.5% preservative. The polypeptides capsules were added to the hair shampoo base at a fragrance equivalence of 0.25% in the final product. Performance was evaluated at the post-brush stage, wherein hair swatches were washed with the shampoo, dried, brushed and rated for fragrance intensity on a scale of 0-10 (Table 28).

TABLE 28

| Ex. | Polypeptide* | % Isocyanate | X-Linker | Post-Rub |
|---|---|---|---|---|
| 2$ | 3.0% Denat. Whey Conc. | 1.0 | 0.5% TA | 7 |
| 17 | 3.0% Denat. Whey Conc. | 1.0 | 1% BPEI | 5.2 |
| 2# | 3.0% Denat. Whey Conc. | 1.0 | 0.5% TA | 6.8 |
| 10# | 3.0% Denat. Potato Protein | 1.0 | 0.5% TA | 2.6 |

*Denatured with 1.3% guanidinium carbonate
$0.25% of a commercial deposition aid polymer was added to the capsule composition prior to addition to the hair conditioner base.
#2% Chitosan (commercially available as GU7522 from Glentham) was added to the capsule composition (as deposition aid) prior to addition to the hair conditioner base.
Denat., denatured; Conc., concentrate; BPEI, branched polyethyleneimine; TA, tannic acid.

To demonstrate the impact of using a reduced amount of isocyanate, pea protein capsules were prepared with 0.58% and 1.0% trimethylolpropane adduct of xylylenediisocyanate (commercially available under the tradename of TAKENATE® D110N from Mitsui Chemical, Japan). The perfumery benefit of the microcapsules was evaluated by conducting a laundry experiment with terry towels. The fragrance intensity was evaluated pre-rub, after gentle tossing (5×) and after vigorous rub touch points on a scale ranging from 0 to 35. This analysis indicated that reduced isocyanate levels reduced performance (Table 29).

TABLE 29

| % Isocyanate | % Free Oil | Particle size mean/mode (micron) | Prerub/5X toss/post-rub |
|---|---|---|---|
| 1% | 0.9 | 26/23.1 | 8.1/9.66/12.09 |
| 0.58% | 1.8 | 36.8/37.6 | 7.66/8.6/10.11 |

Additional analysis was conducted to determine whether microcuring of the capsules at 80° C. for 0.5 hours or adding co-emulsifiers or additional cross-linkers impacted performance of microcapsules prepared with pea protein. An aqueous solution of pea protein was prepared. Where indicated in Table 30, the follow co-emulsifiers were included: 0.5% sodium polystyrene sulfonate (commercially available under the tradename of FLEXAN® II from AkzoNobel Surface Chemistry, Bridgewater, NJ) and 0.1% carboxymethylcellulose; 0.5% polyvinylpyrrolidone and 0.5% Polyquaternium 11; 0.5% PVP and 0.5% sulfonated naphthalene-formaldehyde condensates sold under the trademark MORWET® D425 (Akzo Nobel, Fort Worth, TX); or 1% octenyl succinic anhydride (OSA)-modified starch (sold under the trademark PURITY GUM® Ultra by Ingredion, Bridgewater, NJ) and 0.5% sodium polystyrene sulfonate sold under the tradename of FLEXAN® II. An oil solution was prepared that contained trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (commercially available under the tradename NEOBEE® from Stepan Company, Northfield, IL). The two solutions were mixed and homogenized at 7400~9600 rpm for 3 minutes. The pH was adjusted to pH 8. Where indicated, cross-linker (hexamethylenediamine, branched polyethylene imine guanidine carbonate) was added. The resultant mixture was cured at 55° C. for 4 hours with or without microcuring at 80° C. for 0.5 hours. The perfumery benefit of the microcapsules was evaluated by conducting a laundry experiment with terry towels. The fragrance intensity was evaluated pre-rub, after gentle tossing (5×) and after vigorous rub touch points on a scale ranging from 0 to 35 (Table 30) or headspace analysis post-rub was determined (Table 31).

TABLE 30

| Process Components | % Free Oil | Particle size mean/mode (micron) | Prerub/ post-rub |
|---|---|---|---|
| 0.9% Pea protein/1% isocyanate, no microcure | 2.5 | 10/21 | 0.6/3.6 |
| 0.9% Pea protein/1% isocyanate, with microcure | 2.9 | 9/21 | 0.6/3.6 |
| 0.9% Pea protein/CMC + SPS co-emulsifier/1% isocyanate, no microcure | 1.3 | 25/16 | 0.6/2.8 |
| 0.9% Pea protein/CMC + SPS co-emulsifier/1% isocyanate, with microcure | 0.9 | 27/16 | 0.2/1.2 |
| 0.9% Pea protein/CMC + SPS co-emulsifier/1% isocyanate/0.65% GuCarb, no microcure | 0.3 | 49/34 | 0.4/5.6 |
| 0.9% Pea protein/CMC + SPS co-emulsifier/1% isocyanate/0.65% GuCarb, with microcure | 0.5 | 45/35 | 0.4/4.2 |
| 0.9% Pea protein/CMC + SPS co-emulsifier/1% isocyanate/1.3% HMDA, with microcure | 25/22 | >5 | Free oil too high |
| 0.9% Pea protein/CMC + SPS co-emulsifier/1% isocyanate/0.65% BPEI, with microcure | 52/17 | 3.4 | Sample too viscous to test |
| 0.9% Pea protein/PVP + PQ11 co-emulsifier/1% isocyanate, no microcure | 0.3 | 23/29 | 1.3/4.4 |
| 0.9% Pea protein/PVP + PQ11 co-emulsifier/1% isocyanate, with microcure | 0.3 | 23/29 | 1.1/4.8 |
| 0.9% Pea protein/PVP + PQ11 co-emulsifier/1% isocyanate/0.65% GuCarb, with microcure | 0.1 | 56/55 | 1.4/4.4 |

TABLE 30-continued

| Process Components | % Free Oil | Particle size mean/mode (micron) | Prerub/ post-rub |
|---|---|---|---|
| 0.9% Pea protein/PVP + PQ11 co-emulsifier/1% isocyanate/0.65% GuCarb, with micro cure | 0.3 | 56/55 | 1/5 |
| 0.9% Pea protein/PVP + PQ11 co-emulsifier/1% isocyanate/1.3% HMDA, with microcure | >5 | 21.5/21.6 | 0.21/1.86 |
| 0.9% Pea protein/PVP + PQ11 co-emulsifier/1% isocyanate/0.65% BPEI, with microcure | 2.6 | 35/29 | Sample too viscous to test |
| 0.9% Pea protein/PVP + PNS co-emulsifier/1% isocyanate, no microcure | >5 | 21/8 | 0.75/4.5 |
| 0.9% Pea protein/PVP + PNS co-emulsifier/1% isocyanate, with microcure | >5 | 29/8 | 0.75/0.88 |
| 0.9% Pea protein/PVP + PNS co-emulsifier/1% isocyanate/0.65% GuCarb, with microcure | 0.7 | 28/20 | 0.75/4.25 |
| 0.9% Pea protein/PVP + PNS co-emulsifier/1% isocyanate/0.65% GuCarb, with microcure | 0.9 | 32/21 | 0.75/4 |
| 0.9% Pea protein/PVP + PNS co-emulsifier/1% isocyanate/1.3% HMDA, with microcure | >5 | 31/22 | Free oil too high to test |
| 0.9% Pea protein/PVP + PNS co-emulsifier/1% isocyanate/0.65% BPEI, with microcure | >5 | 74/48 | Sample too viscous to test |

GuCarb, Guanidine carbonate; SPS, sodium polystyrene sulfonate; CMC, carboxymethylcellulose; PVP, polyvinylpyrrolidone; PQ11, Polyquaternium 11; PNS, sulfonated naphthalene-formaldehyde condensates; SPS, sodium polystyrene sulfonate; HMDA, Hexamethylenediamine; BPEI, branched polyethyleneimine.

TABLE 31

| Process Components | % Free Oil | Particle size mean/mode (micron) | Head-space (ppb) |
|---|---|---|---|
| 0.9% Pea protein/PGU + SPS co-emulsifier/1% isocyanate, no microcure | 1.8 | 18/20 | 1975 |
| 0.9% Pea protein/PGU + SPS co-emulsifier/1% isocyanate, with microcure | 1.6 | 18/20 | 3478 |
| 0.9% Pea protein/PGU + SPS co-emulsifier/1% isocyanate/0.65 GuCarb, with microcure | 0.2 | 43/50 | 3078 |
| 0.9% Pea protein/PGU + SPS co-emulsifier/1% isocyanate/0.65 GuCarb, with microcure | 0.3 | 43/50 | 3423 |
| 0.9% Pea protein/PGU + SPS co-emulsifier/1% isocyanate/0.65% BPEI, with microcure | Fail | Fail | Fail |
| 0.9% Pea protein/PGU + SPS co-emulsifier/1% isocyanate/1.3% HMDA, with microcure | >5% | 25/20 | Free oil too high to test |

GuCarb, Guanidine carbonate; PGU, OSA-modified starch; SPS, sodium polystyrene sulfonate; HMDA, Hexamethylenediamine; BPEI, branched polyethyleneimine.

The amount of pea protein used and order (pre-emulsion or post-emulsion) in which the guanidine carbonate as cross-linker was added were also varied. An aqueous solution of pea protein (0.9% or 1.8%) was prepared and combined with 0.5% sodium polystyrene sulfonate (commercially available under the tradename of FLEXAN® II from AkzoNobel Surface Chemistry, Bridgewater, NJ) and 1% octenyl succinic anhydride (OSA)-modified starch (sold under the trademark PURITY GUM® Ultra by Ingredion, Bridgewater, NJ) as co-emulsifiers. An oil solution was prepared that contained 1% trimethylolpropane adduct of xylylenediisocyanate (commercially available under the tradename of TAKENATE® D110N from Mitsui Chemical, Japan), 25%~38% of a model fragrance (IFF, Union Beach, NJ) and 15%~2% caprylic/capric triglyceride (commercially available under the tradename NEOBEE® from Stepan Company, Northfield, IL). The two solutions were mixed and homogenized at 7400~9600 rpm for 3 minutes. The pH was adjusted to pH 8. The resultant mixture was cured at 55° C. for 4 hours and optionally microcured at 80° C. for 0.5 hours. The perfumery benefit of the microcapsules was evaluated by conducting a laundry experiment with terry towels. The fragrance intensity was evaluated pre-rub, after gentle tossing (5×) and after vigorous rub touch points on a scale ranging from 0 to 35 (Table 32).

TABLE 32

| Capsule | % Free Oil | Particle size (mean/mode, micron) | Prerub/post-rub |
|---|---|---|---|
| 0.9% Pea protein/0.65% guanidine, no microcure | 2.7 | Emulsion (20.8/22) Capsules (21.5/23.1) | 8.08/11.49 |
| 0.9% Pea protein/no guanidine, no microcure | 2.7 | Emulsion (20.8/22) Capsules (44.5/24.0) | 7.84/10.55 |
| 1.8% Pea protein/0.65% guanidine added pre-emulsion, with microcure | 2.5 | Emulsion (17.2/14.3) Capsules (88/153) | 8.95/11.9 |
| 0.9% Pea protein/0.65% guanidine added pre-emulsion, with microcure | 2.2 | Emulsion (15.2/16.7) Capsules (36/18) | 7.68/12.79 |
| 0.9% Pea protein/1.3% guanidine added pre-emulsion | 1 | Emulsion (21.9/20.5) Capsules (27.4/21.8) | 0.8/6.25 |
| 0.9% Pea protein/1.3% guanidine added post-emulsion | 5 | Emulsion (25.6/14.1) Capsules (37.8/14.8) | 0.2/2.2 |

The effect of particle size on the strength of the pea protein microcapsules was determined. This analysis indicated that capsules with a mean diameter below 20 microns were weak, whereas particles with a mean diameter greater than 20 microns exhibited superior strength (Table 33) and dry sensory performance.

TABLE 33

| Mean particle Diameter (micron) | % Deformation | Stress (MPa) | Nominal tension (N/m) |
|---|---|---|---|
| 17.22 | 33.69 | 0.06 | 0.25 |
| 29.89 | 54.74 | 0.3 | 2.31 |

In light of the data presented herein, a polypeptide capsule of use in the invention is composed of denatured whey or denatured pea protein with isocyanate (e.g., 1.0 wt. %) as a primary cross-linking agent and optionally a secondary cross-linking agent such as BPEI, tannic acid, a polyacid (e.g., citric acid, malic acid, maleic acid, fumaric acid, glutaric acid, crotonic acid, or itaconic acid), glutaraldehyde, a polyol, or a polyamine. Such capsules preferably have a mean diameter greater than 20 microns and are used in combination with a rheology modifier such as xanthan gum, cationic HEC, or cationic guar gum. Polypeptide capsules are of particular use in the delivery of fragrances in fabric care products (e.g., conditioners, and liquid and powder detergents), hair care products (e.g., conditioners and shampoos), antiperspirants, deodorants and fine fragrance products.

Example 6: Biodegradability

Biodegradability testing is carried out according to protocol OECD 310. An aliquot of microcapsule slurry is placed into Biological Oxygen Demand (BOD) bottles in water containing a microbial inoculum. The bottles are checked for carbon dioxide evolution at a regular interval for 28 days. Intermittent points can also be taken since an asymptotic value may be reached much sooner than 28 days. The percent degradation is analyzed against the positive control starch.

The biodegradability of the whey protein microcapsule composition of Example 5, HEC microcapsule composition of Example 2 and Guar microcapsule composition of Example 1 were compared. This analysis indicated that as of 20 days, more than 10% of the material in these samples had degraded.

Example 7: Hair Shampoo Formulations Containing Microcapsules

Biodegradable core-shell microcapsules from the above examples are formulated into a rinse-off shampoo formulation by combining 90.0 grams of a shampoo formulation (with typical formulations presented in Tables 34-35) with an appropriate amount of microcapsule slurry to deliver to deliver 1% fragrance oil equivalent. The microcapsules and water are added on top of the shampoo formulation, then the contents are mixed at high shear, 4000-6000 rpm for 1-2 minutes.

TABLE 34

| | Formulation (wt %) | | | | |
|---|---|---|---|---|---|
| Ingredient | 1 | 2 | 3 | 4 | 5 |
| Water | QS | QS | QS | QS | QS |
| Polyquaternium 76 | 2.50 | 2.50 | 2.50 | 2.50 | 2.50 |
| Sodium laureth sulfate | 21.43 | 21.43 | 21.43 | 21.43 | 21.43 |
| Sodium lauryl sulfate | 20.69 | 20.69 | 20.69 | 20.69 | 20.69 |
| Silicone | 0.75 | 0.75 | 0.75 | 0.75 | 0.75 |
| Cocoamidopropyl betaine | 3.33 | 3.33 | 3.33 | 3.33 | 3.33 |
| Cocoamide MEA | 1.0 | 1.0 | 1.0 | 1.0 | 1.0 |
| Ethylene glycol distearate | 1.50 | 1.50 | 1.50 | 1.50 | 1.50 |
| Sodium chloride* | 0.25 | 0.25 | 0.25 | 0.25 | 0.25 |
| Fragrance | 0.70 | 0.70 | 0.70 | 0.70 | 0.70 |
| HEC Microcapsules | 3.0 | 0 | 0 | 0 | 0 |
| Guar Microcapsules | 0 | 3.0 | 0 | 0 | 0 |
| Whey Microcapsules | 0 | 0 | 3.0 | 0 | 0 |
| Lignin Microcapsules | 0 | 0 | 0 | 3.0 | 0 |
| Pectin Microcapsules | 0 | 0 | 0 | 0 | 3.0 |

QS, indicates that this material is used to bring the total to 100%.

TABLE 35

| | Formulation (wt %) | | | | |
|---|---|---|---|---|---|
| Ingredient | 11 | 12 | 13 | 14 | 15 |
| Sodium laureth sulfate | 10.00 | 10.00 | 10.00 | 10.00 | 10.00 |
| Sodium lauryl sulfate | 1.50 | 1.50 | 1.50 | 1.50 | 1.50 |
| Cocoamido-propyl betaine | 2.00 | 2.00 | 2.00 | 2.00 | 2.00 |
| Guar hydroxypropyl trimonium chloride | 0.40 | 0.40 | 0.40 | 0.40 | 0.40 |
| Dimethicone | 2.00 | 2.00 | 2.00 | 2.00 | 2.00 |
| Ethylene glycol distearate | 1.50 | 1.50 | 1.50 | 1.50 | 1.50 |
| 5-chloro-2-methyl-4-isothiazolin-3-one, Kathon CG | 0.0005 | 0.0005 | 0.0005 | 0.0005 | 0.0005 |
| Sodium benzoate | 0.25 | 0.25 | 0.25 | 0.25 | 0.25 |
| Disodium EDTA | 0.13 | 0.13 | 0.13 | 0.13 | 0.13 |
| Fragrance | 0.7 | 0.7 | 0.7 | 0.7 | 0.7 |
| HEC Microcapsules | 3.0 | 0 | 0 | 0 | 0 |
| Guar Microcapsules | 0 | 3.0 | 0 | 0 | 0 |
| Whey Microcapsules | 0 | 0 | 3.0 | 0 | 0 |
| Lignin Microcapsules | 0 | 0 | 0 | 3.0 | 0 |
| Pectin Microcapsules | 0 | 0 | 0 | 0 | 3.0 |
| Citric acid/sodium citrate dihydrate | pH QS* | pH QS* | pH QS* | pH QS* | pH QS* |
| Sodium chloride | Visc. QS* | Visc. QS* | Visc. QS* | Visc. QS* | Visc. QS* |
| Water | QS* | QS* | QS* | QS* | QS* |

*Water, pH and salt are adjustable and can be increased or decrease to respectively achieve target weight, pH and viscosity.

The perfumery benefit of the hair shampoo formulations is evaluated using the protocol below. Each sample thus prepared (2 g) is added to 2 bundles of hair swatch (8 strands) that is wetted under water, with excess water squeezed lightly. The swatches are then rinsed under a stream of water (38° C., 1 gallon/minute) for 45 seconds. Excess water from hair is removed. Hair swatches are then line-dried for 24 hours followed by sensory evaluation by a panel of judges. The fragrance intensity is rated on a scale ranging from 0 to 10. A numerical value of 5 indicates the hair swatches produce a strong intensity, while a value of 10 indicates the hair swatches generate a very strong smell. One hair swatch is evaluated without brushing with a comb to obtain the pre-brush fragrance intensity and the other is used to obtain the post-brush fragrance intensity after brushing it with a standard hair comb.

Example 8: Hair Conditioner Formulations Containing Microcapsules

Biodegradable core-shell microcapsules are formulated into a rinse-off hair conditioner to deliver 1% fragrance oil equivalent. An exemplary formulation is presented in Table 36.

TABLE 36

| | Formulation (grams) | | | | |
|---|---|---|---|---|---|
| Ingredient | 16 | 17 | 18 | 19 | 20 |
| Aminosilicone-1* | 0.50 | 0.50 | 0.50 | 0.50 | 0.50 |
| HEC Microcapsules | 0.40 | 0 | 0 | 0 | 0 |
| Guar Microcapsules | 0 | 0.40 | 0 | 0 | 0 |
| Whey Microcapsules | 0 | 0 | 0.40 | 0 | 0 |
| Lignin Microcapsules | 0 | 0 | 0 | 0.40 | 0 |
| Pectin Microcapsules | 0 | 0 | 0 | 0 | 0.4 |
| Behenyl Trimethylammonium chloride | 2.30 | 2.30 | 2.30 | 2.30 | 2.30 |
| Cetyl alcohol | 1.50 | 1.50 | 1.50 | 1.50 | 1.50 |
| Stearyl alcohol | 3.80 | 3.80 | 3.80 | 3.80 | 3.80 |
| Water | QS | QS | QS | QS | QS |
| Preservative | 0.40 | 0.40 | 0.40 | 0.40 | 0.40 |

*Aminosilicone-1 (AMD): having an amine content of 0.12-0.15 m mol/g and a viscosity of 3,000-8,000 mPas, which is water insoluble.

Example 9: Powder Detergent Formulations Containing Microcapsules

Biodegradable core-shell microcapsules are formulated into a granular laundry detergent compositions for hand washing or washing machines, typically top-loading washing machines (Table 37), or front-loading automatic washing machines (Table 38).

TABLE 37

| | Formulation (wt %) | | | | |
|---|---|---|---|---|---|
| Ingredient | 21 | 22 | 23 | 24 | 25 |
| Linear alkylbenzenesulfonate | 22 | 22 | 22 | 22 | 22 |
| $C_{12-14}$ dimethylhydroxyethyl ammonium chloride | 0.2 | 0.2 | 0.2 | 0.2 | 0.2 |
| AE3S | 1 | 1 | 1 | 1 | 1 |
| Zeolite A | 1 | 1 | 1 | 1 | 1 |
| 1.6 R silicate ($SiO_2$:$Na_2O$ at ratio 1.6:1) | 5 | 5 | 5 | 5 | 5 |
| Sodium carbonate | 20 | 20 | 20 | 20 | 20 |
| Polyacrylate MW 4500 | 0.6 | 0.6 | 0.6 | 0.6 | 0.6 |
| Carboxymethyl cellulose | 0.3 | 0.3 | 0.3 | 0.3 | 0.3 |
| STAINZYME ® (20 mg active/g) | 0.2 | 0.2 | 0.2 | 0.2 | 0.2 |
| Protease (SAVINASE ®, 32.89 mg active/g) | 0.1 | 0.1 | 0.1 | 0.1 | 0.1 |
| Lipase-LIPEX ® (18 mg active/g) | 0.07 | 0.07 | 0.07 | 0.07 | 0.07 |
| Fluorescent brightener | 0.06 | 0.06 | 0.06 | 0.06 | 0.06 |
| DTPA | 0.8 | 0.8 | 0.8 | 0.8 | 0.8 |
| $MgSO_4$ | 1 | 1 | 1 | 1 | 1 |
| Sodium percarbonate | 5.2 | 5.2 | 5.2 | 5.2 | 5.2 |
| TAED | 1.2 | 1.2 | 1.2 | 1.2 | 1.2 |
| Neat Fragrance | 0.5 | 0.5 | 0.5 | 0.5 | 0.5 |
| HEC Microcapsules | 3.0 | 0 | 0 | 0 | 0 |
| Guar Microcapsules | 0 | 3.0 | 0 | 0 | 0 |
| Whey Microcapsules | 0 | 0 | 3.0 | 0 | 0 |
| Lignin Microcapsules | 0 | 0 | 0 | 3.0 | 0 |
| Pectin Microcapsules | 0 | 0 | 0 | 0 | 3.0 |

TABLE 38

| | Formulation (wt %) | | | | |
|---|---|---|---|---|---|
| Ingredient | 26 | 27 | 28 | 29 | 30 |
| Linear alkylbenzene-sulfonate | 8 | 8 | 8 | 8 | 8 |
| $C_{12-14}$ alkylsulfate | 1 | 1 | 1 | 1 | 1 |
| AE7 | 2.2 | 2.2 | 2.2 | 2.2 | 2.2 |
| $C_{10-12}$ dimethyl hydroxyethyl-ammonium chloride | 0.75 | 0.75 | 0.75 | 0.75 | 0.75 |
| Crystalline layered silicate (δ-$Na_2Si_2O_5$) | 4.1 | 4.1 | 4.1 | 4.1 | 4.1 |
| Zeolite A | 5 | 5 | 5 | 5 | 5 |
| Citric Acid | 3 | 3 | 3 | 3 | 3 |
| Sodium Carbonate | 15 | 15 | 15 | 15 | 15 |
| Silicate 2 R ($SiO_2$:$Na_2O$ at ratio 2:1) | 0.08 | 0.08 | 0.08 | 0.08 | 0.08 |
| Soil Release agent | 0.75 | 0.75 | 0.75 | 0.75 | 0.75 |
| Acrylic Acid/Maleic acid Copolymer | 1.1 | 1.1 | 1.1 | 1.1 | 1.1 |
| Carboxymethyl cellulose | 0.15 | 0.15 | 0.15 | 0.15 | 0.15 |
| Protease-PURAFECT ® (84 mg active/g) | 0.2 | 0.2 | 0.2 | 0.2 | 0.2 |
| Amylase-STAINZYME ®, 20 mg active/g) | 0.2 | 0.2 | 0.2 | 0.2 | 0.2 |
| Lipase-LIPEX ® (18 mg active/g) | 0.05 | 0.05 | 0.05 | 0.05 | 0.05 |
| Amylase-NATALASE ®, 8.65 mg active/g) | 0.1 | 0.1 | 0.1 | 0.1 | 0.1 |
| TAED | 3.6 | 3.6 | 3.6 | 3.6 | 3.6 |
| Percarbonate | 13 | 13 | 13 | 13 | 13 |
| Na salt of EDDS | 0.2 | 0.2 | 0.2 | 0.2 | 0.2 |
| HEDP | 0.2 | 0.2 | 0.2 | 0.2 | 0.2 |
| $MgSO_4$ | 0.42 | 0.42 | 0.42 | 0.42 | 0.42 |
| Neat Fragrance | 0.5 | 0.5 | 0.5 | 0.5 | 0.5 |
| Suds suppressor agglomerate | 0.05 | 0.05 | 0.05 | 0.05 | 0.05 |
| soap | 0.45 | 0.45 | 0.45 | 0.45 | 0.45 |
| Sulfonated zine phthalocanine (active) | 0.0007 | 0.0007 | 0.0007 | 0.0007 | 0.0007 |
| S-ACMC | 0.01 | | | | |
| HEC Microcapsules | 1.5 | 0 | 0 | 0 | 0 |
| Guar Microcapsules | 0 | 1.5 | 0 | 0 | 0 |
| Whey Microcapsules | 0 | 0 | 1.5 | 0 | 0 |
| Lignin Microcapsules | 0 | 0 | 0 | 1.5 | 0 |
| Pectin Microcapsules | 0 | 0 | 0 | 0 | 1.5 |

EDDS, ethylenediamine-N,N'-disuccinic acid (S,S) isomer.
HEDP, hydroxyethane diphosphate.

Example 10: Body Lotion Formulations Containing Microcapsules

In a suitable container, biodegradable core-shell microcapsules are combined with the ingredients of Phase A (Table 39). In a separate suitable container, ingredients of Phase B are combined (Table 39). Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as the temperature decreases will result in lower observed hardness values at 21 and 33° C.

TABLE 39

| | Formulation (wt %) | | | | |
|---|---|---|---|---|---|
| Ingredient | 31 | 32 | 33 | 34 | 35 |
| PHASE A | | | | | |
| 12.5% dimethicone crosspolymer in cyclopentasiloxane | 8.6 | 8.6 | 8.6 | 8.6 | 8.6 |
| Dimethicone | 4.09 | 4.09 | 4.09 | 4.09 | 4.09 |
| Polymethylisesquioxane | 4.09 | 4.09 | 4.09 | 4.09 | 4.09 |
| Cyclomethicone | 11.43 | 11.43 | 11.43 | 11.43 | 11.43 |
| 25% dimethicone PEG-10/15 crosspolymer in dimethicone | 5.37 | 5.37 | 5.37 | 5.37 | 5.37 |
| Polyethylene wax | 3.54 | 3.54 | 3.54 | 3.54 | 3.54 |
| DC-2503 cosmetic wax | 7.08 | 7.08 | 7.08 | 7.08 | 7.08 |
| $TiO_2$ coated Mica | 1.00 | 1.00 | 1.00 | 1.00 | 1.00 |
| HEC Microcapsules | 2.5 | 0 | 0 | 0 | 0 |
| Guar Microcapsules | 0 | 2.5 | 0 | 0 | 0 |
| Whey Microcapsules | 0 | 0 | 2.5 | 0 | 0 |
| Lignin Microcapsules | 0 | 0 | 0 | 2.5 | 0 |
| Pectin Microcapsules | 0 | 0 | 0 | 0 | 2.5 |
| PHASE B | | | | | |
| Glycerin | 10 | 10 | 10 | 10 | 10 |
| Dexpanthenol | 0.5 | 0.5 | 0.5 | 0.5 | 0.5 |
| Pentylene Glycol | 3 | 3 | 3 | 3 | 3 |
| Hexamidine Diisethionate | 0.1 | 0.1 | 0.1 | 0.1 | 0.1 |
| Niacinamide | 5 | 5 | 5 | 5 | 5 |
| Methylparaben | 0.2 | 0.2 | 0.2 | 0.2 | 0.2 |
| Ethylparaben | 0.05 | 0.05 | 0.05 | 0.05 | 0.05 |
| Sodium citrate | 0.2 | 0.2 | 0.2 | 0.2 | 0.2 |
| Citric Acid | 0.03 | 0.03 | 0.03 | 0.03 | 0.03 |
| Sodium Benzoate | 0.05 | 0.05 | 0.05 | 0.05 | 0.05 |
| Sodium Chloride | 0.5 | 0.5 | 0.5 | 0.5 | 0.5 |
| FD&C Red #40 | 0.05 | 0.05 | 0.05 | 0.05 | 0.05 |
| Water | QS to 100 | QS to 100 | QS to 100 | QS to 100 | QS to 100 |

*Additionally or alternatively, the composition may include one or more other skin care actives, their salts and derivatives, as disclosed herein, in amounts also disclosed herein as would be deemed suitable by one of skill in the art.

Example 11: Antiperspirant/Deodorant Formulations Containing Microcapsules

An exemplary clear deodorant stick formulation is provided in Table 40.

TABLE 40

| Ingredient | Percentage |
|---|---|
| Water | 20 |
| Phosphatidylglycerol/Diphosphatidylglycerol | 55 |
| Sodium Stearate | 6 |
| PEG-4 | 15 |
| Antibacterial Agent | 0.1 |

An exemplary antiperspirant emulsion spray formulation is provided in Table 41.

TABLE 41

| Ingredient | Percentage |
|---|---|
| Water | to 100 |
| Dimethicone | 6 |

TABLE 41-continued

| Ingredient | Percentage |
|---|---|
| Aluminum Chlorohydrate | 5-6 |
| EDTA | 0.15 |
| Lauryl PEG-9 Polydimethylsiloxyethyl Dimethicone | 0.3 |
| Phenoxyethanol | 0.3 |
| Isobutane | 70 |

An exemplary antiperspirant emulsion roll-on formulation is provided in Table 42.

TABLE 42

| Ingredient | Percentage |
|---|---|
| Water | to 100 |
| Aluminum Chlorohydrate or Aluminum Zirconium Tetrachlorohydrex Gly | 32-36 |
| Steareth-2, Steareth-20 | 0.5-4 |
| Silica | 1-5 |
| Glycerin | 3-5 |
| Dimethicone | 0.5 |

An exemplary antiperspirant clear emulsion stick formulation is provided in Table 43.

TABLE 43

| Ingredient | Percentage |
|---|---|
| Water | 40 |
| Aluminum Zirconium Tetrachlorohydrex Gly | 20 |
| Stearyl Alcohol | 30 |
| C12-C15 Alkyl Benzoate | 25 |
| Glycine | 7 |
| Dimethicone | 0.07 |

An exemplary antiperspirant opaque emulsion stick formulation is provided in Table 44.

TABLE 44

| Ingredient | Percentage |
|---|---|
| Water | to 100 |
| Aluminum Chlorohydrate | 40 |
| Isopropyl Palmitate | 9 |
| Dimethicone | 5.8 |
| Synthetic Wax | 9 |
| Beheneth-10 | 2 |
| Polyglyceryl-3 Diisosterate | 0.3 |
| Acrylates Copolymer | 0.3 |
| PEG/PPG-18/18 Dimethicone | 2 |
| Phenoxyethanol | 0.5 |
| Pentylene Glycol | 0.5 |
| Cetyl PEG/PPG-10/1 Dimethicone | 2 |

An exemplary deodorant spray formulation is provided in Table 45.

TABLE 45

| Ingredient | Percentage |
|---|---|
| Denatured Alcohol | 45 |
| Polyaminopropyl biguanide stearate | 0.2-0.5 |
| Butane, Isobutane, Propane, 152A | 55 |

An exemplary antiperspirant clear gel formulation is provided in Table 46.

TABLE 46

| Ingredient | Percentage |
|---|---|
| Water | 20 |
| Aluminum Zirconium Tetrachlorohydrex Gly | 25 |
| Silicone | 40 |
| Phosphatidylglycerol | 10 |
| Emulsifier | 10 |

What is claimed is:

1. A consumer product with controlled release of an active material comprising (a) a consumer product base; and (b) a biodegradable core-shell microcapsule composition, (i) the core of the biodegradable core-shell microcapsule comprising at least one active material, and (ii) the shell of the biodegradable core-shell microcapsule, which is made of a continuous polymeric phase comprising at least one biopolymer cross-linked with one or more cross-linking agents, the one or more cross-linking agents is a polyisocyanate in combination with tannic acid and optionally a multifunctional aldehyde, wherein said microcapsule retains the at least one active material for at least four weeks at elevated temperature in the consumer product base and releases the at least one active material in response to at least one triggering condition, wherein the weight ratio between the at least one biopolymer and the one or more cross-linking agents is in the range of 60:1 to 3:10, and wherein the shell of the biodegradable core-shell microcapsule is free of a spray dry carrier.

2. The consumer product of claim 1, wherein the consumer product base comprises one or more bleach activators, surfactants, builders, chelating agents, dye transfer inhibiting agents, dispersants, enzymes, and enzyme stabilizers, catalytic metal complexes, polymeric dispersing agents, deposition agents, clay and soil removal or anti-redeposition agents, brighteners, suds suppressors, dyes, perfumes and perfume delivery systems, structure elasticizing agents, fabric softeners, carriers, hydrotropes, processing aids, structurants, anti-agglomeration agents, formaldehyde scavengers, pigments, or a combination thereof.

3. The consumer product of claim 1, wherein said consumer product is a baby care product, a diaper rash cream or balm, a baby powder, a baby wipe, a cosmetic preparation, a powder foundation, a liquid foundation, an eye shadow, a lipstick or lip balm, a home care product, an all-purpose cleaner, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a diaper, a bib, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, or a wildlife scent.

4. The consumer product of claim 1, wherein the at least one biopolymer is a whey protein, plant storage protein, gelatin, starch, modified starch, dextran, dextrin, cellulose, modified cellulose, hemicellulose, pectin, chitin, chitosan, gum, modified gum, lignin, or a combination thereof.

5. The consumer product of claim 4, wherein the whey protein or plant storage protein is denatured.

6. The consumer product of claim 1, wherein the at least one active material is a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, or a combination thereof.

7. The consumer product of claim 1, wherein the one or more cross-linking agents is a polyisocyanate in combination with tannic acid and a multifunctional aldehyde.

8. The consumer product of claim 7, wherein the multifunctional aldehyde is glutaraldehyde.

9. The consumer product of claim 7, wherein the tannic acid reacts with the multifunctional aldehyde to form an acetal or hemi-acetal polymer.

10. The consumer product of claim 1, wherein the weight ratio between the at least one biopolymer and the one or more cross-linking agents is in the range of 12:1 to 3:10.

11. The consumer product of claim 1, wherein the polyisocyanate is a polyisocyanurate of toluene diisocyanate, a trimethylol propane-adduct of toluene diisocyanate or a trimethylol propane-adduct of xylylene diisocyanate.

* * * * *